United States Patent
Fink et al.

(10) Patent No.: US 11,945,834 B2
(45) Date of Patent: Apr. 2, 2024

(54) CYCLIC DINUCLEOTIDES AS ANTICANCER AGENTS

(71) Applicant: BRISTOL-MYERS SQUIBB COMPANY, Princeton, NJ (US)

(72) Inventors: Brian E. Fink, Yardley, PA (US); Zheming Ruan, Dayton, NJ (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 877 days.

(21) Appl. No.: 16/978,208

(22) PCT Filed: Mar. 7, 2019

(86) PCT No.: PCT/US2019/021145
§ 371 (c)(1),
(2) Date: Sep. 4, 2020

(87) PCT Pub. No.: WO2019/173587
PCT Pub. Date: Sep. 12, 2019

(65) Prior Publication Data
US 2021/0002323 A1    Jan. 7, 2021

Related U.S. Application Data

(60) Provisional application No. 62/640,325, filed on Mar. 8, 2018.

(51) Int. Cl.
C07H 21/02    (2006.01)
C07K 16/28    (2006.01)

(52) U.S. Cl.
CPC ......... *C07H 21/02* (2013.01); *C07K 16/2818* (2013.01)

(58) Field of Classification Search
CPC .................................................. C07H 21/02
See application file for complete search history.

(56) References Cited

U.S. PATENT DOCUMENTS

| 10,106,574 | B2* | 10/2018 | Altman | C07H 21/02 |
| 10,519,188 | B2* | 12/2019 | Zhong | C07H 21/04 |
| 10,947,263 | B2* | 3/2021 | Qin | C07H 21/02 |
| 10,953,032 | B2* | 3/2021 | Dodd | C07H 21/04 |
| 11,427,610 | B2* | 8/2022 | Fink | A61P 35/00 |
| 11,660,311 | B2* | 5/2023 | Fink | C07H 21/02 |
| | | | | 514/44 R |

FOREIGN PATENT DOCUMENTS

| WO | 2017123657 A1 | 7/2017 |
| WO | 2017161349 A1 | 9/2017 |
| WO | 19074887 A1 | 4/2019 |

OTHER PUBLICATIONS

U.S. Appl. No. 16/047,071, filed Jul. 27, 2018, Granted.
U.S. Appl. No. 16/642,424, filed Feb. 27, 2020, Filed.
PCT/US2018/048666, Filing date: Aug. 30, 2018, Published.
U.S. Appl. No. 16/641,679, filed Feb. 25, 2020, Allowed.
PCT/US2018/048662, Filing date: Aug. 30, 2018, Published.
U.S. Appl. No. 16/642,440, filed Feb. 27, 2020, Filed.
PCT/US2018/048658, Filing date: Aug. 30, 2018, Published.
U.S. Appl. No. 16/754,301, filed Apr. 7, 2020, Expired.
PCT/USZ018/054944, Filing date: Sep. 10, 2018, Published.
U.S. Appl. No. 16/849,091, filed Apr. 15, 2020, Filed.
PCT/USZ018/056030, Filing date: Oct. 16, 2018, Published.
U.S. Appl. No. 15/748,685, filed Jan. 30, 2018, Granted.
U.S. Appl. No. 16/069,201, filed Jul. 11, 2018, Granted.
U.S. Appl. No. 16/778,281, filed Jan. 31, 2020, Filed.
PCT/USZ017/013066, Filing date: Jan. 11, 2017, Published.
PCT/USZ017/013049, Filing date: Jan. 11, 2017, Published.
U.S. Appl. No. 16/272,172, filed Feb. 11, 2019, Granted.
U.S. Appl. No. 16/683,667, filed Nov. 14, 2019, Filed.
PCT/USZ019/017740, Filing date: Feb. 13, 2019, Published.

* cited by examiner

*Primary Examiner* — Golam M Shameem
(74) *Attorney, Agent, or Firm* — Elliott Korsen

(57) ABSTRACT

The present invention is directed to compounds of formulae (I) and (II) wherein all substituents are defined herein, as well as pharmaceutically acceptable compositions comprising compounds of the invention and methods of using said compositions in the treatment of various disorders.

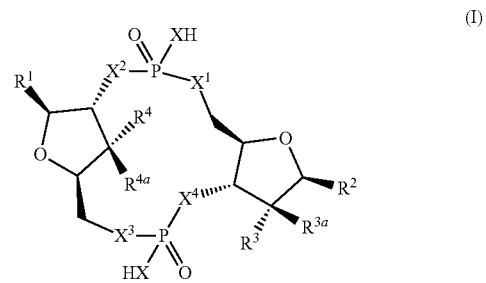

(I)

16 Claims, No Drawings
Specification includes a Sequence Listing.

SEQUENCE LISTING

<160> NUMBER OF SEQ ID NOS: 2

<210> SEQ ID NO 1
<211> LENGTH: 210

```
<212> TYPE: PRT
<213> ORGANISM: Artificial Sequence
<220> FEATURE:
<223> OTHER INFORMATION: Homosapien

<400> SEQUENCE: 1

Met Gly Ser Ser His His His His His Ser Ser Gly Glu Thr Val
1               5                   10                  15

Arg Phe Gln Gly His Met Ser Val Ala His Gly Leu Ala Trp Ser Tyr
                20                  25                  30

Tyr Ile Gly Tyr Leu Arg Leu Ile Leu Pro Glu Leu Gln Ala Arg Ile
            35                  40                  45

Arg Thr Tyr Asn Gln His Tyr Asn Asn Leu Leu Arg Gly Ala Val Ser
    50                  55                  60

Gln Arg Leu Tyr Ile Leu Leu Pro Leu Asp Cys Gly Val Pro Asp Asn
65                  70                  75                  80

Leu Ser Met Ala Asp Pro Asn Ile Arg Phe Leu Asp Lys Leu Pro Gln
                85                  90                  95

Gln Thr Gly Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
        115                 120                 125

Glu Tyr Ala Thr Pro Leu Gln Thr Leu Phe Ala Met Ser Gln Tyr Ser
130                 135                 140

Gln Ala Gly Phe Ser Arg Glu Asp Arg Leu Glu Gln Ala Lys Leu Phe
145                 150                 155                 160

Cys Arg Thr Leu Glu Asp Ile Leu Ala Asp Ala Pro Glu Ser Gln Asn
                165                 170                 175

Asn Cys Arg Leu Ile Ala Tyr Gln Glu Pro Ala Asp Asp Ser Ser Phe
            180                 185                 190

Ser Leu Ser Gln Glu Val Leu Arg His Leu Arg Gln Glu Glu Lys Glu
        195                 200                 205

Glu Val
210

<210> SEQ ID NO 2
<211> LENGTH: 210
<212> TYPE: PRT
<213> ORGANISM: Artificial Sequence
<220> FEATURE:
<223> OTHER INFORMATION: Homosapien

<400> SEQUENCE: 2

Met Gly Ser Ser His His His His His Ser Ser Gly Glu Thr Val
1               5                   10                  15

Arg Phe Gln Gly His Met Ser Val Ala His Gly Leu Ala Trp Ser Tyr
                20                  25                  30

Tyr Ile Gly Tyr Leu Arg Leu Ile Leu Pro Glu Leu Gln Ala Arg Ile
            35                  40                  45

Arg Thr Tyr Asn Gln His Tyr Asn Asn Leu Leu Arg Gly Ala Val Ser
    50                  55                  60

Gln Arg Leu Tyr Ile Leu Leu Pro Leu Asp Cys Gly Val Pro Asp Asn
65                  70                  75                  80

Leu Ser Met Ala Asp Pro Asn Ile Arg Phe Leu Asp Lys Leu Pro Gln
                85                  90                  95

Gln Thr Ala Asp Arg Ala Gly Ile Lys Asp Arg Val Tyr Ser Asn Ser
            100                 105                 110
```

| | | | | | | | | | | | | |
|---|---|---|---|---|---|---|---|---|---|---|---|---|
| Ile | Tyr | Glu | Leu | Leu | Glu | Asn | Gly | Gln | Arg | Ala | Gly | Thr | Cys | Val | Leu |
| | | 115 | | | | 120 | | | | 125 | | | | | |
| Glu | Tyr | Ala | Thr | Pro | Leu | Gln | Thr | Leu | Phe | Ala | Met | Ser | Gln | Tyr | Ser |
| 130 | | | | | 135 | | | | | 140 | | | | | |
| Gln | Ala | Gly | Phe | Ser | Arg | Glu | Asp | Arg | Leu | Glu | Gln | Ala | Lys | Leu | Phe |
| 145 | | | | | 150 | | | | | 155 | | | | | 160 |
| Cys | Gln | Thr | Leu | Glu | Asp | Ile | Leu | Ala | Asp | Ala | Pro | Glu | Ser | Gln | Asn |
| | | | 165 | | | | 170 | | | | | | 175 | | |
| Asn | Cys | Arg | Leu | Ile | Ala | Tyr | Gln | Glu | Pro | Ala | Asp | Asp | Ser | Ser | Phe |
| | | | 180 | | | | | 185 | | | | | 190 | | |
| Ser | Leu | Ser | Gln | Glu | Val | Leu | Arg | His | Leu | Arg | Gln | Glu | Glu | Lys | Glu |
| | | 195 | | | | | 200 | | | | | 205 | | | |
| Glu | Val | | | | | | | | | | | | | | |
| 210 | | | | | | | | | | | | | | | |

CYCLIC DINUCLEOTIDES AS ANTICANCER AGENTS

CROSS-REFERENCE TO RELATED APPLICATIONS

This application is a national phase application under 35 U.S.C. § 371 of International Patent Application No. PCT/US2019/021145, filed Mar. 7, 2019, which claims priority to U.S. Provisional Application Ser. 62/640,325, filed Mar. 8, 2018, the contents of which are specifically incorporated fully herein by reference.

FIELD OF THE INVENTION

The invention provides novel compounds, pharmaceutical compositions comprising the compounds, and methods of using them, for example, for the treatment or prophylaxis of certain cancers and to their use in therapy.

BACKGROUND OF THE INVENTION

Immunotherapy is a rapidly expanding area of medical treatment in which a patient's immune system is deliberately activated, suppressed or otherwise modulated for a positive therapeutic effect. Immunotherapy agents include such things as cells, antigens, antibodies, nucleic acids, proteins, peptides, naturally occurring ligands and synthetically prepared molecules. Cytokines are small glycoprotein molecules known for their role in causing immune response through complex signaling networks. Cytokines have been explored as immunotherapy agents but their direct administration is hampered by many factors including their short half-life in blood which can only be compensated with frequent and often high doses. One highly promising approach is cytokine induction in which the patient is treated with an immunomodulatory agent that triggers the production of one or more therapeutically beneficial cytokines in their body.

One agent in the production of cytokines is the adaptor protein STING (Simulator of INterferon Genes; also known as MPYS, TMEM173, MITA and ERIS). STING is an intracellular receptor situated on the endoplasmic reticulum. The binding to STING by an agonist activates a signaling pathway culminating in the induction of Type I IFNs, which are secreted and protect the secreting and nearby cells. STING can be activated by two different pathways, each involving a different type of cyclic dinucleotide ("CDN") agonist. In the first pathway, the agonist is an exogenous CDN used by bacterial pathogens as a second messenger (Burdette et al. 2013). In the second pathway the enzyme cyclic GMP-AMP synthase (cGAS) detects cytosolic DNA and, in response, synthesizes a CDN that functions as an endogenous STING agonist (Ablasser et al. 2013; Gao et al. 2013; Sun et al 2013).

Activation of STING results in up-regulation of IRF3 and NF-κB pathways leading to induction of Interferon-β and other cytokines. STING is crucial for responses to cytosolic DNA of pathogen or host origin.

Two exogenous bacterial STING agonist CDNs are 3'3'-cGAMP and c-GMP. The endogenous STING agonist CDN made by cGAS is 2'3'-cGAMP. The bacterial CDNs are characterized by two 3'5' phosphodiester bridges, while the cGAS-produced CDN is characterized by one 2'5' and one 3'5' phosphodiester bridge. As a shorthand, the former CDNs are referred to as 3'3' CDNs and the latter as 2'3' CDNs. For historical reasons, 3'3' CDNs also are referred to as the "canonical" form and 2'3' CDNs are referred to as the "non-canonical" form.

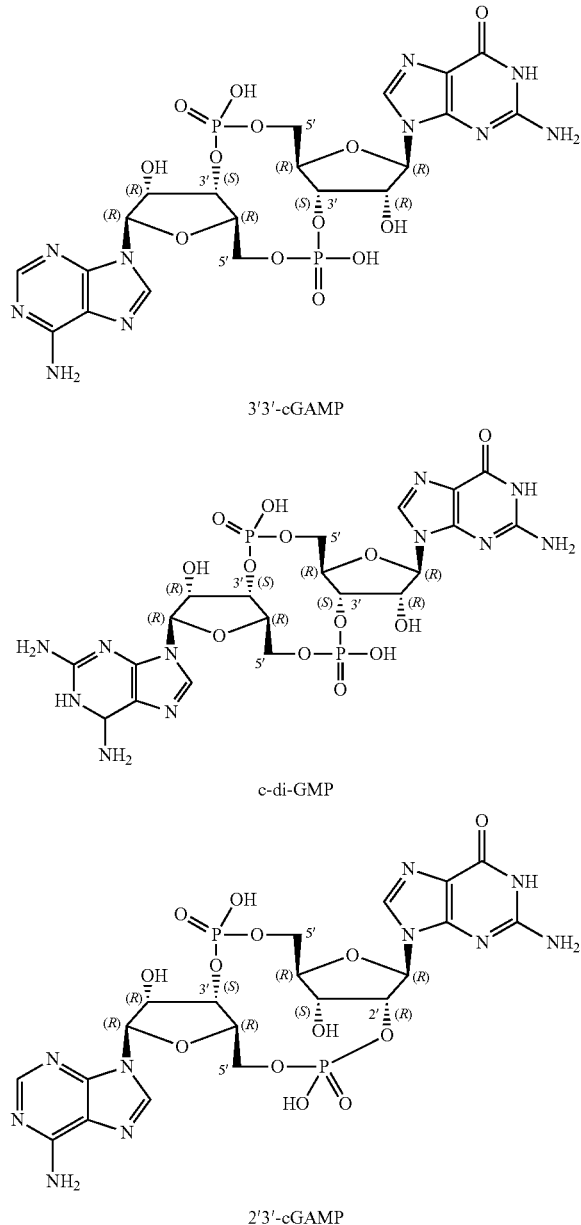

In addition to protecting an organism against pathogen infection, STING activation has also been reported to be beneficial in the treatment of inflammatory diseases and, in an area of particular current interest, cancer. Administration of a synthetic CDN in combination with the cancer vaccine STINGVAX demonstrated enhanced antitumor efficacy in multiple therapeutic models (Fu et al. 2015). Administration of STING agonists alone has been reported to show potent antitumor immune efficacy in a mouse model (Corrales et al. 2015a). For reviews on the role of STING in infection, inflammation, and/or cancer, see Ahn et al. 2015; Corrales et al. 2015b and 2016; and Barber 2015.

The present invention, therefore, provides novel cyclic dinucleotides which may be useful for the treatment of cancer.

SUMMARY OF THE INVENTION

There are provided compounds of formula (I)

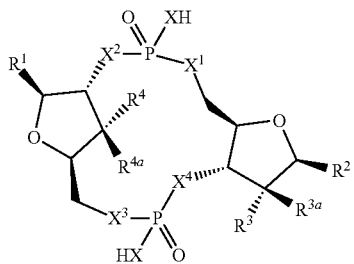
(I)

wherein
X is independently O or S;
$X^1$, $X^2$, $X^3$ and $X^4$ are each independently O or NH;
$R^1$ and $R^2$ are independently

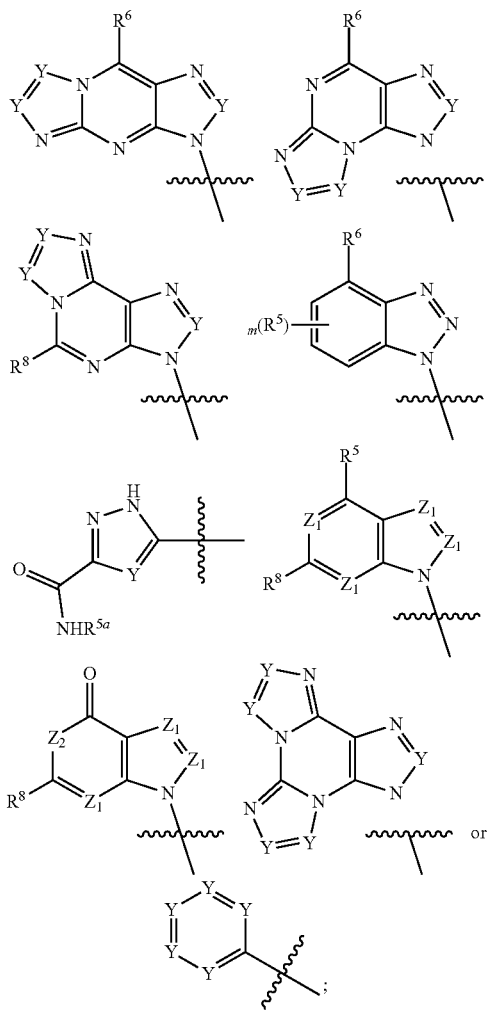

with the proviso that one of $R^1$ and $R^2$ must be

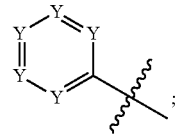

each $Z^1$ is independently N or $CR^a$;
$Z^2$ is $NR^b$;
$R^a$ is H, halogen, $C_{1-6}$alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H $C_{1-6}$ alkyl substituted with 0-6$R^5$, $C_{3-6}$cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$alkyl or $C_{3-6}$ cycloalkyl;
$R^3$ and $R^4$ are independently H, $CH_3$, halogen, —$NR^{a1}R^{a1}$— or $OR^{a1}$;
$R^{3a}$ and $R^{4a}$ are independently H, $CH_3$, halogen, —$NR^{a1}R^{a1}$ or $OR^{a1}$; or
$R^3$ and $R^{3a}$ or $R^4$ and $R^{4a}$ may dependently betaken together to form a 3-4 membered carbocycle; or
$R^3$ and $R^{3a}$ or $R^4$ and $R^{4a}$ may independently be taken together to form a C=$CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
each Y is independently $CR^a$ or N;
m is 0, 1, 2 or 3;
or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a method of treating cancer which comprises administering to a subject in need thereof a therapeutically effective amount of an activator of STING (of Formula I).

DETAILED DESCRIPTION OF THE INVENTION

In a first aspect of the invention, there is provided a compound of formula (I)

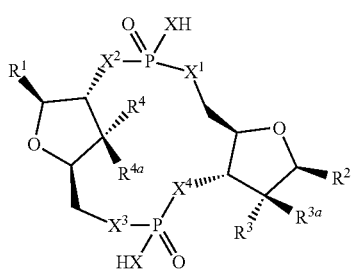
(I)

wherein

X is independently O or S;

$X^1$, $X^2$, $X^3$ and $X^4$ are each independently O or NH;

$R^1$ and $R^2$ are independently

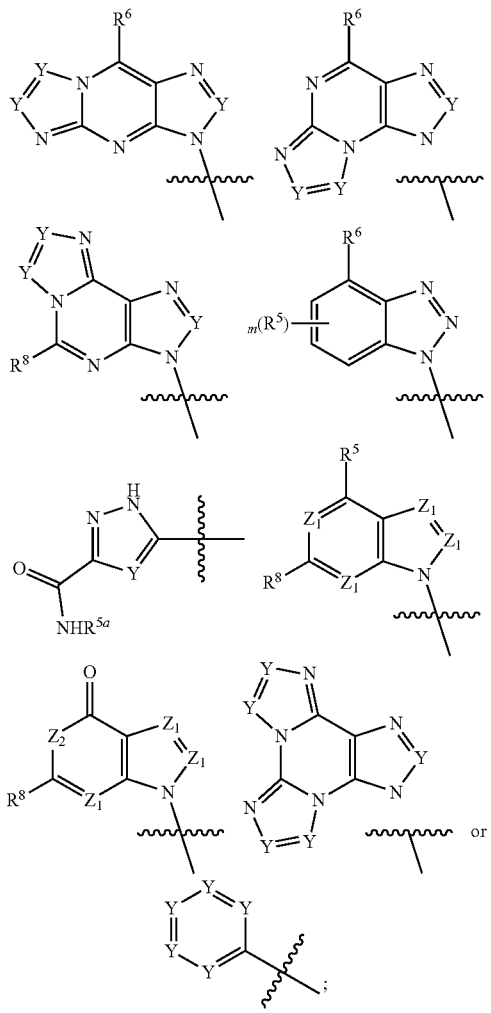

with the proviso that one of $R^1$ and $R^2$ must be

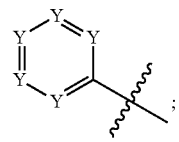

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, —$NR^{a1}R^{a1}$ or $OR^{a1}$;

$R^{3a}$ and $R^{4a}$ are independently H, $CH_3$, halogen, —$NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In a second aspect of the invention, there is provided a compound of formula (I) wherein $R^1$ is

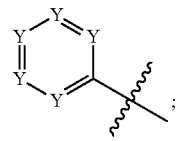

and
R² is
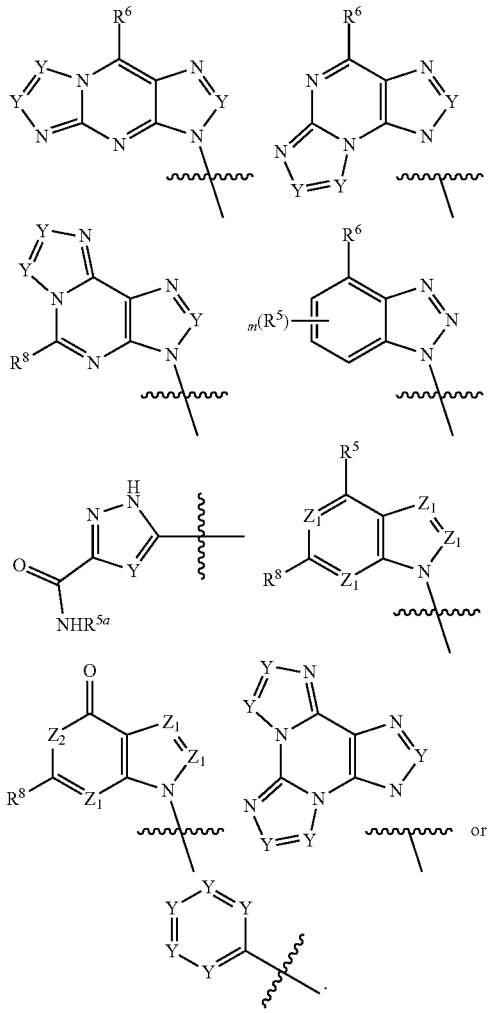
In a third aspect of the invention, there is provided a compound of formula (I) wherein
R¹ is
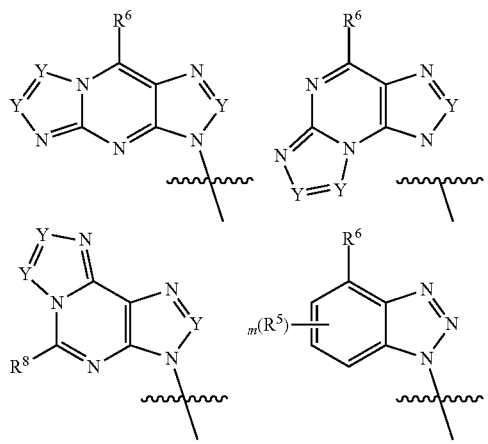
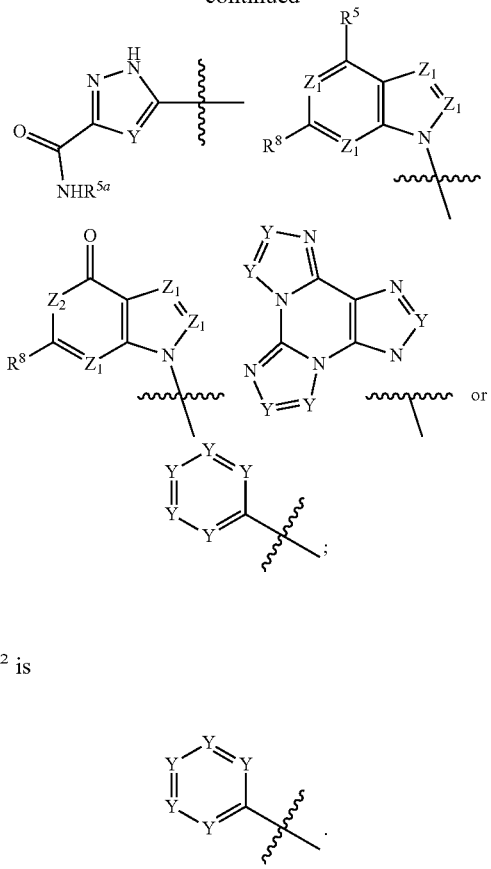
and
R² is
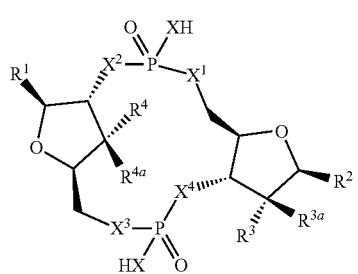
In a 4th aspect of the invention, there is provided a compound of formula (I) wherein
$$\text{(I)}$$
wherein
X is S;
$X^1$, $X^2$, $X^3$ and $X^4$ are each independently O or NH;
R¹ and R² are independently
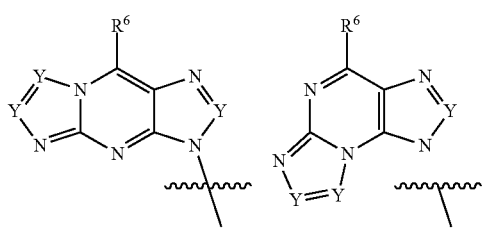

-continued

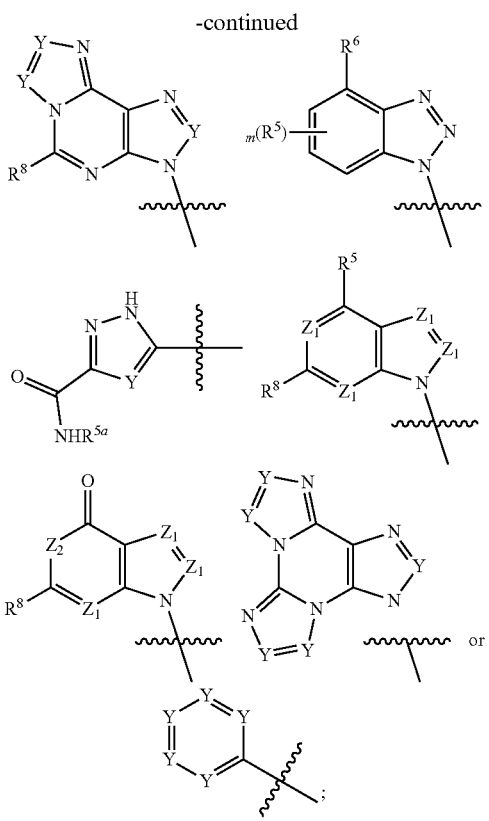

with the proviso that one of $R^1$ and $R^2$ must be

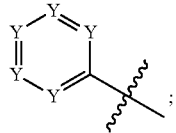

each $Z^1$ is independently N or $CR^a$;
$Z^2$ is $NR^b$;
$R^a$ is H, halogen, $C_{1-6}$ alkyl substituted with 0-6 $R^5$, $C_{3-6}$cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ and $R^4$ are independently H, $CH_3$, halogen, —$NR^{a1}R^{a1}$ or $OR^{a1}$;
$R^{3a}$ and $R^{4a}$ are independently H, $CH_3$, halogen, —$NR^{a1}R^{a1}$ or $OR^{a1}$; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a $C=CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^1$, —OC(O)$R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^1$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R'$ or $S(O)_2NR^{a1}R^{a1}$;

each Y is independently $CR^a$ or N;
m is 0, 1, 2 or 3;
or a pharmaceutically acceptable salt, tautomer or stereoisomer thereof.

In a fifth aspect of the invention, there is provided a compound of formula (I)

(I)

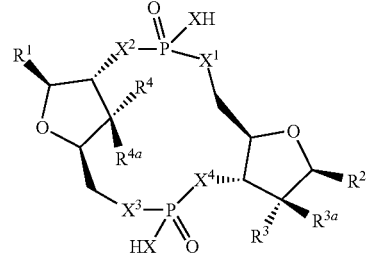

wherein
X is O;
$X^1$, $X^2$, $X^3$ and $X^4$ are each independently O or NH;
$R^1$ and $R^2$ are independently

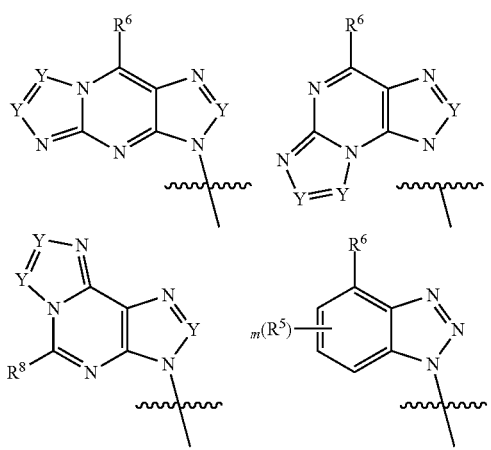

-continued

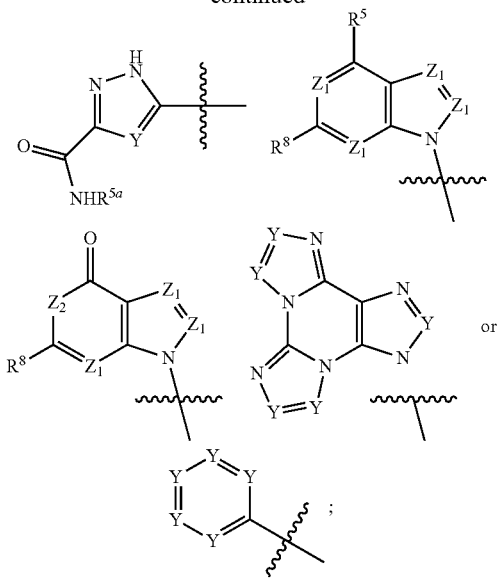

with the proviso that one of $R^1$ and $R^2$ must be

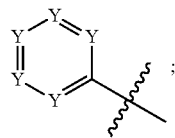

each $Z^1$ is independently N or $CR^a$;
$Z^2$ is $NR^b$;
$R^a$ is H, halogen, $C_{1-6}$alkyl substituted with 0-6 $R^5$, $C_{3-6}$cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$alkyl substituted with 0-6R, $C_3$, cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$cycloalkyl;
$R^3$ and $R^4$ are independently H, $CH_3$, halogen, —$NR^{a1}R^{a1}$ or $OR^{a1}$;
$R^{3a}$ and $R^{4a}$ are independently H, $CH_3$, halogen, —$NR^{a1}R^{a1}$ or $OR^{a1}$; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a C=$CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^3$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^5$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$ each Y is independently $CR^a$ or N;

m is 0, 1, 2 or 3;

or a pharmaceutically acceptable salt, tautomer or stereoisomer thereof.

In a sixth aspect of the invention, there is provided a compound of the formula

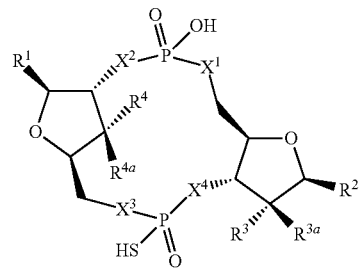

wherein
$X^1$, $X^2$, $X^3$ and $X^4$ are each independently O or NH;
$R^1$ and $R^2$ are independently

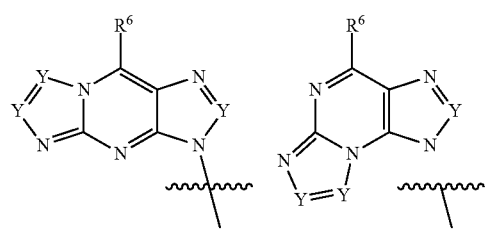

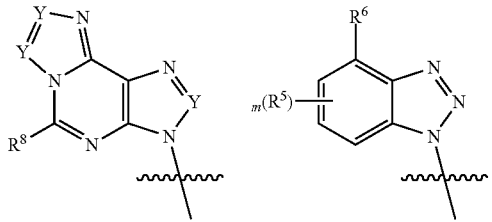

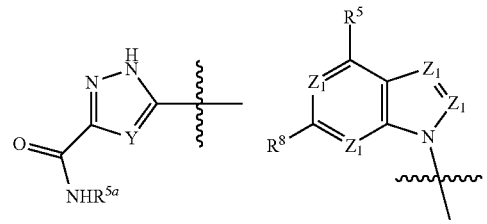

-continued

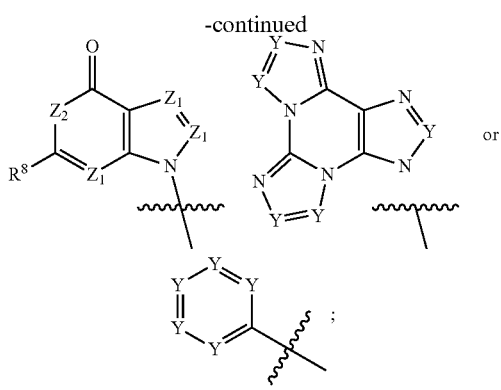

with the proviso that one of $R^1$ and $R^2$ must be

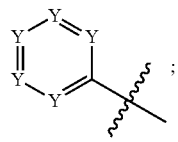

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ and $R^4$ are independently H, $CH_3$, halogen, —$NR^{a1}R^{a1}$ or $OR^{a1}$;
$R^{3a}$ and $R^{4a}$ are independently H, $CH_3$, halogen, —$NR^{a1}R^{a1}$ or $OR^{a1}$; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a C=$CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6$R^5$;
$R^6$ is H, halogen, $C_{1-3}$ alkyl substituted with 0-6 $R^5$, CN, $NO_2$, OH $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

each Y is independently $CR^a$ or N;
m is 0, 1, 2 or 3;
or a pharmaceutically acceptable salt, tautomer or stereoisomer thereof.

In a seventh aspect of the invention, there is provided a compound of the formula

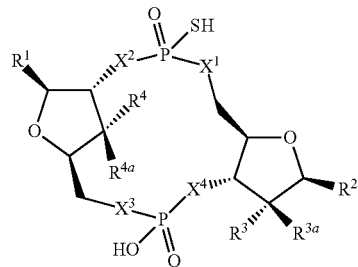

wherein
$X^1$, $X^2$, $X^3$ and $X^4$ are each independently O or NH;
$R^1$ and $R^2$ are independently

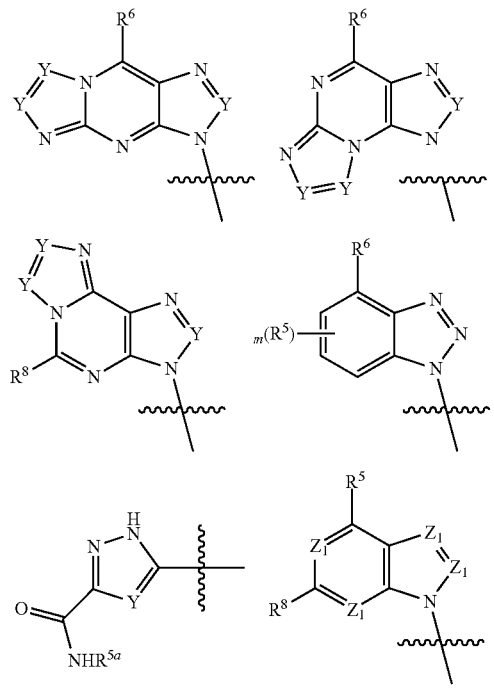

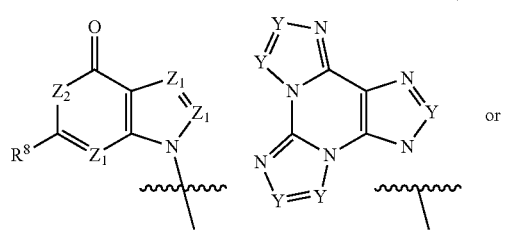

-continued

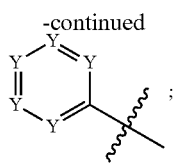

with the proviso that one of $R^1$ and $R^2$ must be

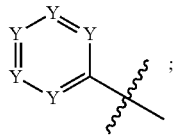

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ and $R^4$ are independently H, $CH_3$, halogen, —$NR^{a1}R^{a1}$ or $OR^{a1}$;
$R^{3a}$ and $R^{4a}$ are independently H, $CH_3$, halogen, —$NR^{a1}R^{a1}$ or $OR^{a1}$; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a $C=CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
each Y is independently $CR^a$ or N;
m is 0, 1, 2 or 3;
or a pharmaceutically acceptable salt, tautomer or stereoisomer thereof.

In an 8th aspect of the invention, there is provided a compound of the formula

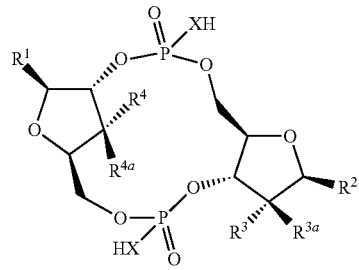

wherein
X is independently O or S;
$R^1$ and $R^2$ are independently

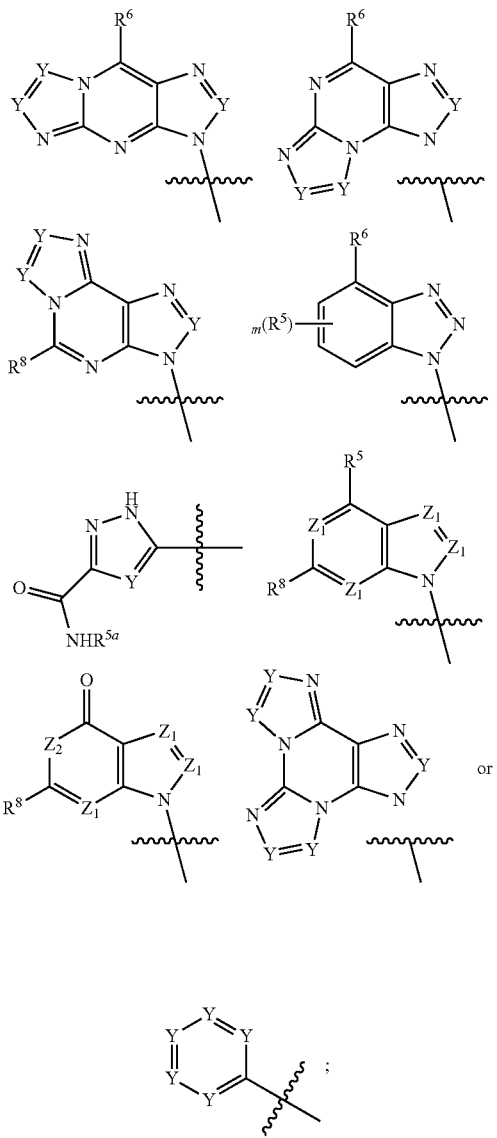

with the proviso that one of $R^1$ and $R^2$ must be

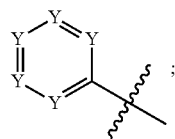

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $—C(O)R^{a1}$, $—C(O)NR^{a1}R^{a1}$, $—S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, $—NR^{a1}R^{a1}$ or $OR^{a1}$;

$R^{3a}$ and $R^{4a}$ are independently H, $CH_3$, halogen, $—NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In a ninth aspect of the invention, there is provided a compound of the formula

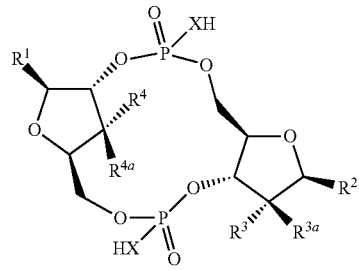

wherein

X is S;

$R^1$ and $R^2$ are independently

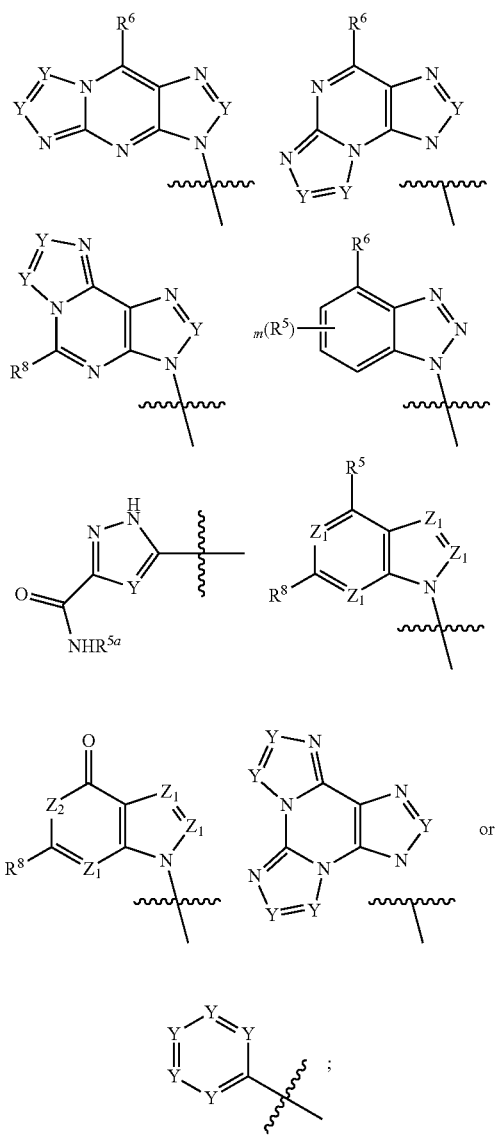

with the proviso that one of $R^1$ and $R^2$ must be

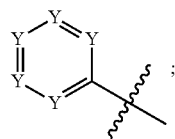

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, —$NR^{a1}R^{a1}$ or $OR^{a1}$;

$R^{3a}$ and $R^{4a}$ are independently H, $CH_3$, halogen, —$NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In a tenth aspect of the invention, there is provided a compound of the formula

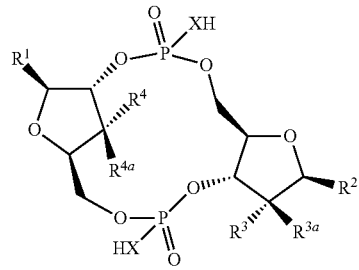

wherein

X is O;

$R^1$ and $R^2$ are independently

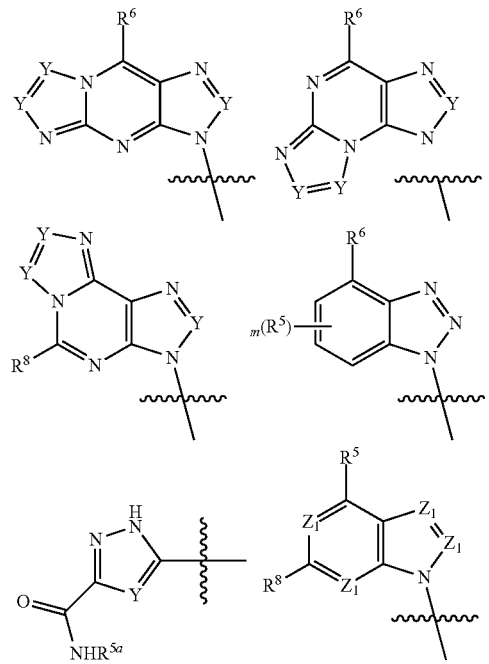

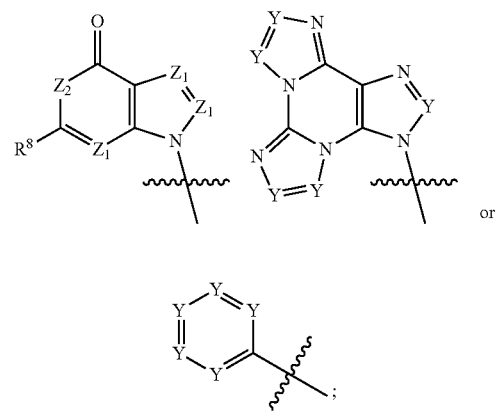

or with the proviso that one of $R^1$ and $R^2$ must be

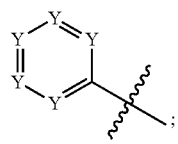

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, —$NR^{a1}R^{a1}$ or $OR^{a1}$;

$R^{3a}$ and $R^{4a}$ are independently H, $CH_3$, halogen, —$NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

each Y is independently $CR^a$ or N;

m is 0, 1, 2 or 3;

or a pharmaceutically acceptable salt, tautomer or stereoisomer thereof.

In an 11th aspect of the invention, there is provided a compound of the formula

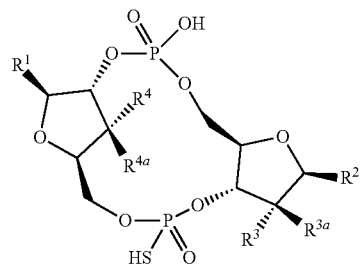

wherein $R^1$ and $R^2$ are independently

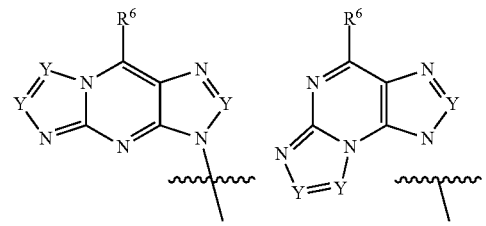

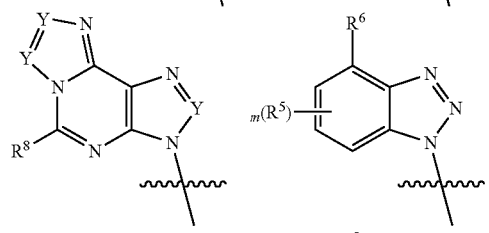

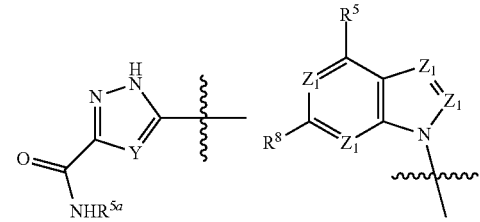

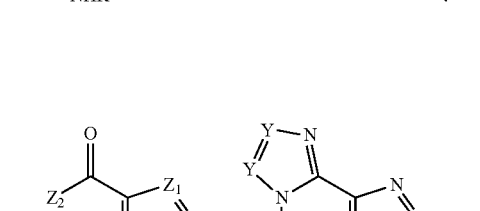

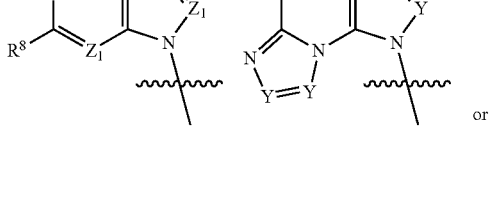

or

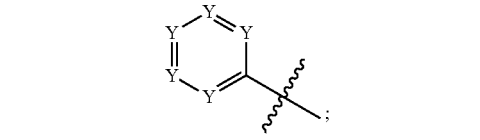

with the proviso that one of $R^1$ and $R^2$ must be

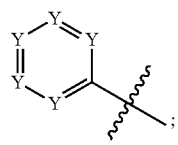

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$; $R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, $-NR^{a1}R^{a1}$ or $OR^{a1}$;

$R^{3a}$ and $R^{4a}$ are independently H, $CH_3$, halogen, $-NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In a 12th aspect of the invention, there is provided a compound of the formula

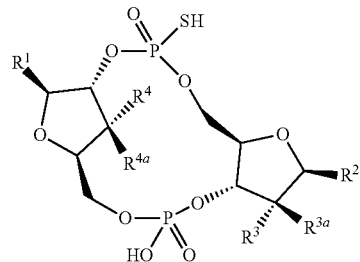

wherein
$R^1$ and $R^2$ are independently

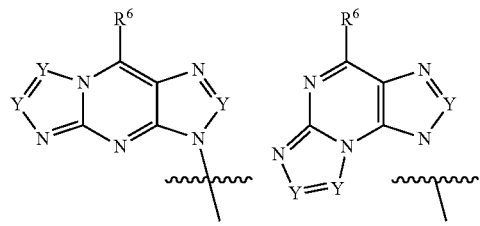

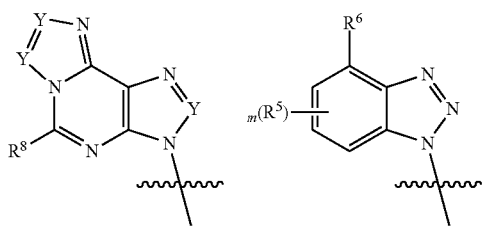

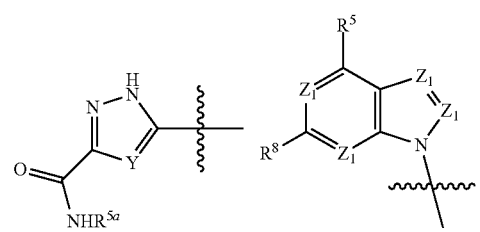

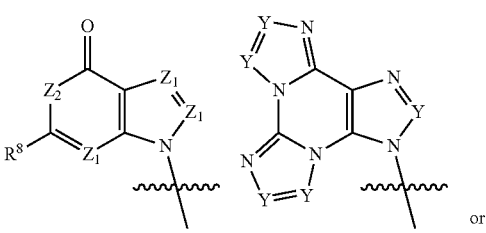

or

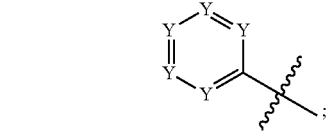

;

with the proviso that one of $R^1$ and $R^2$ must be

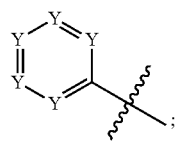

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^1$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, $-NR^{a1}R^{a1}$ or $OR^{a1}$;

$R^{3a}$ and $R^{4a}$ are independently H, $CH_3$, halogen, $-NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In a 13th aspect of the invention, there is provided a compound of the formula

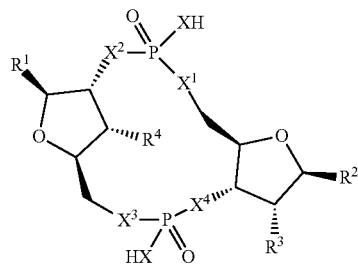

wherein

X is independently O or S;

$X^1$, $X^2$, $X^3$ and $X^4$ are each independently O or NH;

$R^1$ and $R^2$ are independently

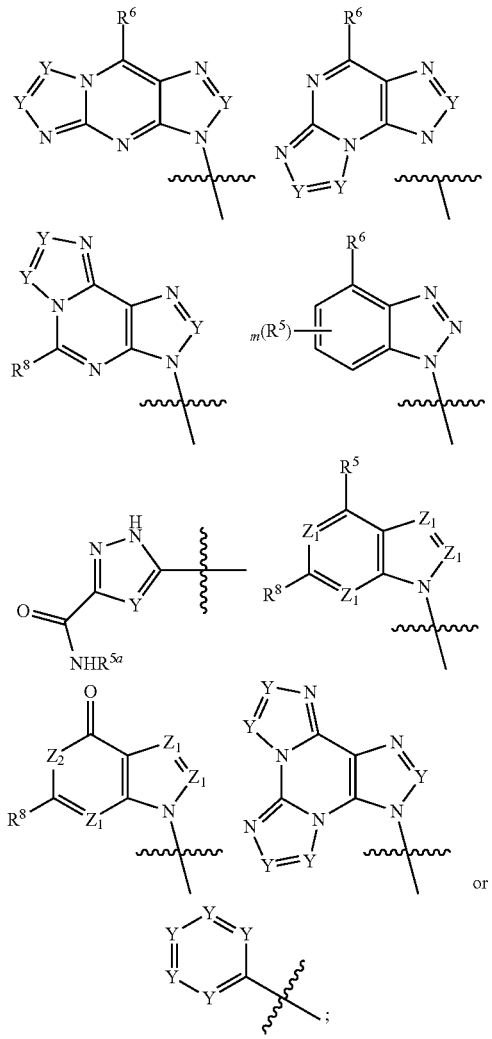

or with the proviso that one of R$^1$ and R$^2$ must be

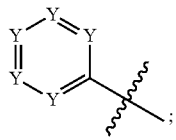

each Z$^1$ is independently N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R$^1$, C$_{3-6}$ cycloalkyl substituted with 0-6 R$^1$, —C(O)R$^{a1}$, —C(O)NR$^{a1}$R$^{a1}$, —S(O)$_2$R$^{a1}$ or S(O)$_2$NR$^{a1}$R$^{a1}$;
R$^{a1}$ is H, C$_{1-3}$ alkyl or C$_{3-6}$ cycloalkyl;
R$^3$ and R$^4$ are independently H, CH$_3$, halogen, —NR$^{a1}$R$^{a1}$ or OR$^{a1}$;
R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^{5a}$ is H or C$_{1-3}$ alkyl substituted with 0-6 R$^5$;
R$^6$ is H, halogen, C$_{1-3}$ alkyl substituted with 0-6 R$^5$, CN, NO$_2$, OH, OR$^a$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
each Y is independently CR$^a$ or N;
m is 0, 1, 2 or 3;
or a pharmaceutically acceptable salt, tautomer or stereoisomer thereof.

In a 14$^{th}$ aspect of the invention, there is provided a compound of the formula

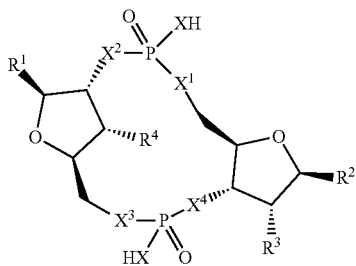

(I)

wherein
X is S;
X$^1$, X$^2$, X$^3$ and X$^4$ are each independently O or NH;
R$^1$ and R$^2$ are independently

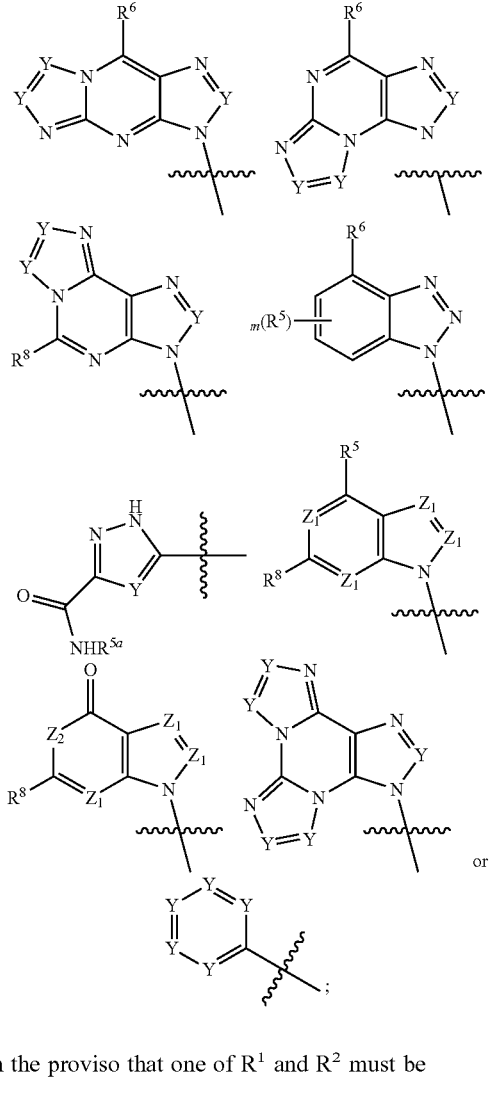

with the proviso that one of R$^1$ and R$^2$ must be

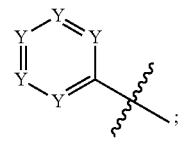

each Z$^1$ is independently N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SRI, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H, $C_{1-3}$ alkyl or $C_{3-6}$ cycloalkyl;

$R^3$ and $R^4$ are independently H, $CH_3$, halogen, $-NR^{a1}R^{a1}$ or $OR^{a1}$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R$, $-OC(O)NR^{a1}R^{a1}$, $-NR^{a1}R^{a1}$, $-NR\,C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^1$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In a 15th aspect of the invention, there is provided a compound of the formula

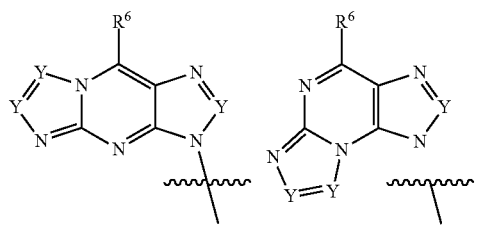

(I)

wherein

X is O;

$X^1$, $X^2$, $X^3$ and $X^4$ are each independently O or NH;

$R^1$ and $R^2$ are independently

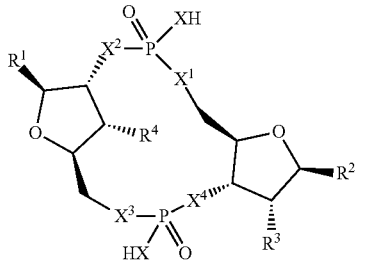

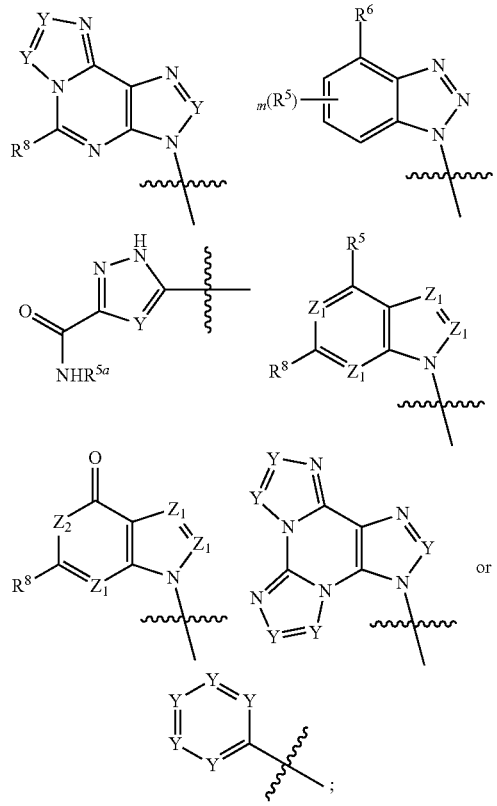

with the proviso that one of $R^1$ and $R^2$ must be

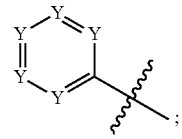

;

each $Z^1$ is independently N or $CR^a$;

$Z^2$ is $NR^b$;

$R^a$ is H, halogen, $C_{1-6}$ alkyl substituted with 0-6 $R^1$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$; $R^{a1}$ is H, $C_{1-3}$ alkyl or $C_{3-6}$ cycloalkyl;

$R^3$ and $R^4$ are independently H, $CH_3$, halogen, $-NR^{a1}R^{a1}$ or $OR^{a1}$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In a 16$^{th}$ aspect of the invention, there is provided a compound of the formula

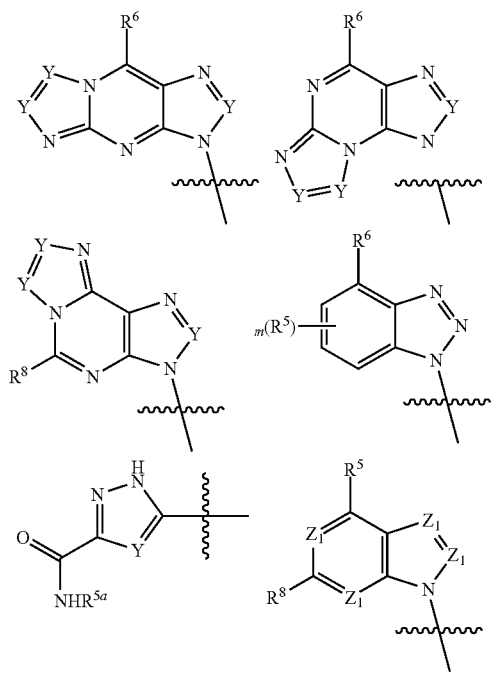

(I)

wherein
$X^1$, $X^2$, $X^3$ and $X^4$ are each independently O or NH;
$R^1$ and $R^2$ independently

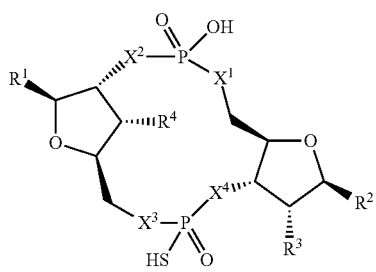

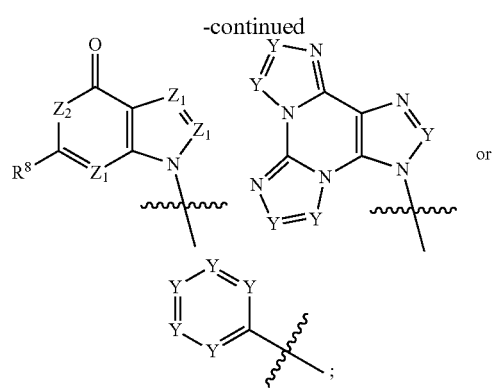

or with the proviso that one of $R^1$ and $R^2$ must be

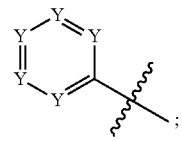

;

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^a$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, —$NR^{a1}R^{a1}$ or $OR^{a1}$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)Rat$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently $CR^a$ or N;
m is 0, 1, 2 or 3;
or a pharmaceutically acceptable salt, tautomer or stereoisomer thereof.

In a 17th aspect of the invention, there is provided a compound of the formula

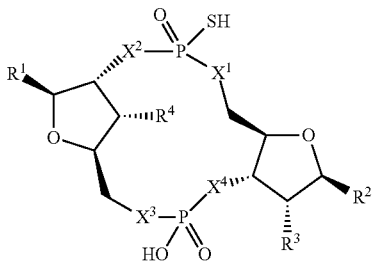
(I)

wherein

X¹, X², X³ and X⁴ are each independently O or NH:
R¹ and R² are independently

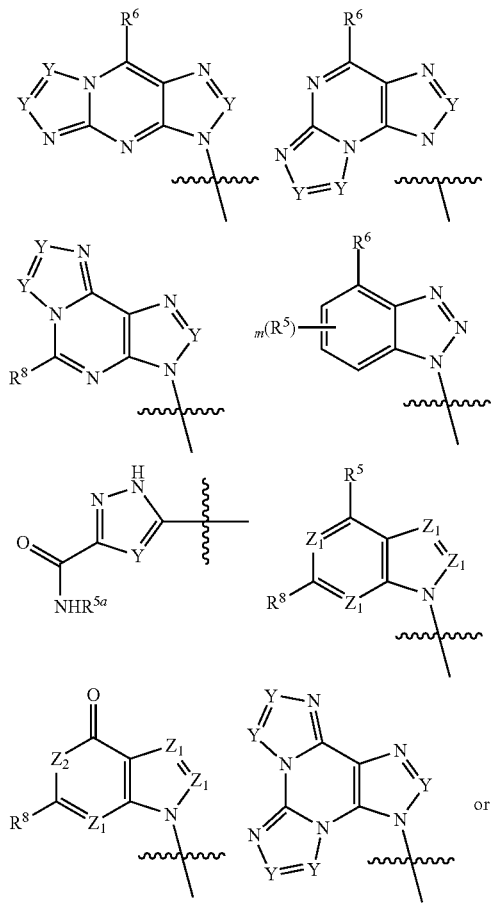

or

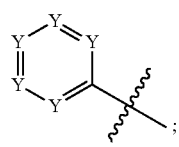

with the proviso that one of R¹ and R² must be

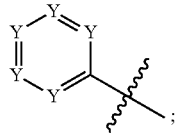

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, SRI, —C(O)$NR^{a1}R^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$;
$R^{a1}$ is H, $C_{1-3}$ alkyl or $C_{3-6}$ cycloalkyl;
$R^3$ and $R^4$ are independently H, $CH_3$, halogen, —NR$^{a1}$R$^{a1}$ or OR$^{a1}$;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, OR$^{a1}$, SR$^{a1}$, —C(O)NR$^{a1}$R$^{a1}$, —COOR$^{a1}$, —OC(O)R, —OC(O)NR$^{a1}$R$^{a1}$, —NR$^{a1}$R$^{a1}$, —NR C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, OR$^1$, SR$^{a1}$, —C(O)NR$^{a1}$R$^{a1}$, —COOR$^{a1}$, —OC(O)R$^{a1}$, —OC(O)NR$^{a1}$R$^{a1}$, NR$^{a1}$R$^a$, —NR$^{a1}$C(O)R$^1$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^8$ is H, halogen, $C_{1-3}$ alkyl substituted with 0-6 $R^5$, CN, $NO_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
each Y is independently $CR^a$ or N;
m is 0, 1, 2 or 3;
or a pharmaceutically acceptable salt, tautomer or stereoisomer thereof.

In an 18th aspect of the invention, there is provided a compound of the formula

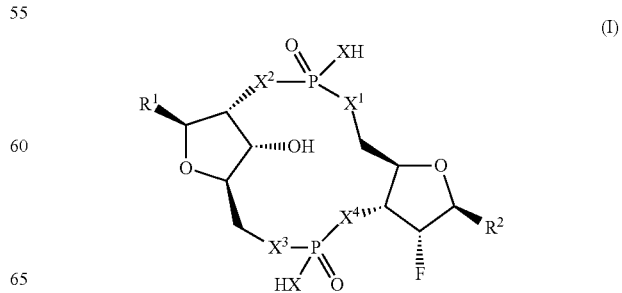
(I)

wherein
X is S;
$X^1$, $X^2$, $X^3$ and $X^4$ are each independently O or NH;
$R^1$ and $R^2$ are independently

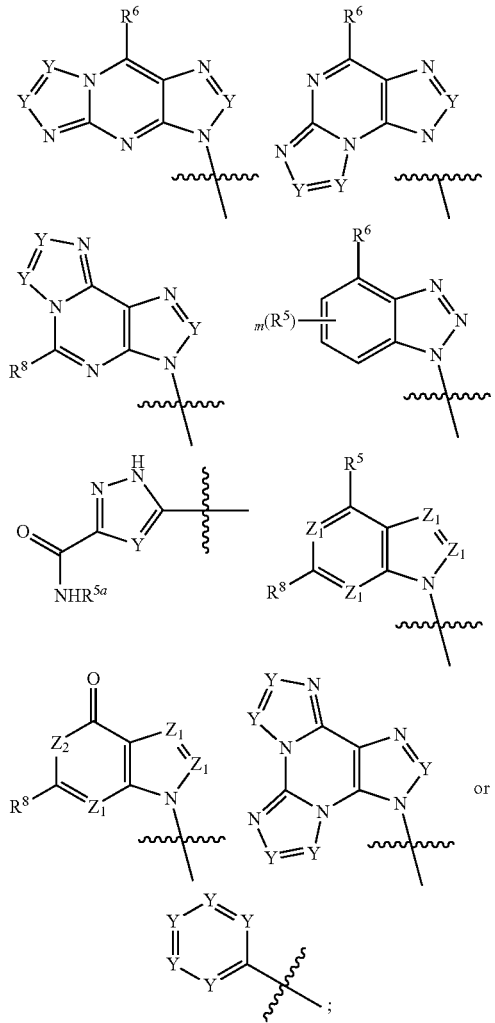

with the proviso that one of $R^1$ and $R^2$ must be

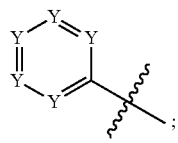

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$; Re is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^1R^{a1}$, —$S(O)R^{a1}$, —$S(O)NR^{a1}R^{a1}$, —$S(O)_2R^{a1}$ or $S(O)_2NR^{a1}R^{a1}$;
each Y is independently $CR^a$ or N;
m is 0, 1, 2 or 3;
or a pharmaceutically acceptable salt, tautomer or stereoisomer thereof.

In a 19$^{th}$ aspect of the invention, there is provided a compound of the formula

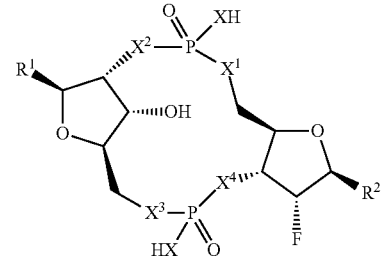

wherein
X is O;
$X^1$, $X^2$, $X^3$ and $X^4$ are each independently O or NH;
$R^1$ and $R^2$ are independently

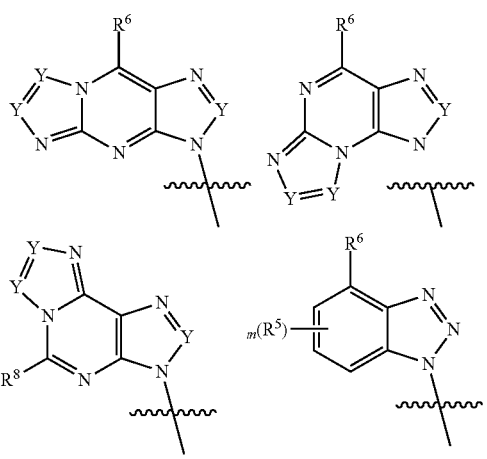

-continued

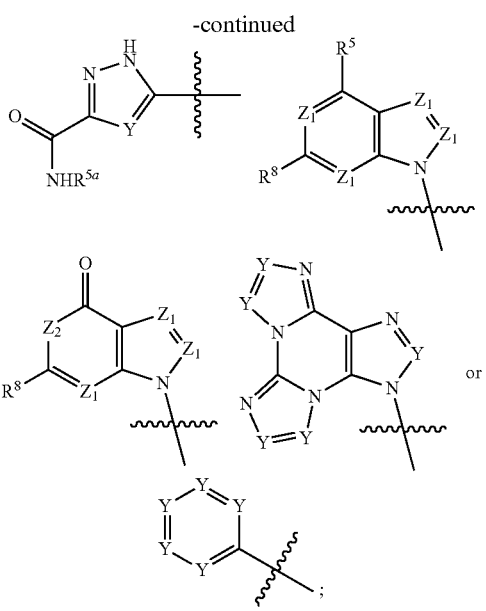

with proviso that one of $R^1$ and $R^2$ must be

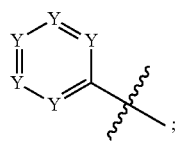
;

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^1$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
each Y is independently $CR^a$ or N;
m is 0, 1, 2 or 3;
or a pharmaceutically acceptable salt, tautomer or stereoisomer thereof.

In a 20th aspect of the invention, there is provided a compound of the formula

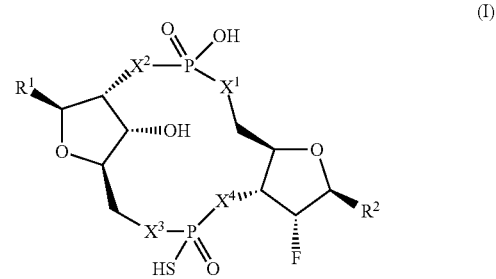

(I)

wherein
$X^1$, $X^2$, $X^3$ and $X^4$ are each independently O or NH:
$R^1$ and $R^2$ are independently

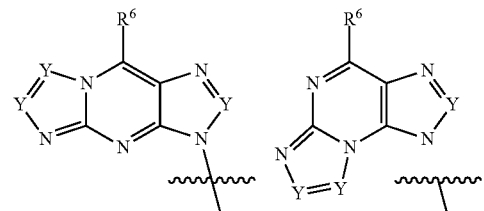

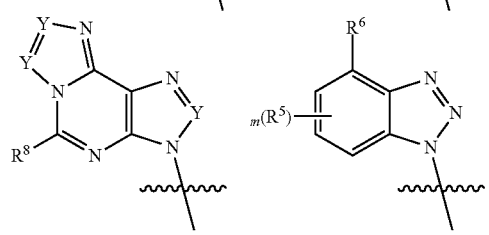

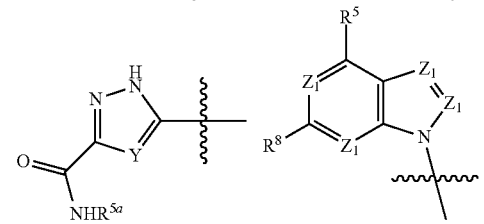

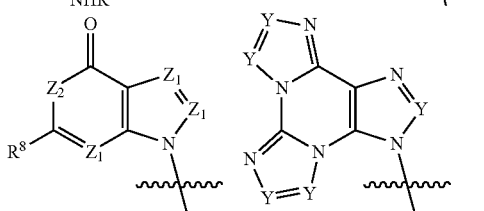

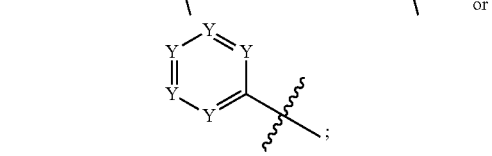

with the proviso that one of R¹ and R² must be

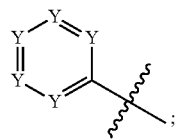

each Z¹ is independently N or CR$^a$;
Z² is NR$^b$;
R$^a$ is H, halogen, C$_{1-6}$alkyl substituted with 0-6 R⁵, C$_{3-6}$cycloalkyl substituted with 0-6 R$^{a1}$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R⁵, C$_{3-6}$cycloalkyl substituted with 0-6 R⁵, —C(O)R$^{a1}$, —C(O)NR$^{a1}$R$^{a1}$, —S(O)$_2$R$^{a1}$ or S(O)$_2$NR$^{a1}$R$^{a1}$;
R$^{a1}$ is H, C$_{1-3}$ alkyl or C$_{3-6}$cycloalkyl;
R⁵ is H, halogen, C$_{1-3}$ alkyl substituted with 0-6 R$^a$, C$_{3-6}$cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^{5a}$ is H or C$_{1-3}$ alkyl substituted with 0-6 R⁵;
R⁶ is H, halogen, C$_{1-3}$ alkyl substituted with 0-6 R⁵, CN, NO$_2$, OH, OR, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)Rat, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R⁸ is H, halogen, C$_{1-3}$ alkyl substituted with 0-6 R⁵, CN, NO$_2$, OH, OR, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R' or S(O)$_2$NR$^{a1}$R$^{a1}$;
each Y is independently CR$^a$ or N;
m is 0, 1, 2 or 3;
or a pharmaceutically acceptable salt, tautomer or stereoisomer thereof.

In a 21st aspect of the invention, there is provided a compound of the formula

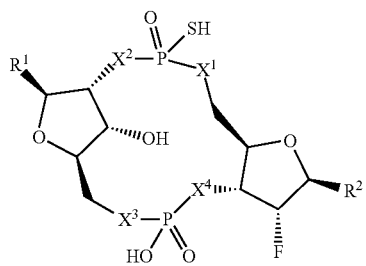

(I)

wherein
X¹, X², X³ and X⁴ are each independently O or NH;
R¹ and R² are independently

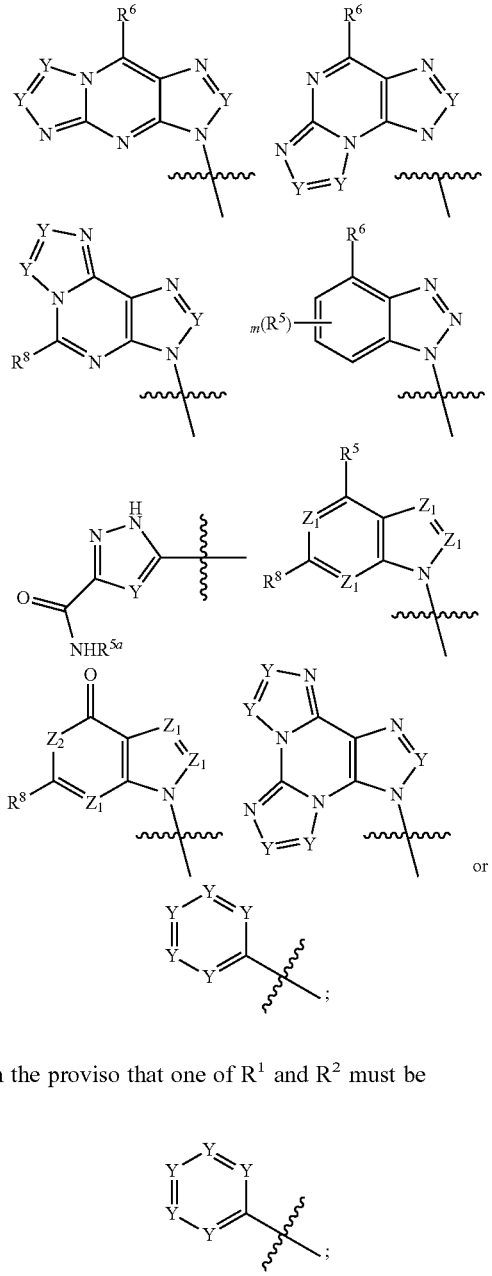

with the proviso that one of R¹ and R² must be

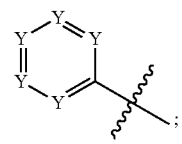

each Z¹ is independently N or CR$^a$;
Z² is NR$^b$;
R$^a$ is H, halogen, C$_{1-6}$alkyl substituted with 0-6 R⁵, C$_{3-6}$cycloalkyl substituted with 0-6 R⁵, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$; R$^b$ is H, C$_{1-6}$alkyl substituted with 0-6 R⁵, C$_{3-6}$cycloalkyl substituted with 0-6 R⁵, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H, $C_{1-3}$ alkyl or $C_{3-6}$ cycloalkyl;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, NO$_2$, OH, OR, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H halogen, $C_{1-3}$ alkyl substituted with 0-6 $R^5$, CN, NO$_2$, OH, OR$^{a1}$ SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently CR$^a$ or N;

m is 0, 1, 2 or 3;

or a pharmaceutically acceptable salt, tautomer or stereoisomer thereof.

In the 22nd aspect of the invention, there is provided a compound of the formula

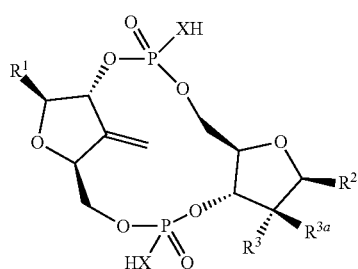

(I)

wherein

X is independently O or S;

$R^1$ and $R^2$ are independently

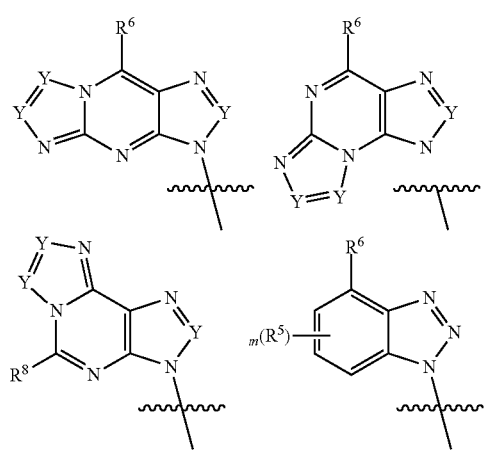

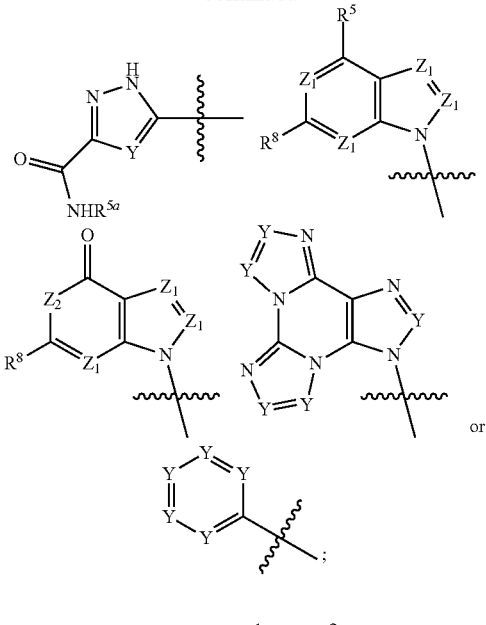

with the proviso that one of $R^1$ and $R^2$ must be

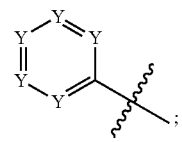

;

each $Z^1$ is independently N or CR$^a$;

$Z^2$ is NR$^b$;

$R^a$ is H, halogen, $C_{1-6}$ alkyl substituted with 0-6 $R^5$, $C_{3-6}$ cycloalkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, $C_{1-6}$ alkyl substituted with 0-6 $R^1$, $C_{3-6}$ cycloalkyl substituted with 0-6 $R^1$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H, $C_{1-3}$ alkyl or $C_{3-6}$ cycloalkyl;

$R^3$ is H, CH$_3$, halogen, —NR$^{a1}$R$^{a1}$ or OR$^{a1}$;

$R^{3a}$ is H, CH$_3$, halogen, —NR$^{a1}$R$^{a1}$ or OR$^{a1}$; or $R^3$ and $R^{3a}$ may be taken together to form a 3-4 membered carbocycle; or $R^3$ and $R^{3a}$ may be taken together to form a C=CH$_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)

$NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H halogen, $C_{1-3}$ alkyl substituted with 0-6 $R^5$, CN, $NO_2$, OH, $OR^{a1}$ $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$ each Y is independently $CR^a$ or N;

m is 0, 1, 2 or 3;

or a pharmaceutically acceptable salt, tautomer or stereoisomer thereof.

In the 23rd aspect of the invention, there is provided a compound of the formula

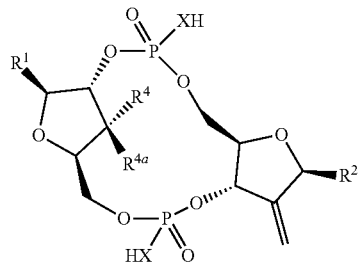

wherein

X is independently O or S;

$R^1$ and $R^2$ are independently

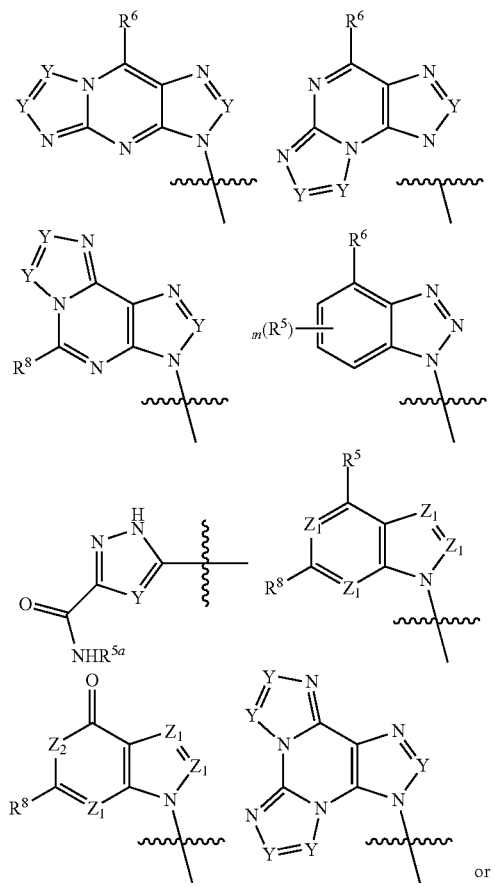

or

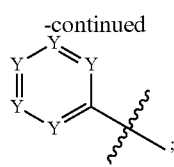

with the proviso that one of $R^1$ and $R^2$ must be

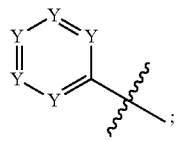

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^1$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$; $R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

In the 24th aspect of the invention, there is provided a compound of the formula

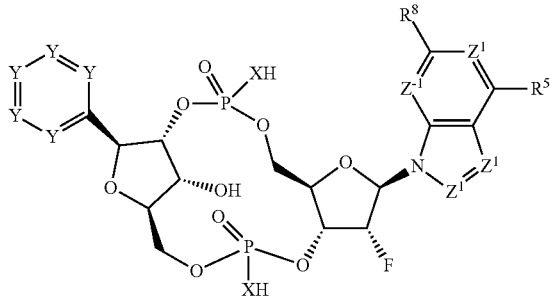

wherein
X is independently O or S;
each $Z^1$ is independently N or $CR^a$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, SR, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —OC(O)$R^{a1}$, —$OC(O)NR^{a1}R^{a1}$, —$NR^{a1}R^{a1}$, —$NR^{a1}C(O)R$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{31}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O) NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
each Y is independently $CR^a$ or N;
or a pharmaceutically acceptable salt, tautomer or stereoisomer thereof.

In the 25th aspect of the invention, there is provided a compound of the formula

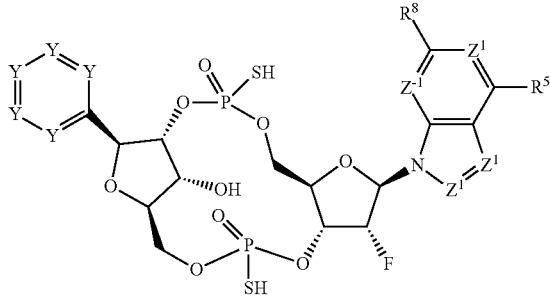

wherein
each $Z^1$ is independently N or $CR^a$;
$R^a$ is H, halogen, $C_{1-6}$ alkyl substituted with 0-6 $R^5$, $C_{3-6}$ cycloalkyl substituted with 0-6 $R^5$, CN. $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^5$ is H, halogen, $C_{1-3}$ alkyl substituted with 0-6 $R^a$, $C_{3-6}$ cycloalkyl substituted with 0-6 $R^{a1}$, aryl substituted with 0-6 $R^a$ or heteroaryl substituted with 0-6 $R^a$, CN. $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
each Y is independently $CR^a$ or N;
or a pharmaceutically acceptable salt, tautomer or stereoisomer thereof.

In a 26th aspect of the invention, there is provided a compound of the formula

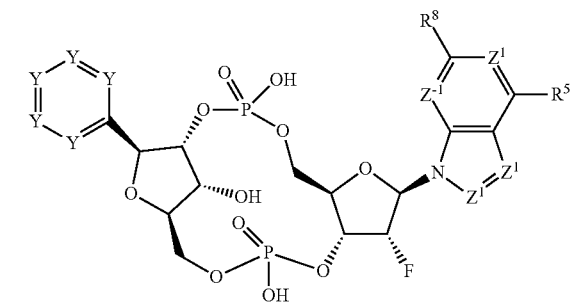

wherein
each $Z^1$ is independently Nor $CR^a$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$; $R^a$ is H, $C_{1-3}$ alkyl or $C_{3-6}$ cycloalkyl;
$R^5$ is H, halogen, $C_{1-3}$ alkyl substituted with 0-6 $R^a$, $C_{3-6}$ cycloalkyl substituted with 0-6 $R^{a1}$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, OR, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently CR$^a$ or N;

or a pharmaceutically acceptable salt, tautomer or stereoisomer thereof.

In a 27th aspect of the invention, there is provided a compound of the formula

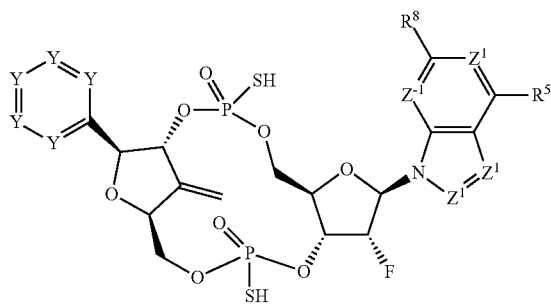

wherein each Z$^1$ is independently N or CR$^a$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{31}$, —S(O)R$^{a1}$, —S(O)NR$^{a1}$R$^{a1}$, —S(O)$_2$R$^{a1}$ or S(O)NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^1$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently CR$^a$ or N;

or a pharmaceutically acceptable salt, tautomer or stereoisomer thereof.

In a 28th aspect of the invention, there is provided a compound of the formula

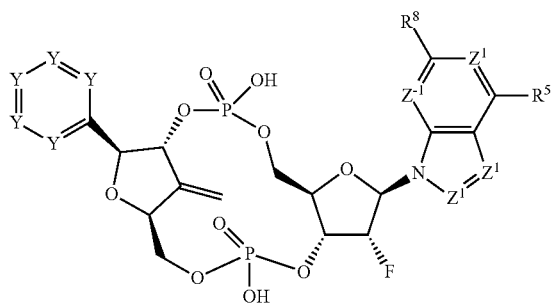

wherein each Z$^1$ is independently N or CR$^a$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{31}$, —S(O)R$^{a1}$, —S(O)NR$^{a1}$R$^{a1}$, —S(O)$_2$R$^{a1}$ or S(O)NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently CR$^a$ or N;

or a pharmaceutically acceptable salt, tautomer or stereoisomer thereof.

In a 29th aspect of the invention, there is provided a compound of the formula

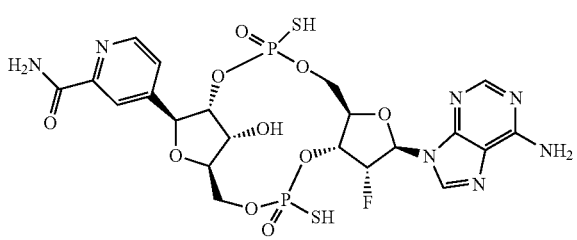 [SMILES: NC(=O)c1cc([C@@H]2O[C@@H]3COP(=O)(S)O[C@H]4[C@@H](F)[C@H](n5cnc6c(N)ncnc65)O[C@@H]4COP(=O)(S)O[C@@H]2[C@@H]3O)ccn1]

or a pharmaceutically acceptable salt, tautomer or stereoisomer thereof.

In a 30th aspect of the invention, there is provided a compound of the formula

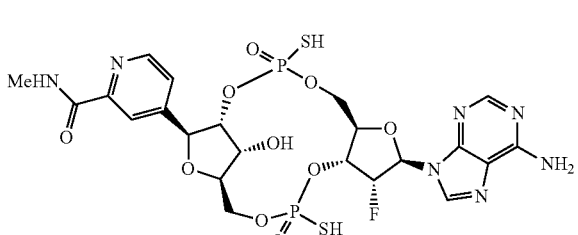

or a pharmaceutically acceptable salt, tautomer or stereoisomer thereof.

In another aspect of the invention, there is provided a compound of the formula

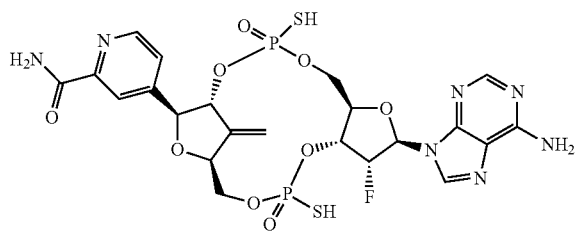 [SMILES: C=C1[C@H]2OP(=O)(S)OC[C@H]3O[C@@H](n4cnc5c(N)ncnc54)[C@H](F)[C@@H]3OP(=O)(S)OC[C@H]1O[C@H]2c1ccnc(C(N)=O)c1]

or a pharmaceutically acceptable salt, tautomer or stereoisomer thereof.

In another aspect of the invention, there is provided a compound of the formula

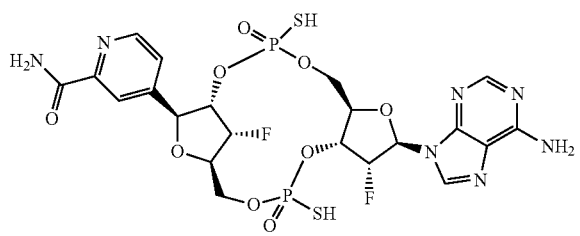 [SMILES: NC(=O)c1cc([C@@H]2O[C@@H]3COP(=O)(S)O[C@H]4[C@@H](F)[C@H](n5cnc6c(N)ncnc65)O[C@@H]4COP(=O)(S)O[C@@H]2[C@@H]3F)ccn1]

or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect of the invention, there is provided a compound which is
4-[(1R,6R,8R,9R,10R,15R,17S,18R)-8-(6-amino-9H-purin-9-yl)-9-fluoro-18-hydroxy-3,12-dioxo-3,12-disulfanyl-2,4,7,11,13,16-hexaoxa-3$\lambda^5$,12$\lambda^5$-diphosphatricyclo [13.2.1.0$^{6,10}$]octadecan-17-yl]pyridine-2-carboxamide,
4-[(1R,6R,8R,9R,10R,15R,17S,18R)-8-(6-amino-9H-purin-9-yl)-9-fluoro-18-hydroxy-3,12-dioxo-3,12-disulfanyl-2,4,7,11,13,16-hexaoxa-3$\lambda^5$,12$\lambda^5$-diphospha tricyclo [13.2.1.0$^{6,10}$]octadecan-17-yl]-N-methylpyridine-2-carboxamide, or
4-[(1R,6R,8R,9R,10R,15S,17S)-8-(6-amino-9H-purin-9-yl)-9-fluoro-18-methylidene-3,12-dioxo-3,12-disulfanyl-2,4,7,11,13,16-hexaoxa-3$\lambda^5$,12$\lambda^5$-diphosphatricyclo [13.2.1.0$^{6,10}$]octadecan-17-yl]pyridine-2-carboxamide,
4-[(1S,6R,8R,9R,10R,15R,17S,18R)-8-(6-amino-9H-purin-9-yl)-9,18-difluoro-3,12-dioxo-3,12-disulfanyl-2,4,7,11,13,16-hexaoxa-3$\lambda^5$,12$\lambda^5$-diphosphatricyclo [13.2.1.0$^{6,10}$] octadecan-17-yl]pyridine-2-carboxamide,
4-[(1R,6R,8R,9R,10R,15R,17S,18R)-9-fluoro-18-hydroxy-8-{3H-imidazo[2,1-f]purin-3-yl}-3,12-dioxo-3,12-disulfanyl-2,4,7,11,13,16-hexaoxa-3$\lambda^5$,12$\lambda^5$-diphosphatricyclo[13.2.1.0$^{6,10}$]octadecan-17-yl]pyridine-2-carboxamide or a pharmaceutically acceptable salt thereof.

OTHER EMBODIMENTS OF THE INVENTION

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including small cell lung cancer, non-small cell lung cancer, colorectal cancer, melanoma, renal cell carcinoma, head and neck cancer. Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers In another embodiment, the invention provides a method for the treatment and/or prophylaxis of various types of cancer, including without limitation, small cell lung cancer, non-small cell lung cancer, colorectal cancer, melanoma, renal cell carcinoma, head and neck cancer, Hodgkin's lymphoma or bladder cancer.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The cyclic dinucleotides of the invention induce Type I interferons and/or pro-inflammatory cytokines in vitro in human cells, animal cells and human blood. The cytokine-inducting activity of these CDNs requires the presence of STING, as confirmed by in vitro experiments in human or animal cells.

The CDNs of the invention are agonists of the receptor STING.

The term "agonist" refers to any substance that activates a biologic receptor in vitro or in vivo to provoke a physiological response.

"STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein that in humans is encoded by the gene TMEM173. Activation of STING by cyclic dinucleotides (CDN) leads to activation of the IRF3 and NF-κB pathways and consequently, to induction of Type I interferons and of pro-inflammatory cytokines, respectively.

Another object of the present invention is the cyclic dinucleotides of Formula (I), for use in a therapeutic treatment in humans or animals. In particular, the compounds of the present invention may be used for therapeutic or diagnostic applications in human or animal health.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "antagonist" refers to any substance that inhibits, counteracts, downregulates, and/or desensitizes a biologic receptor in vitro or in vivo to provoke a physiological response.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both.

"Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the cyclic dinucleotide of Formula (I) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of infection or disease in that human or animal, and/or to modulate the immune system of that human or animal to achieve some other therapeutic benefit.

In one particular embodiment, the cyclic dinucleotides of the present invention can be used for cytokine induction immunotherapy of immunosuppressed individuals.

In this example, a cyclic dinucleotide of Formula (I) would be administered to an immunosuppressed human or animal subject to induce in vivo production of one or more cytokines that directly or indirectly enhance the immune system of that human or animal.

Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof a cyclic dinucleotide of Formula (I) or a pharmaceutically acceptable salt or prodrug thereof.

In another embodiment, the cyclic dinucleotides of the present invention can be used for cytokine induction immunotherapy in combination with chemotherapy. In this example, a cyclic dinucleotide of Formula (I) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The present invention thus discloses a method for treating cancer, said method comprising administering to a patient in need thereof; a chemotherapeutic agent; and
a cyclic dinucleotide of Formula (I) or a pharmaceutically acceptable salt or prodrug thereof.

Another object of the present invention is the cyclic dinucleotides of Formula (I) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: small cell lung cancer, non-small cell lung cancer, colorectal cancer, melanoma, renal cell carcinoma, head and neck cancer, Hodgkin's lymphoma or bladder cancer.

The present invention thus discloses a method for treating a bacterial infection, a viral infection or a cancer, said method comprising administering to a patient in need thereof a cyclic dinucleotide of Formula (I) or a pharmaceutically acceptable salt or prodrug thereof.

Another object of the present invention is the cyclic dinucleotides of Formula (I) for use in the treatment of a pathology that may be alleviated by the induction of an immune response via the STING pathway.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colorectal cancers, blood cancers, lung cancers and bone cancers. Examples of such cancer types include neuroblastoma, intestinal carcinoma such as rectal carcinoma, colon carcinomas, familiar adenomatous polyposis carcinoma and hereditary non-polyposis colorectal cancer, esophageal carcinoma, labial carcinoma, larynx carcinoma, nasopharyngeal cancers, oral cavity cancers, salivary gland carcinoma, peritoneal cancers, soft tissue sarcoma, urothelial cancers, sweat gland carcinoma, gastric carcinoma, adenocarcinoma, medullary thyroid carcinoma, papillary thyroid carcinoma, renal carcinoma, kidney parenchymal carcinoma, ovarian carcinoma, cervical carcinoma, uterine corpus carcinoma, endometrial carcinoma, pancreatic carcinoma, prostate carcinoma, testis carcinoma, breast cancers including HER2 Negative, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, multiple myeloma, seminoma, osteosarcoma, chondrosarcoma, anal canal cancers, adrenal cortex carcinoma, chordoma, fallopian tube cancer, gastrointestinal stromal tumors, myeloproliferative diseases, mesothelioma, biliary tract cancers, Ewing sarcoma and other rare tumor types.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase I poisons, (viii) microtubule-directed agents. (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergistic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s)

of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα LTβR, Lymphotoxin α1β2, FAS, FASL, RELT, DR6, TROY, NGFR.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PDIH, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GTRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. The PD-1 antibody can be selected from Opdivo (nivolumab), Keytruda (pembrolizumab), PDR001 (Novartis: see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesar/AnaptysBio; see WO2014/179664), GLS-010 (Wuxi/Harbin Gloria Pharmaceuticals), AM-0001 (Armo/Ligand), or STI-1110 (Sorrento; see WO2014/194302). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224 In one aspect, In another aspect, the immuno-oncology agent is a PD-L1 antagonist, such as an antagonistic PD-L1 antibody. The PD-L1 antibody can be selected from Tecentriq (atezolizumab), durvalumab, avelumab, STI-1014 (Sorrento; see WO2013/181634), or CX-072 (CytomX; see WO2016/149201).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as anagonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intratumoral, intravenous or epidural injection as, for example, a sterile solution or suspension, or sustained release formulation; (3) topical application, for example, as a cream, ointment, or a controlled release patch or spray applied to the skin; or intratumorally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the present invention include those suitable for oral, intratumoral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers. e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous, intratumoral or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

Additionally, the phosphorothioate group can be drawn as either

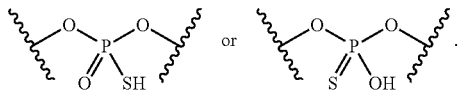 [SMILES: *OP(=O)(S)O* ; *OP(O)(=S)O*]

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, CF$_3$, CF$_2$CF$_3$, CN, halogen, haloalkyl, NO$_2$, sulfone, sulfoxide, ester, sulfonamide, carboxamide, alkoxy, alkoxyether, alkenyl, alkynyl, OH, C(O)alkyl, CO$_2$H, phenyl, heteroaryl, —O-phenyl, and —O— heteroaryl. Preferred examples of EWG include, but are not limited to, CF$_3$, CF$_2$CF$_3$—CN, halogen, SO$_2$(C$_{1-4}$ alkyl), CONH(C$_{1-4}$ alkyl), CON(C$_{1-4}$ alkyl)$_2$, and heteroaryl. More preferred examples of EWG include, but are not limited to, CF$_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application. CD3 denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington: The Science and Practice of Pharmacy, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., Design of Prodrugs, Elsevier (1985), and Widder, K. et al., eds., Methods in Enzymology, 112:309-396, Academic Press (1985);
b) Bundgaard, H., Chapter 5, "Design and Application of Prodrugs," A Textbook of Drug Design and Development, pp. 113-191, Krosgaard-Larsen, P. et al., eds., Harwood Academic Publishers (1991);
c) Bundgaard, H., Adv. Drug Deliv. Rev., 8:1-38 (1992);
d) Bundgaard, H. et al., J. Pharm. Sci., 77:285 (1988);
e) Kakeya, N. et al., Chem. Pharm. Bull., 32:692 (1984); and
f) Rautio, J (Editor). Prodrugs and Targeted Delivery (Methods and Principles in Medicinal Chemistry), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., Medicinal Chemistry: Principles and Practice, The Royal Society of Chemistry, Cambridge, UK (2$^{nd}$ edition, reproduced, 2006); Testa, B. et al., Hydrolysis in Drug and Prodrug Metabolism. Chemistry. Biochemistry and Enzymology, VCHA and Wiley-VCH, Zurich, Switzerland (2003); Wermuth, C. G., ed., The Practice of Medicinal Chemistry, 3$^{rd}$ edition, Academic Press, San Diego, CA (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 2007).

Compounds with general Formula (I) and Formula (II) may be prepared by reference to the methods illustrated in the following Schemes. As shown therein, the end product is a compound having the same structural formula as Formula (I) and Formula (I). It will be understood that any compound of Formula (I) and Formula (II) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

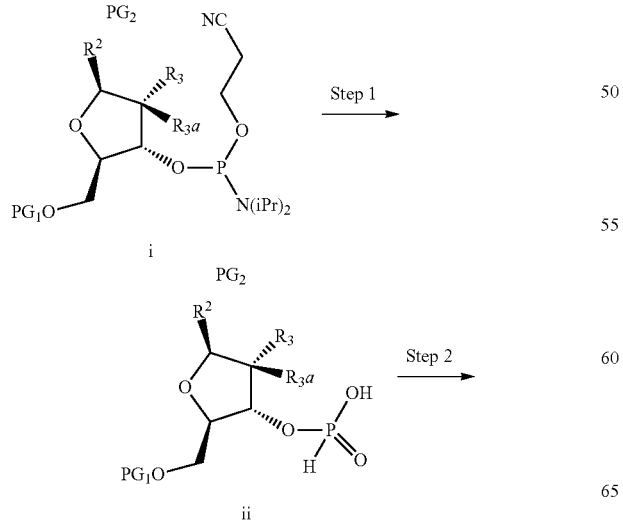

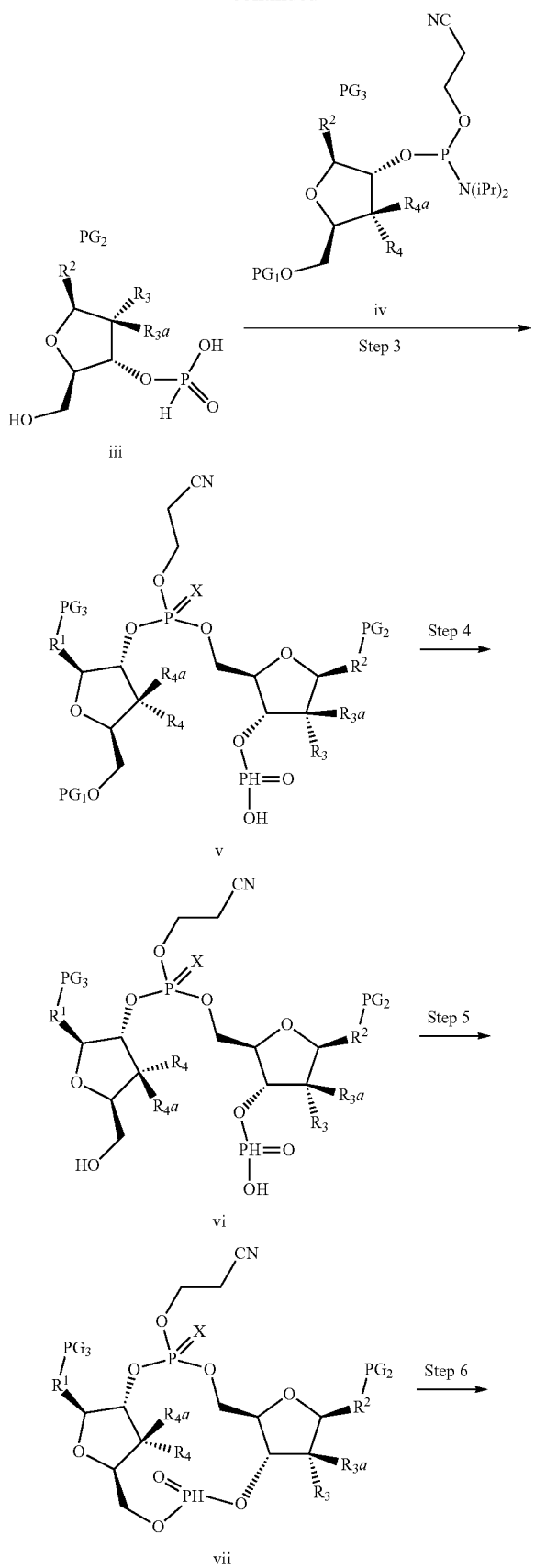

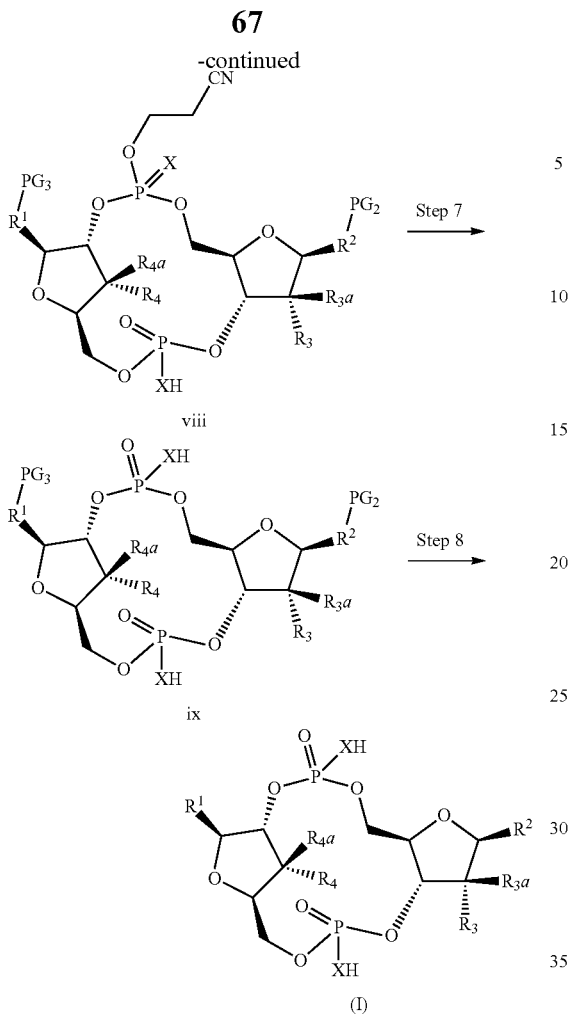

viii ix (I)

Method 1

One method for preparation of examples of the present disclosure is described in Scheme 1. The method starts from a ribo-nucleoside (i), wherein the nucleobase ($R^1$ or $R^2$) is appropriately protected ($PG_2$ or $PG_3$), such as with a benzoyl group, and the 5'-hydroxy group is appropriately protected ($PG_1$), such as with a DMTr or MMTr ether, and the 3'-position is a phosphoramidite functionality. In step 1, treatment with appropriate reagents, such as pyridine trifluoroacetate followed by butylamine, affords the H-phosphonate (ii). Subsequent removal of the 5'-OH protecting group in step 2, under acidic conditions ($PG_1$=DMTr or MMTr) affords compounds of formula iii. The resulting compound of formula iii may be reacted with a fully protected 2'-phosphoramidite (iv) in step 3 and then immediately thiolated, for example with DDTT (X=S), to provide compounds of formula v. Alternatively, treatment with an oxidant such as t-butyl hydroperoxide affords compounds of formula v where X=O. Removal of the 5'-protecting group from the second ribo-nucleoside in step 4, under acidic conditions ($PG_1$=DMTr or MMTr) provides compounds of formula vi. Treatment of compounds vi with an appropriate cyclization reagent in step 5, such as DMOCP provides compounds of formula vii. This material may then be immediately thiolated with an appropriate reagent, such as 3H-1,2-benzodithiol-3-one to afford compounds of formula viii in step 6. Compounds of formula viii may be treated with an appropriate reagent to remove the protecting groups of the nucleobase, for example $NH_4OH/MeOH$ ($PG_2$ and $PG_3$=benzoyl) to afford compounds of formula ix. Compounds of formula (I) may be prepared in step 8 by removal of the remaining protecting group from the 3'-OH of compounds ix with, for example fluoride anion, where $PG_4$=a silyl protecting group.

Scheme 2

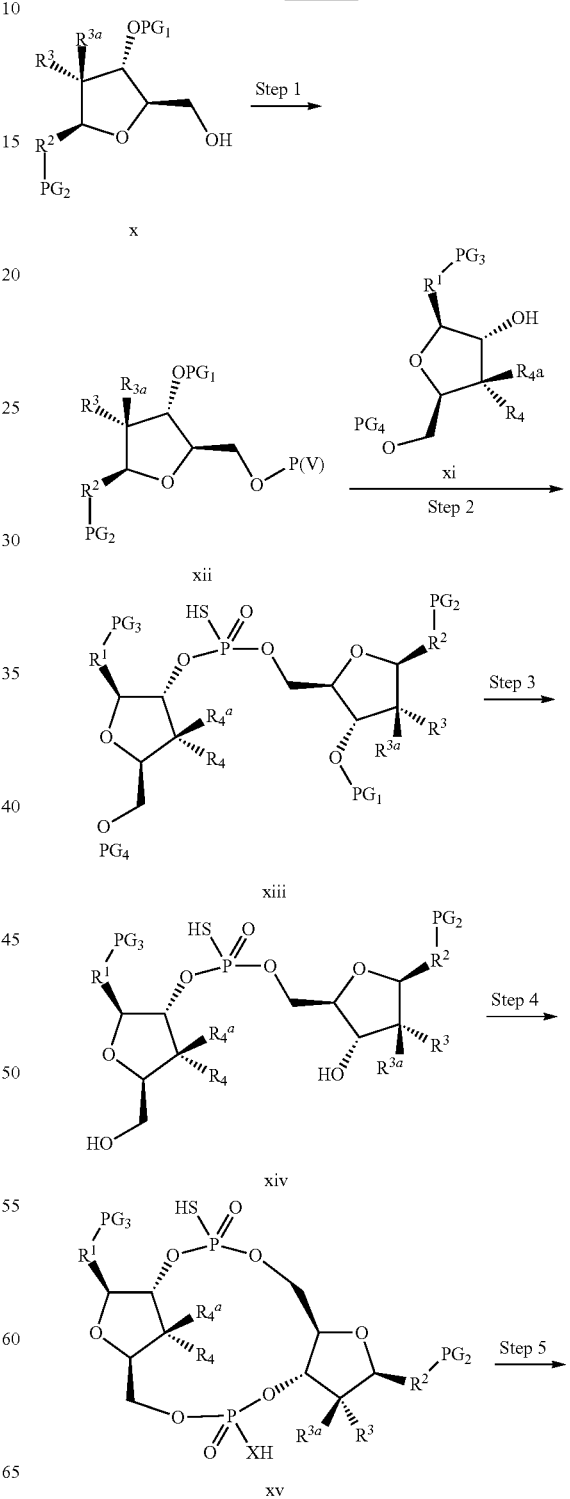

-continued

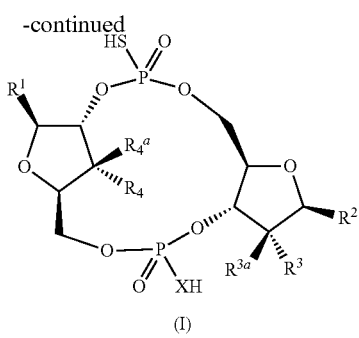

(I)

Method 2

Another method (Scheme 2) starts from an appropriately substituted natural or modified nucleoside (x), wherein the nucleobase ($R^2$) is appropriately protected (PG=protecting group) such as with a benzoyl group. In Step 1, treatment of x with an appropriate organophosphorus (V) reagent, for example one of those listed in Table 1, in an appropriate solvent (such as acetonitrile or dimethylformamide), with an appropriate base (for example DBU) affords compounds of formula xii. Treatment with an appropriately protected substituted natural or modified nucleoside (for example A) in Step 2, in an appropriate solvent (for example acetonitrile or dimethylformamide) in the presence of abase (for example DBU) affords compounds of formula xii. In Step 3, both protecting groups ($PG_1$ and $PG_2$) may be removed under conditions known to one skilled in the art to afford alcohol diol (xiv). Compounds of formula xiv may be treated in Step 4 with an appropriate cyclization reagent (for example diphenyl phosphite) followed by oxidation with, for example, t-butylhydroperoxide (X=O) or sulfurization with, for example DDTT (X=S) to provide compounds of formula xv. Removal of all remaining protecting group provides compounds of general formula (I).

TABLE 1

Organophosphorus Reagents and Corresponding -P(V) groups

| Organophosphorus (V) Reagent | -P(V) |
|---|---|
| Reagent-1 | |
| Reagent-2 | |
| Reagent-3 | |
| Reagent-4 | |

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

The following abbreviations may be used in the example section below and elsewhere herein:

| Abbreviation | Full Name |
|---|---|
| Ac | acetyl |
| ACN | acetonitrile |
| aq. | aqueous |
| DCM | dichloromethane |
| DDTT | ((dimethylamino-methylidene)amino)-3H-1,2,4-dithiazoline-3-thione |
| DMSO | dimethylsulfoxide |
| DMOCP | 2-chloro-5,5-dimethyl-1,3,2-dioxaphosphorinane 2-oxide |
| DMTr | 4,4'-dimethoxytrityl |
| MMTr | 4-methoxytrityl |
| EtOAc | ethyl acetate |
| Et$_3$N or TEA | triethylamine |
| EtOH | ethanol |
| HPLC | high-performance liquid chromatography |
| iPr | isopropyl |
| MeOH | methanol |
| RT | room temperature |
| satd. or sat'd | saturated |
| TBS | tButyldimethylsilyl |
| TFA | Trifluoroacetic acid |
| t$_R$ | retention time |

Preparation of Phosphorus (V) Reagents

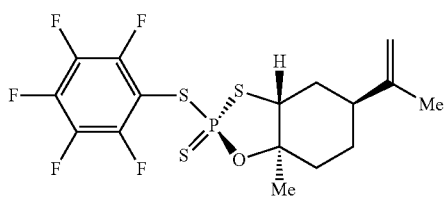

Reagent 1

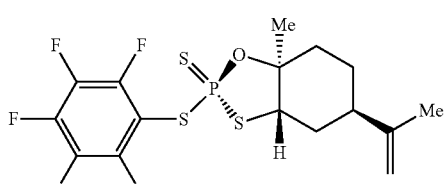

Reagent 2

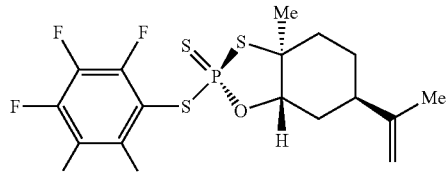

Reagent 3

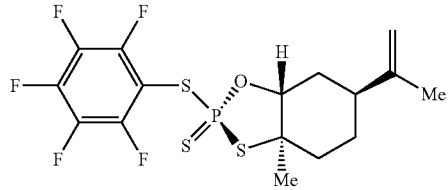

Reagent 4

The phosphorus (V) reagents (Reagents 1-4) used in the preparation of Examples of this invention were prepared according to the procedures provided in U.S. Ser. No. 62/657,551 filed Apr. 13, 2018, U.S. Ser. No. 62/656,8098 filed May 7, 2018, U.S. Ser. No. 62/697,896 filed Jul. 13, 2018 and U.S. Ser. No. 62/729,314 filed Sep. 10, 2018.

Examples 1-1, 1-2, 1-3, 1-4

4-[(1R,6R,8R,9R,10R,15R,17S,18R)-8-(6-amino-9H-purin-9-yl)-9-fluoro-18-hydroxy-3,12-dioxo-3,12-disulfanyl-2,4,7,11,13,16-hexaoxa-3λ$^5$,12λ$^5$-diphosphatricyclo[13.2.1.0$^{6,10}$]octadecan-17-yl]pyridine-2-carboxamide

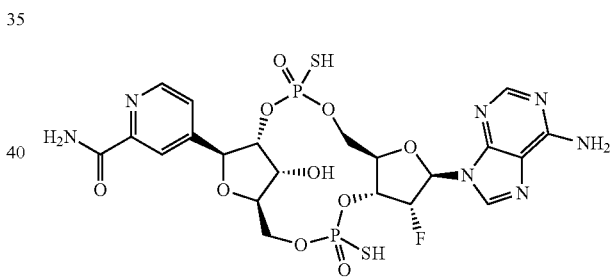

1-1 (Diastereomer 1)
1-2 (Diastereomer 2)
1-3 (Diastereomer 3)
1-4 (Diastereomer 4)

Preparation of 1A

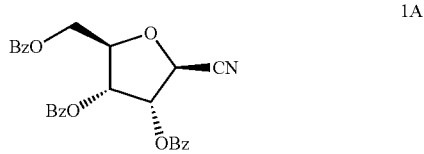

1A

To a solution of (2S,3R,4R,5R)-2-acetoxy-5-((benzoyloxy)methyl) tetrahydrofuran-3,4-diyl dibenzoate (10 g, 19.82 mmol) in 30 mL of DCM under a nitrogen atmosphere was added trimethylsilanecarbonitrile (3.47 mL, 27.8 mmol), followed by boron trifluoride diethyl etherate (2.45 mL, 19.8 mmol). The reaction mixture was stirred at room temperature for 14 hours. To this reaction mixture was added 100 mL of saturated NaHCO$_3$ and stirring was continued at room temperature for 30 min. The mixture was extracted with EtOAc (100 mL×3). The combined organic layers were washed with brine, then dried over Na$_2$SO$_4$. The mixture was then concentrated in vacuo and the residue was purified by silica gel chromatography (80 g column, 0-50% EtOAc/Hexane) to give 1A (7.56 g, 81% yield). $^1$H NMR (499 MHz, CHLOROFORM-d) 68.17-8.09 (m, 2H), 8.04-7.90 (m, 4H), 7.63-7.55 (m, 3H), 7.51-7.34 (m, 6H), 6.03 (dd, J=5.3, 4.5 Hz, 1H), 5.88 (t, J=5.5 Hz, 1H), 5.00 (d, J=4.4 Hz, 1H), 4.81-4.72 (m, 2H), 4.64 (d, J=8.4 Hz, 1H).

Preparation of 1B

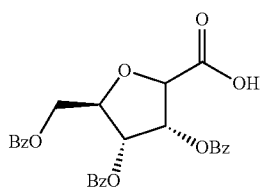

1B

To a solution of 1A (15 g, 31.8 mmol) in AcOH (40 mL) was added hydrogen chloride (5.30 mL, 63.6 mmol). The reaction mixture was heated to 120° C. for 40 min. The mixture was then concentrated to dryness and then purified by silica gel chromatography (120 g column, 0-60% EtOAc/hexane) to give 1B (12.6 g, 25.7 mmol, 81% yield). HPLC: retention time=0.73 min (H$_2$O/MeOH with 0.05% TFA, Shimadzu HPLC Xterra-S5-C18 4.6×50 mm, gradient=4 min, wavelength=220 nm); MS (ES): m/z=490 [M+H]$^+$.

Preparation of 1C

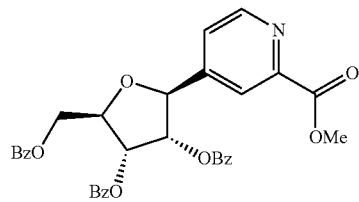

1C (4,4'-Di-t-butyl-2,2'-bipyridine)bis[3,5-difluoro-2-[5-trifluoromethyl-2-pyridinyl-kappan)phenyl-kappac]iridium (III) hexafluorophosphate (0.24 g, 0.24 mmol), nickel (II) chloride ethylene glycol dimethylether complex (0.26 g, 1.19 mmol), and 4,4'-di-tert-butyl-2,2'-bipyridine (0.32 g, 1.2 mmol) were added to a 50 mL vial equipped with a magnetic stir bar. Then, 1B (5.81 g, 11.85 mmol) was added, followed by methyl 4-bromopicolinate (3.07 g, 14.22 mmol), and Cs$_2$CO$_3$ (6.18 g, 18.95 mmol). The vial was then placed under nitrogen and dry DMA (120 mL) was added. The solution was then degassed for 15 minutes with nitrogen. The vial was then sealed and the cap was wrapped in parafilm. The vial was placed approximately 8 cm from a 34 W Blue LED, with the LED shining directly at the side of the vial. The reaction was then stirred for 72 hours. The crude reaction mixture was then poured into a mixture of water (100 mL) and ethyl acetate (100 mL). The water layer was extracted 3 times with ethyl acetate, and then the combined organic layers were washed with water, dried with Na$_2$SO$_4$, filtered and concentrated. The product was then purified by column chromatography (120 g column, 0-80% EtOAc/Hex, 40 min) to provide 1C (2.8 g, 4.81 mmol, 40.6% yield). $^1$H NMR (499 MHz, CHLOROFORM-d) δ 8.66 (dd, J=0.61, 5.02 Hz, 1H), 8.29 (s, 1H), 7.93-8.07 (m, 6H), 7.65 (d, J=5.13 Hz, 1H), 7.49-7.56 (m, 3H), 7.28-7.41 (m, 6H), 5.74 (t, J=5.33 Hz, 1H), 5.54 (t, J=5.71 Hz, 1H), 5.38 (d, J=5.94 Hz, 1H), 4.91 (dd, J=3.04, 12.17 Hz, 1H), 4.79 (td, J=3.39, 5.10 Hz, 1H), 4.70 (dd, J=3.65, 12.17 Hz, 1H), 1.21 (t, J=7.15 Hz, 1H).

Preparation of 1D

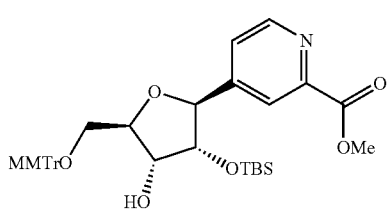

1D

To 1C (2.7 g, 4.59 mmol) was added 20 mL of dry MeOH and sodium methoxide (5.96 mL, 2.98 mmol, 0.5M). The mixture was stirred for 14 hours and then neutralized with Dowex 50W-X8H+ resin. The mixture was filtered and the filter cake was washed with MeOH and then the filtrate was concentrated to dryness. To a solution of the crude intermediate in pyridine (20 mL) was added (chloro(4-methoxyphenyl)methylene) dibenzene (1.67 g, 4.70 mmol) in DCM (5 mL) slowly at 0° C. The mixture was stirred at room temperature overnight. The solvent was then removed and the residue was poured into a mixture of water (100 mL) and ethyl acetate (100 mL). The aqueous layer was extracted 3 times with ethyl acetate, and then the combined organic layers were washed with brine, dried with Na$_2$SO$_4$, filtered and concentrated. The crude reaction was then purified by column chromatography (40 g column, 0-10% MeOH/DCM) to provide 1D (1.1 g, 45% yield). $^1$H NMR (499 MHz, CHLOROFORM-d) δ 8.69 (d, J=4.71 Hz, 1H), 8.32 (s, 1H), 7.67 (d, J=4.93 Hz, 1H), 7.41-7.51 (m, 3H), 7.22-7.38 (m, 9H), 6.87 (s, 1H), 6.85 (s, 1H), 4.87 (d, J=6.79 Hz, 1H), 4.07-4.27 (m, 3H), 4.02 (s, 1H), 3.93 (s, 2H), 3.80-3.84 (m, 3H), 3.55 (t, J=1.00 Hz, 1H), 3.52 (d, J=3.34 Hz, 1H), 3.38 (br d, J=3.55 Hz, 1H).

Preparation of 1E and 1F

1E

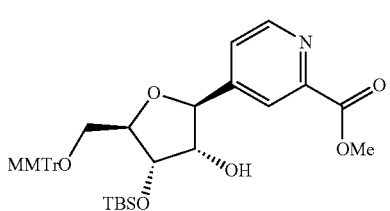

1F

To a solution of 1D (1.1 g, 2.0 mmol) and imidazole (0.42 g, 6.1 mmol) in pyridine (30 mL) was slowly added TBS-Cl (0.34 g, 2.2 mmol) in DCM (2 mL). The mixture was stirred for 5 hours and then 5 mL of MeOH was added. The mixture was then stirred for 1 hour and then concentrated to dryness. The crude material was purified by silica gel chromatography (40 g column, 0-100% EtOAc/Hexane, 35 min. gradient) to provide 1E (445 mg, 0.68 mmol, 33% yield) and 1F (418 mg, 0.64 mmol, 31% yield). 1E: $^1$H NMR (499 MHz, METHANOL-d$_4$) δ 8.67 (d, J=5.02 Hz, 1H), 8.49 (s, 1H), 7.75 (dd, J=1.05, 5.02 Hz, 1H), 7.42-7.55 (m, 4H), 7.22-7.40 (m, 8H), 6.86-6.93 (m, 2H), 4.90-4.92 (m, 1H), 4.25 (dd, J=5.02, 8.05 Hz, 1H), 4.19 (br d, J=2.19 Hz, 1H), 4.05-4.14 (m, 1H), 4.00 (s, 1H), 3.80-3.81 (m, 3H), 3.74-3.75 (m, 3H), 3.58 (dd, J=2.72, 10.56 Hz, 1H), 3.14-3.32 (m, 2H), 0.83-0.93 (m, 9H), −0.05--0.02 (M, 3H), −0.12--0.10 (m, 3H). 1F: $^1$H NMR (499 MHz, METHANOL-d$_4$) δ 8.66 (dd, J=0.63, 5.02 Hz, 1H), 8.49 (s, 1H), 7.78 (d, J=5.19 Hz, 1H), 7.43-7.54 (m, 4H), 7.22-7.39 (m, 8H), 6.89 (s, 1H), 6.88 (s, 1H), 4.89-4.92 (m, 1H), 4.07-4.21 (m, 3H), 3.90-4.05 (m, 1H), 3.79-3.81 (m, 3H), 3.75-3.78 (m, 2H), 3.58 (dd, J=2.87, 10.61 Hz, 1H), 3.13-3.32 (m, 1H), 0.88-0.88 (m, 1H), 0.86-0.88 (m, 8H), 0.17 (br d, J=11.50 Hz, 1H), 0.06-0.08 (m, 3H), −0.02-0.00 (m, 3H).

Preparation of 1G

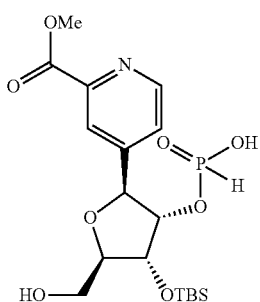

1G

To a solution of 1F (418 mg, 0.637 mmol) in pyridine (6 mL, 74 mmol) under a nitrogen atmosphere was added diphenyl phosphonate (0.37 mL, 1.9 mmol), and the mixture was stirred at room temperature for 20 min. To the mixture was added water (0.80 mL, 45 mmol) and then triethylamine (0.89 mL, 6.4 mmol). The mixture was stirred for an additional 20 min. The mixture was then evaporated and azeotroped with MeOH and then purified by column chromatography (12 g, 0-15% MeOH/DCM) to provide a crude intermediate. To this crude material was added 5 mL of DCM and then 2,2-dichloroacetic acid (0.26 mL, 3.2 mmol). The mixture was stirred at room temperature for 2 hours, and then pyridine (0.5 mL, 6.2 mmol) was added, and the reaction mixture was concentrated to dryness. The residue was purified by reverse phase (C18) chromatography (150 g column, 0% to 30% ACN in aqueous NH$_4$Ac (0.04%)) to give methyl 1G (130 mg, 0.29 mmol, 46% yield). $^1$H NMR (499 MHz. METHANOL-d$_4$) δ 8.64 (d, J=4.89 Hz, 1H), 8.35 (s, 1H), 7.86 (d, J=5.13 Hz, 1H), 7.39 (s, 1H), 5.12 (d, J=5.96 Hz, 1H), 4.36-4.46 (m, 1H), 4.31 (t, J=4.41 Hz, 1H), 4.10 (q, J=4.17 Hz, 1H), 3.99 (s, 3H), 3.83 (dd, J=3.81, 12.04 Hz, 1H), 3.74 (dd, J=4.29, 12.04 Hz, 1H), 0.96 (s, 9H), 0.17 (d, J=7.03 Hz, 6H).

Preparation of 1H

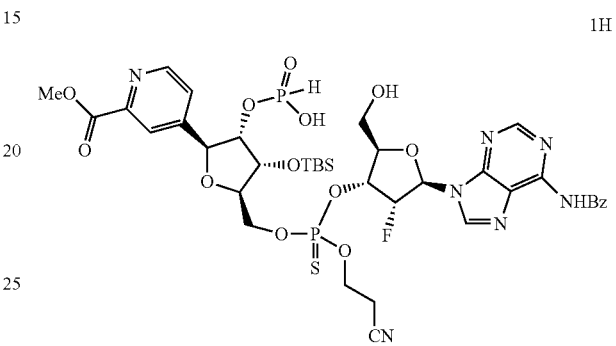

1H (2R,3R,4R,5R)-5-(6-benzamido-9H-purin-9-yl)-2-((bis (4-methoxyphenyl) (phenyl)methoxy)methyl)-4-fluorotetrahydrofuran-3-yl (2-cyanoethyl) diisopropylphosphoramidite (Sigma-Aldrich, 510 mg, 0.58 mmol) was dissolved in 4 mL of anhydrous acetonitrile and then concentrated to a think oil (repeated two times). To this oil, was added a third portion of anhydrous acetonitrile (4 mL), and then 4 Å molecular sieves (150 mg) were added. To a mixture of 1G (130 mg, 0.29 mmol) and 1H-tetrazole (81 mg. 1.16 mmol) was added anhydrous acetonitrile (4 mL). This mixture was concentrated to dryness. The mixture was then azetroped two additional times with anhydrous CH$_3$CN (4 mL). During the final azetrope, the solution was concentrated to a volume of ~2 mL, and 4 Å molecular sieves (150 mg) were added under nitrogen. To this mixture, with a positive pressure nitrogen line, was added the previously prepared solution via cannulae. The reaction mixture was then stirred for 3 hours. The reaction was then treated with (E)-N,N-dimethyl-N'-(3-thioxo-3H-1,2,4-dithiazol-5-yl) formimidamide (130 mg. 0.64 mmol) and the solution was stirred for 20 minutes. The resulting yellow solution was filtered and carefully concentrated in vacuo (120 mbar, 36° C. water bath). The thick oil was transferred to a separatory funnel containing 6% (m/v) aqueous sodium bicarbonate. The product was extracted with two portions of ethyl acetate and the combined organics were dried over magnesium sulfate, filtered, and concentrated. The crude material was azeotroped with anhydrous acetonitrile and then dissolved in dichloromethane (3 mL). Triethylsilane (0.28 mL, 1.74 mmol) was added, followed by the dropwise addition of 2,2-dichloroacetic acid (112 mg, 0.87 mmol). After 2 hours, the reaction mixture was treated with pyridine (0.5 mL), and stirring was continued for 10 minutes. The mixture was then concentrated in vacuo (300 mbar, then 50 mbar, 35° C. water bath) to a viscous oil. The oil was dissolved in methanol (5 mL) and concentrated to dryness (repeated two times). The residue was then purified by reverse phase (C18) chromatography (50 g column, 0% to 60% AcCN in aqueous NH$_4$Ac (0.04%0)) to provide 1H, as a mixture of two diastereomers (193 mg, 69%) m/z: 952.1 (M+H).

Preparation of 1I

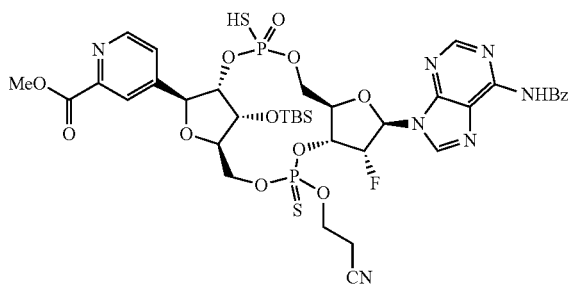

1I

Intermediate 1H (100 mg, 0.11 mmol) was dissolved in anhydrous pyridine (1 mL) and concentrated to dryness in vacuo (repeated two times). The resulting material was dissolved in anhydrous pyridine (5 mL) and was added to a solution of 2-chloro-5,5-dimethyl-1,3,2-dioxaphosphinane 2-oxide (78 mg, 0.42 mmol) in pyridine (5 mL) dropwise at −10° C. The reaction was warmed to room temperature and stirred for 20 minutes. (E)-N,N-dimethyl-N'-(3-thioxo-3H-1,2,4-dithiazol-5-yl)formimidamide (43 mg, 0.21 mmol) was then added and the mixture was stirred at room temperature for 20 minutes. Water (0.50 mL) was added and stirring continued for an additional 30 minutes. The mixture was then concentrated to dryness. The residue was partitioned between sat. aq. NaHCO₃ (10 mL) and EtOAc (15 mL). The organic layer was collected and the aqueous layer was extracted with EtOAc (15 mL×2). The combined organic layers were dried over Na₂SO₄, concentrated and purified by silica gel column chromatography (12 g column, 0-20% MeOH/DCM) to give 1I (74 mg, 0.08 mmol, 73% yield), as a mixture of four diastereomers. m/z: 966.3 (M+H).

Preparation of Examples 1-1, 1-2, 1-3 and 1-4

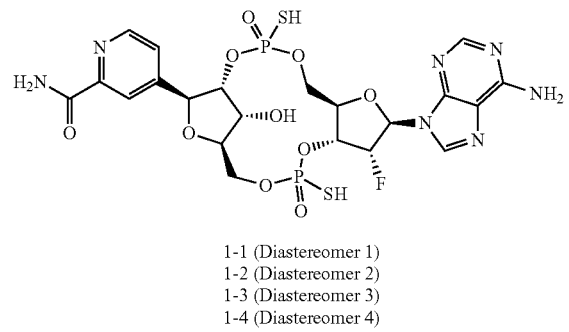 [SMILES: NC(=O)c1cc([C@@H]2O[C@@H]3COP(=O)(S)O[C@H]4[C@@H](F)[C@H](n5cnc6c(N)ncnc65)O[C@@H]4COP(=O)(S)O[C@@H]2[C@@H]3O)ccn1]

1-1 (Diastereomer 1)
1-2 (Diastereomer 2)
1-3 (Diastereomer 3)
1-4 (Diastereomer 4)

To 1I (74 mg, 0.077 mmol) was added ammonia in MeOH (2 mL, 7N). The reaction mixture was stirred at 50° C. for 3 hours. The reaction mixture was then evaporated to dryness. To the crude mixture was added triethylamine trihydrofluoride (1 mL, 6.1 mmol). The mixture was heated to 37° C. for 2 hours. The reaction was then treated with 1M NH₄OAc and then stirred at room temperature for 10 minutes. The solution was then filtered and the filtrate was purified by preparative HPLC (Conditions: Column: Agilent Bonus RP 21.2×100 mm, 5-μm particles; Mobile Phase A: water with 20-mM ammonium acetate; Mobile Phase B: acetonitrile; Gradient: 00% B hold 0-6 minute. 0%-25% B over 16 minutes, then a 4-minute hold at 100% B; Flow: 20 mL/min) to provide 1-1 as a single diastereomer (13 mg, 24% yield). Three additional diastereomers were isolated as mixtures: Diastereomers 1-2 and 1-3 (4 mg, 7% yield) and 1-3 and 1-4 (32 mg, 56% yield).

Example 1-1 ¹H NMR (500 MHz. DMSO-d₆) δ 8.51 (d, J=4.88 Hz, 1H), 8.11 (s, 1H), 8.01 (s, 1H), 7.77 (br d, J=4.58 Hz. 1H), 7.56 (br s, H), 6.19 (dd, J=2.59, 15.11 Hz, 1H), 5.66 (m 1H), 4.87-5.04 (m, 1H), 4.75 (br d, J=9.16 Hz, 1H), 4.55 (br s, 1H), 4.41-4.51 (m, 1H), 4.30 (br s, 1H), 4.05-4.19 (m, 2H), 4.01 (br dd, J=6.26, 11.44 Hz, 1H), 3.55 (br s. 1H). 3.17 (s. 1H). Retention time: 2.21 min. (Agilent Bonus RP, 2.1 mm×50 mm, 1.8 μm particles; Mobile Phase A: water with 20 mM ammonium acetate: Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm). m/z: 680.12.

Examples 2-1, 2-2, 2-3 and 2-4

4-[(1R,6R,8R,9R,10R,15R,17S,18R)-8-(6-amino-9H-purin-9-yl)-9-fluoro-18-hydroxy-3,12-dioxo-3,12-disulfanyl-2,4,7,11,13,16-hexaoxa-3λ⁵,12λ⁵-diphosphatricyclo[13.2.1.0⁶,¹⁰]octadecan-17-yl]-N-methylpyridine-2-carboxamide

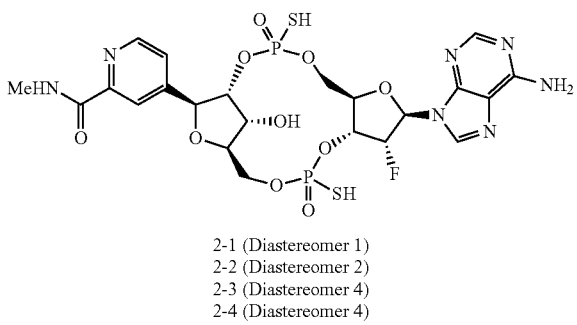 [SMILES: CNC(=O)c1cc([C@@H]2O[C@@H]3COP(=O)(S)O[C@H]4[C@@H](F)[C@H](n5cnc6c(N)ncnc65)O[C@@H]4COP(=O)(S)O[C@@H]2[C@@H]3O)ccn1]

2-1 (Diastereomer 1)
2-2 (Diastereomer 2)
2-3 (Diastereomer 4)
2-4 (Diastereomer 4)

Intermediate 1I (30 mg. 0.031 mmol) was dissolved in MeOH (0.5 mL) and then a 30% solution of methylamine in EtOH (2 mL) was added. The mixture was heated at 50° C. for 10 hrs. The mixture was then concentrated to dryness under a stream of nitrogen. The resulting residue was suspended in triethylamine trihydrofluoride (1 mL) and heated at 37° C. for 3 hrs. To the reaction was then added a 2M ammonia acetate solution (2 mL) and stirring was continued for 20 min. The mixture was then filtered and purified by Preparative HPLC (Conditions: Column: Luna Phenyl-Hex, Column, 5 μm, 4.6×250 mm, Flow rate: 1 mL/min, Mobile Phase: A: 100 mM NH₄OAc (pH 6.5); Mobile Phase B: MeOH, with the following gradient: 20% B, 10 min, 20-95% B, 1 min and 95%-20%, B 2 min) to provide 2-1 (2.3 mg, 10% yield) as a single diastereomer, 2-2 and 2-3 as a 2:1 mixture of diastereomers (2.6 mg, 12% yield) and 2-4 as a single diastereomer (1.8 mg, 8% yield).

Example 2-1: HPLC retention time: 10.87 min. (Luna Phenyl-Hex 3 um 3×150; Mobile Phase A: water with 20 mM NH$_4$Ac; Mobile Phase B: MeOH with 20 mM NH$_4$Ac; Gradient: 0%-15% B over 20 minute. 15%-95% B over 1 minute, Flow: 0.5 mL/min); $^1$H NMR (500 MHz, METHANOL-d$_4$) δ 8.49 (d, J=4.92 Hz, 1H), 8.36 (s, 1H), 8.18 (s, 2H), 7.81 (d, J=4.49 Hz, 1H), 6.31 (dd, J=2.24, 14.64 Hz, 1H), 5.66-5.84 (m, 1H), 5.17 (ddd, J=3.47, 6.63, 9.88 Hz, 1H). 4.92-4.99 (m, 1H), 4.67-4.83 (m, 1H), 4.55 (d, J=3.95 Hz, 1H), 4.41-4.52 (m, 2H), 4.24-4.31 (m, 1H), 4.04-4.16 (m, 2H), 3.17-3.78 (m, 1H), 2.92 (s, 3H). m/z: 694.1 (M+H).

Examples 2-2 and 2-3: HPLC retention time: 12.07 min and 12.45 min. (Luna Phenyl-Hex 3 um 3×150; Mobile Phase A: water with 20 mM NH$_4$Ac; Mobile Phase B: MeOH with 20 mM NH$_4$Ac; Gradient: 0%-15% B over 20 minute. 15%-95% B over 1 minute, Flow: 0.5 mL/min). m/z: 694.1 (M+H).

Example 2-4: HPLC retention time: 13.62 min. (Luna Phenyl-Hex 3 um 3×150; Mobile Phase A: water with 20 mM NH$_4$Ac: Mobile Phase B: MeOH with 20 mM NH$_4$Ac; Gradient: 0%-15% B over 20 minute. 15%-95% B over 1 minute, Flow: 0.5 mL/min); $^1$H NMR (500 MHz, METHANOL-d$_4$) δ 8.21-8.24 (m, 1H), 8.17-8.20 (m 1H), 8.07-8.11 (m, 1H), 7.96-8.02 (m, 2H), 6.22-6.29 (m, 1H), 5.84-6.02 (m, 1H), 4.98-5.02 (m, 1H), 4.65-4.71 (m, 1H), 4.43-4.48 (m, 1H), 4.33-4.43 (m, 2H), 4.29-4.33 (m, 1H), 4.26 (s, 2H), 3.44-3.49 (m, 1H), 3.17-3.26 (m, 1H), 2.91-2.93 (m, 3H). m/z: 694.1 (M+H).

Examples 3-1, 3-2, 3-3 and 3-4

4-[(1R,6R,8R,9R,10R,15S,17S)-8-(6-amino-9H-purin-9-yl)-9-fluoro-18-methylidene-3,12-dioxo-3,12-disulfanyl-2,4,7,11,13,16-hexaoxa-3λ$^5$,12λ$^5$-diphosphatricyclo[13.2.1.0$^{6,10}$]octadecan-17-yl] pyridine-2-carboxamide

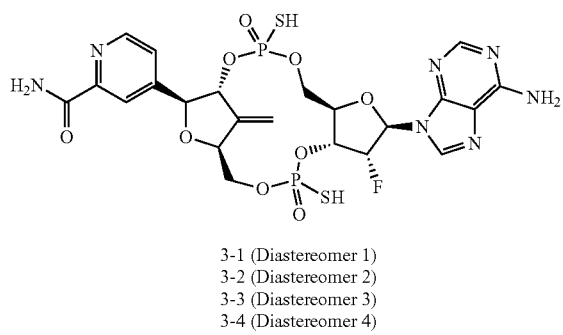 [SMILES: C=C1[C@H]2OP(=O)(S)OC[C@H]3O[C@@H](n4cnc5c(N)ncnc54)[C@H](F)[C@@H]3OP(=O)(S)OC[C@H]1O[C@H]2c1ccnc(C(N)=O)c1]

3-1 (Diastereomer 1)
3-2 (Diastereomer 2)
3-3 (Diastereomer 3)
3-4 (Diastereomer 4)

Preparation of 3A

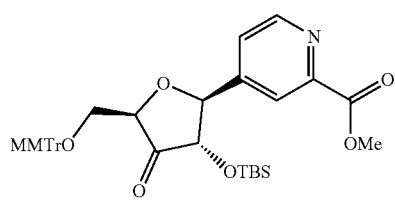

To a suspension of Dess-Martin periodinane (323 mg, 0.76 mmol) in dry DCM (5 mL) was added t-BuOH (0.08 mL, 0.80 mmol) and the resultant mixture was stirred at room temperature for 10 min before a solution of 1E (250 mg, 0.381 mmol) in dry DCM (5 mL) was added slowly. The mixture was stirred for 10 hours at room temperature. The reaction mixture was then diluted with EtOAc (30 mL) and treated with a Na$_2$S$_2$O$_3$ solution (10 mL, 1M), then saturated NaCl solution (10 mL) and then saturated NaHCO$_3$ solution (10 mL). The layers were separated and the aqueous layer was extracted with EtOAc. The combined organic layers were washed with brine, then dried over Na$_2$SO$_4$, filtered and concentrated in vacuo to provide the crude product (235 mg), which was used directly in the next step.

Preparation of 3B

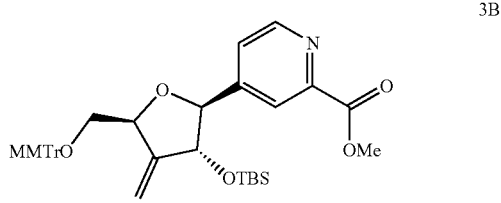

A suspension of methyltriphenylphosphonium bromide (2140 mg, 6 mmol), and sodium amide (350 mg, 9.0 mmol) in toluene (30 mL) was heated to reflux for 2.5 hours. The reaction was then cooled to room temperature and allowed to settle for 2 hours. To a solution of crude 3A (240 mg, 0.36 mmol) in anhydrous THF (8 mL) was added the above solution (5 mL, 1.4 mmol). The reaction was stirred at room temperature for 1 hour and then concentrated to dryness. The crude product was dissolved in a small amount of DCM and charged onto a 24 g ISCO silica gel cartridge and eluted using a 25 min. gradient of EtOAc/Hexane (0-100%) to provide 3B (85 mg, 0.13 mmol, 36% yield over two steps). m/z: 652.08 (M+H).

Preparation of 3C

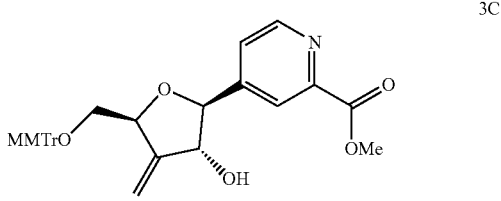

To a solution of 3B (85 mg, 0.13 mmol) in THF (5 mL) was added TBAF (0.08 mL, 0.08 mmol). The mixture was then stirred for 3 hrs at room temperature. The reaction mixture was then evaporated to dryness and the crude product was dissolved in a small amount of DCM and charged onto a 12 g ISCO silica gel cartridge and eluted with a 20 min gradient of EtOAc/Hexane (0-100%) to provide 3C. (61 mg, 87% yield). $^1$H NMR (499 MHz, CHLOROFORM-d) δ 8.64 (d, J=4.89 Hz, 1H), 8.30 (s, 1H), 7.65 (dd, J=1.13, 4.95 Hz, 1H), 7.46-7.53 (m, 4H), 7.35-7.41 (m, 2H), 7.21-7.32 (m, 6H), 6.83-6.88 (m, 2H), 5.33 (t, J=2.32 Hz, 1H), 5.11 (t, J=2.27 Hz, 1H), 4.83 (td, J=1.98, 3.78 Hz, 1H), 4.62 (d, J=8.34 Hz, 1H), 4.48 (br d, J=7.03 Hz, 1H), 3.93 (s, 3H), 3.80 (s, 3H), 3.35-3.43 (m, 2H), 0.02 (s, 1H).

Preparation of 3D

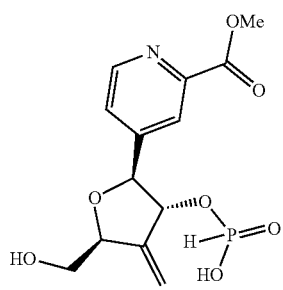

3D

To a stirred solution of 3C (61 mg, 0.11 mmol) in pyridine (1.5 mL, 18.6 mmol) under a nitrogen atmosphere was added diphenyl phosphonate (0.07 mL, 0.34 mmol), and the reaction was stirred at room temperature for 20 min. To the reaction mixture was added water (0.14 mL, 7.9 mmol) and then triethylamine (0.16 mL, 1.14 mmol). The mixture was stirred for 20 min. The mixture was then evaporated and azeotroped a few of time with MeCN. To a stirred solution of the crude intermediate and triethylsilane (0.18 mL, 1.14 mmol) in DCM (3 mL) was added 2,2-dichloroacetic acid (0.05 mL, 0.57 mmol). The mixture was stirred at room temperature for 2 hours and then pyridine (0.5 mL, 6.2 mmol) was added, and then the solution was concentrated. The residue was purified by reverse phase (C18) chromatography eluting with 0% to 30% AcCN in aq $NH_4HCO_3$ (0.04%) to provide 3D (27 mg, 0.08\ mmol, 72% yield) as a white solid.

Preparation of 3E

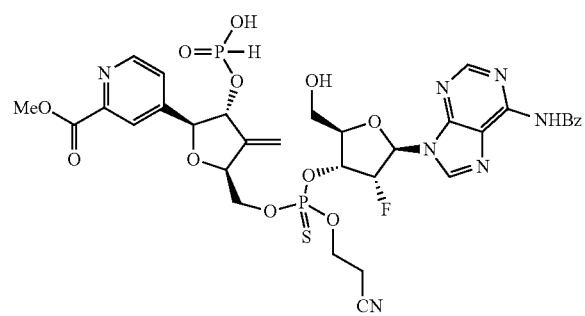

3E (2R,3R,4R,5R)-5-(6-benzamido-9H-purin-9-yl)-2-((bis (4-methoxyphenyl)(phenyl)methoxy)methyl)-4-fluorotetrahydrofuran-3-yl (2-cyanoethyl) diisopropylphosphoramidite (Sigma-Aldrich, 220 mg, 0.25 mmol) was dissolved in 4 mL of anhydrous acetonitrile and then concentrated to a thick oil (repeated two times). To this oil was added a third portion of anhydrous acetonitrile (4 mL), and then 4 Å molecular sieves (100 mg) were added under nitrogen. This solution was allowed to sit, capped, while the next solution was prepared. To a mixture of 3D (27 mg, 0.082 mmol) and 1H-tetrazole (23 mg, 0.33 mmol) was added anhydrous acetonitrile (2 mL). This mixture was also concentrated to dryness. The mixture was azeotroped two additional times with anhydrous $CH_3CN$ (2 mL). After the final azeotrope, 2 mL of anhydrous $CH_3CN$ and 4 Å molecular sieves (100 mg) were added under nitrogen. With a positive pressure nitrogen line, the previously prepared solution was added to the solution of 3D. The reaction mixture was stirred for 3 hours and then (E)-N,N-dimethyl-N'-(3-thioxo-3H-1,2,4-dithiazol-5-yl)formimidamide (67 mg, 0.33 mmol) was added. The solution was stirred for 20 minutes and then filtered and carefully concentrated in vacuo (120 mbar, 36° C. water bath) to remove MeCN. The resulting thick oil was transferred to a separatory funnel containing 6% (m/v) aqueous sodium bicarbonate. The resulting mixture was extracted with EtOAc (2×). The combined organic layers were dried over magnesium sulfate, filtered, and concentrated to a yellow foam. The crude material was then azeotroped with anhydrous acetonitrile and then dichloromethane (3.0 mL) was added to form a homogenous solution. Triethylsilane (0.08 mL, 0.50 mmol) was added, followed by the dropwise addition of 2,2-dichloroacetic acid (32 mg, 0.25 mmol). After 1 hour, pyridine (0.5 mL) was added, and the mixture was stirred for 10 minutes, then concentrated in vacuo (300 mbar, then 50 mbar, 35° C. water bath). The resulting residue was purified by reverse phase (C18) chromatography (50 g column, 0% to 60% AcCN in aqueous $NH_4Ac$ (0.04%)) to provide 3E, as a mixture of two diastereomers (35 mg, 51%). m/z 834.08 (M+H).

Preparation of 3F

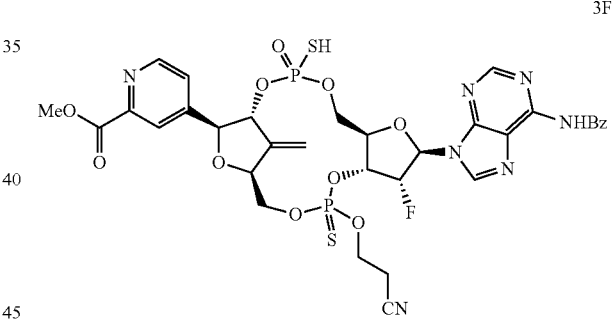

3F

Intermediate 3E was converted to Intermediate 3F, using a procedure analogous to Example 1I. The crude product was purified by silica gel column chromatography (12 g column, 0-20% MeOH/DCM, 25 min) to give 3F (30 mg, 0.04 mmol, 84% yield), as a mixture of four diastereomers. m/z: 848.2 (M+H).

Preparation of Examples 3-1, 3-2, 3-3 and 3-4

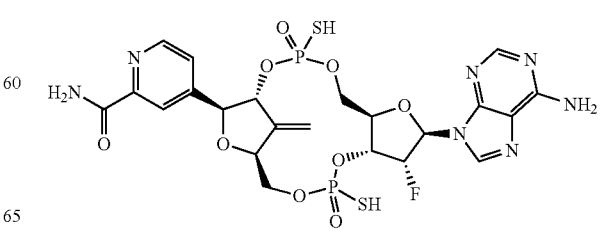

To 3F (30 mg, 0.035 mmol) was added ammonia in MeOH (2 mL, 7N). The reaction mixture was stirred at room temperature for 30 min and then at 50° C. for 5 hours. The reaction mixture was then evaporated to dryness. The crude product was purified by Preparative HPLC (Conditions: Column: Xselect RP Prep C18 19×150 mm: Mobile Phase A: water with 20-mM TEAA; Mobile Phase B: acetonitrile/water (8:2) with 20-mM TEAA; Gradient: 8%-17% B over 20 minute. 17%-95% B over 2 minutes, then 95%-8% over 3-minute, Flow: 20 mL/min) to provide 3-1 (0.9 mg, 4% yield), 3-2 as (1.2 mg, 4% yield), 3-3 (1.4 mg, 4% yield) and 3-4 (1.4 mg, 4% yield).

Example 3-1: HPLC retention time: 7.56 min. (Xselect CSH C18 Column, 3.5 um, 3×150 mm; Mobile Phase A: water with 20-mM TEAA; Mobile Phase B: acetonitrile/water (8:2) with 20-mM TEAA; Gradient: 5%-21% B over 14 minute. 21%-95% B over 2 minutes, then 95%-05% over 1-minute, Flow: 0.5 mL/min); $^1$H NMR (500 MHz, METHANOL-$d_4$) δ 8.53-8.59 (m, 1H), 8.41-8.48 (m, 2H). 8.20-8.24 (m, 2H), 6.27-6.40 (m, 1H), 5.66-5.72 (m, 2H), 5.54-5.62 (m, 1H), 5.24-5.30 (m, 1H), 4.77-4.79 (m, 1H), 4.5-64.63 (m, 2H), 4.31-4.46 (m, 3H), 4.08-4.19 (m, 2H), m/z: 675.9 (M+H).

Example 3-2: HPLC retention time: 9.20 min. (Xselect CSH C18 Column, 3.5 um, 3×150 mm: Mobile Phase A: water with 20-mM TEAA; Mobile Phase B: acetonitrile/water (8:2) with 20-mM TEAA: Gradient: 5%-21% B over 14 minute. 21%-95% B over 2 minutes, then 95%-5% over 1-minute. Flow: 0.5 mL/min $^1$H NMR (500 MHz, METHANOL-$d_4$) δ 8.49-8.63 (m, 1H). 8.38-8.46 (m, 1H), 8.13-8.27 (m, 1H), 7.80-8.02 (m, 1H), 7.30-7.61 (m, 1H), 6.23-6.43 (m, 1H), 5.76-5.88 (m, 1H), 5.52-5.74 (m, 2H), 5.19-5.45 (m, 1H), 4.72-4.83 (m, 1H), 4.49-4.64 (m, 1H), 4.22-4.47 (m, 1H), 4.06-4.20 (m, 3H), 3.84-4.02 (m, 2H). m/z: 675.9 (M+H).

Example 3-3: HPLC retention time: 9.65 min. (Xselect CSH C18 Column, 3.5 um, 3×150 mm; Mobile Phase A: water with 20-mM TEAA; Mobile Phase B: acetonitrile/water (8:2) with 20-mM TEAA; Gradient: 5%-21% B over 14 minute. 21%-95% B over 2 minutes, then 95%-5% over 1-minute, Flow: 0.5 mL/min); 1H NMR (500 MHz, METHANOL-$d_4$) δ 8.52-8.61 (m, 1H), 8.41-8.47 (m, 1H), 8.16-8.31 (m, 2H), 7.90-8.00 (m, 1H), 6.27-6.40 (m, 1H), 5.52-5.82 (m, 2H), 5.17-5.39 (m, 2H), 4.71-4.81 (m, 1H), 4.52-4.63 (m, 2H), 4.27-4.45 (m, 2H), 4.09-4.24 (m, 2H), 3.86-4.05 (m, 1H). m/z: 675.9 (M+H).

Example 3-4: HPLC retention Time: 12.06 min. (Xselect CSH C18 Column. 3.5 um, 3×150 mm; Mobile Phase A: water with 20-mM TEAA; Mobile Phase B: acetonitrile/water (8:2) with 20-mM TEAA; Gradient: 5%-21% B over 14 minute. 21%-95% B over 2 minutes, then 95%-5% over 1-minute, Flow: 0.5 mL/min); $^1$H NMR (400 MHz, METHANOL-$d_4$) δ 8.52-8.58 (m, 1H), 8.32 (br s, 1H), 8.24 (s, 1H), 8.18 (s, 1H), 7.87-7.93 (m, 1H), 6.33 (d, J=15.90 Hz, 1H), 5.65-5.69 (m, 1H), 5.49-5.65 (m, 1H), 5.32-5.43 (m 1H), 5.25-5.32 (m, 1H), 4.95-5.07 (m 1H), 4.73-4.80 (m, 1H), 4.61 (d, J=8.98 Hz, 1H), 4.26-4.49 (m, 3H), 4.04-4.21 (m, 2H), m/z: 675.9 (M+H).

Examples 4-1 and 4-2

4-[(1S,6R,8R,9R,10R,15R,17S,18R)-8-(6-amino-9H-purin-9-yl)-9,18-difluoro-3,12-dioxo-3,12-disulfanyl-2,4,7,11,13,16-hexaoxa-3$\lambda^5$,12$\lambda^5$-diphosphatricyclo[13.2.1.0$^{6,10}$]octadecan-17-yl]pyridine-2-carboxamide

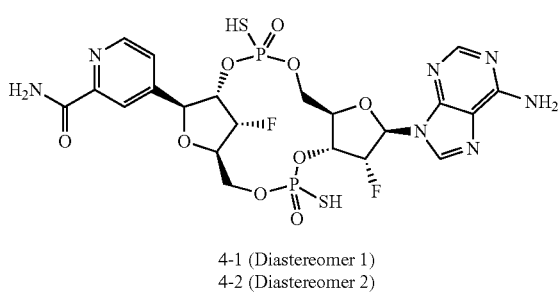 [SMILES: NC(=O)c1cc([C@@H]2O[C@@H]3COP(=O)(S)O[C@H]4[C@@H](F)[C@H](n5cnc6c(N)ncnc65)O[C@@H]4COP(=O)(S)O[C@@H]2[C@@H]3F)ccn1]

4-1 (Diastereomer 1)
4-2 (Diastereomer 2)

Preparation of 4A

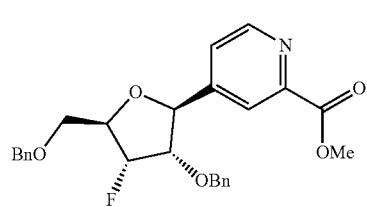

4A (4,4'-Di-t-butyl-2,2'-bipyridine)bis[3,5-difluoro-2-[5-trifluoromethyl-2-pyridinyl-kappan)phenyl-kappac]iridium (III) hexafluorophosphate (0.17 g, 0.16 mmol), nickel (II) chloride ethylene glycol dimethylether complex (0.18 g, 0.81 mmol), and 4,4'-di-tert-butyl-2,2'-bipyridine (0.22 g, 0.81 mmol) were added to a 150 mL vial equipped with a magnetic stir bar. Then (2R,3S,4R,5R)-3-(benzyloxy)-5-((benzyloxy)methyl)-4-fluorotetrahydrofuran-2-carboxylic acid (2.9 g, 8.05 mmol) was added, followed by methyl 4-bromopicolinate (2.09 g, 9.7 mmol), and Cs$_2$CO$_3$ (4.2 g, 12.9 mmol). The vial was then placed under nitrogen and dry DMA (80 mL) was added. The solution was then degassed for 15 minutes with nitrogen. The vial was then sealed and the cap was wrapped in parafilm. The vial was placed approximately 8 cm from a 34 W Blue LED, with the LED shining directly at the side of the vial. The reaction was then stirred for 22 hours. The crude reaction mixture was then poured into a mixture of water (100 mL) and ethyl acetate (100 mL). The aqueous layer was extracted 3 times with ethyl acetate, and then the combined organic layers were washed with water, dried with Na$_2$SO$_4$, filtered and concentrated. The product was then purified by silica gel column chromatography (80 g column, 0-80% EtOAc/Hex, 40 min) to provide 4A (1.09 g, 2.41 mmol, 30% yield). m/z: 452.4 (M+H).

Preparation of 4B

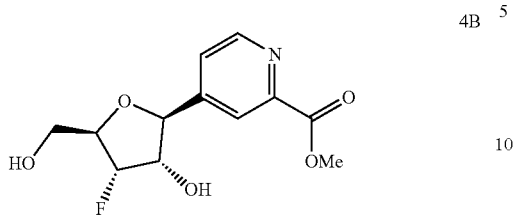

Intermediate 4A (1.0 g, 2.2 mmol) was dissolved in ethanol (40 mL) and cyclohexene (20 mL) under nitrogen. The reaction mixture was purged with nitrogen several times. Pd(OH)$_2$ (0.23 g, 0.33 mmol) was added and the reaction mixture was heated to reflux for 4 hours. To the reaction mixture was added celite and it was then filtered and washed with EtOH. The crude product was concentrated and then purified by column chromatography (40 g column, 0-25% MeOH/DCM, 35 min) to provide 4B (160 mg, 0.59 mmol, 27% yield). $^1$H NMR (499 MHz, CHLOROFORM-d) δ 8.75 (d, J=5.01 Hz, 1H), 8.27 (s, 1H), 7.65 (dd, J=1.07, 5.01 Hz, 1H), 5.04-5.17 (m, 1H), 4.79-4.84 (m, 1H), 4.40-4.49 (m, 1H), 4.14-4.24 (m, 1H), 4.01-4.08 (m, 5H), 3.96-4.01 (m, 2H), 3.83-3.91 (m, 2H), 3.70-3.76 (m, 1H), 3.51 (s, 1H). m/z 272.3 (M+H).

Preparation of 4C

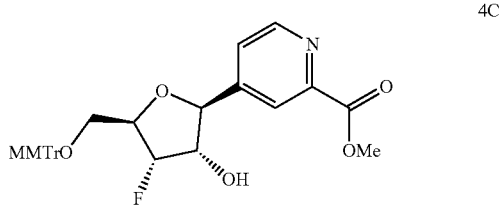

To a solution of 4B (160 mg, 0.59 mmol) in pyridine (6 mL) was slowly added a solution of (chloro(4-methoxyphenyl)methylene)dibenzene (210 mg, 0.68 mmol) in DCM (1 mL). The mixture was stirred at room temperature overnight. An additional 0.5 equivalents of (chloro(4-methoxyphenyl)methylene)dibenzene was added and the reaction was stirred for an additional 3 hours. The reaction was then treated with 2 mL of MeOH. The solvent was then removed and the residue was purified by silica gel column chromatography (24 g column, 0-100% EtOAc/Hex) to provide 4C. (214 mg, 67% yield). $^1$H NMR (499 MHz, CHLOROFORM-d) δ 8.73 (d, J=4.89 Hz, 1H), 8.39 (s, 1H), 7.69 (dd, J=1.01, 4.95 Hz, 1H), 7.39-7.45 (m, 4H), 7.21-7.34 (m, 9H), 6.81-6.90 (m, 2H), 4.91-5.07 (m, 1H), 4.84 (d, J=8.82 Hz, 1H), 4.47 (br s, 1H), 4.41 (br s, 1H), 3.92 (s, 3H), 3.79-3.83 (m, 3H), 3.57 (dd, J=3.46, 10.61 Hz, 1H), 3.30 (dd, J=3.16, 10.55 Hz, 1H), 2.89-3.05 (m, 1H).

Preparation of Intermediate 4D

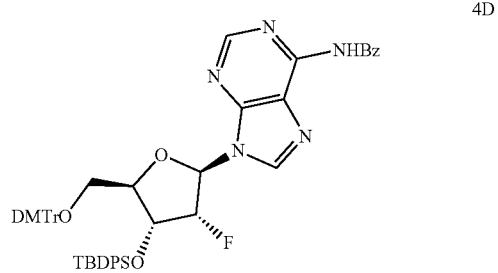

To a cooled (0° C.) solution of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (Astatech, 500 mg, 0.74 mmol) and imidazole (150 mg, 2.22 mmol) in DMF (3.7 mL) was added tert-butyldiphenylchlorosilane (290 μl, 1.11 mmol) dropwise via syringe. The ice-water bath was then removed and the reaction was stirred at room temperature under a nitrogen atmosphere. After 22 hours, a second portion of imidazole (50 mg, 0.74 mmol) and tert-butyldiphenylchlorosilane (95 μl, 0.37 mmol) was added to the reaction. After 3 additional hours, a third portion of imidazole (50 mg, 0.74 mmol) and tert-butyldiphenylchlorosilane (95 μl, 0.37 mmol) was added to the reaction and the mixture was stirred for 24 hours. The reaction was then treated with methanol (750 μL, 18.5 mmol), stirred at room temperature for 30 min, and then concentrated in vacuo. The remaining volatiles were removed under a stream of nitrogen. The residue was partitioned between EtOAc (20 mL) and water (20 mL), and the layers were separated. The aqueous phase was extracted with EtOAc (1×20 mL), and the combined organic layers were washed with water (4×10 mL), brine (10 mL) dried (Na$_2$SO$_4$), filtered, and concentrated. The crude 4D was carried into the next step without further purification. LCMS, [M+H]$^+$=914.

Preparation of 4E

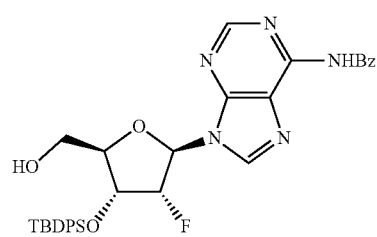

To a solution of 4D (680 mg, 0.74 mmol) and triethylsilane (300 μL, 1.9 mmol) in CH$_2$Cl$_2$ (4 mL) was added trifluoroacetic acid (110 μL, 1.48 mmol) dropwise via syringe. The reaction was stirred at room temperature under a nitrogen atmosphere. After 1.5 hours, the reaction was treated with MeOH (4 mL) and stirred for 10 min. The mixture was then concentrated in vacuo and azeotroped twice with MeOH (2×4 mL). The crude product was dissolved in a small amount of CH$_2$Cl$_2$, adsorbed onto a plug of SiO$_2$, and purified by flash chromatography (SiO$_2$, 40 g column, 0-50% acetone/hexanes, 14.4 min gradient then a 14.4 min hold, 40 mL/min) to afford 4E (384 mg, 85% yield) as a white solid. LCMS, [M+H]+=612. ¹H NMR (500 MHz, CHLOROFORM-d) δ 8.71 (s, 1H), 8.15 (s, 1H), 8.05-7.99 (m, 2H), 7.74-7.66 (m, 4H), 7.65-7.59 (m, 1H), 7.56-7.51 (m, 2H), 7.50-7.37 (m, 6H), 6.27 (dd, J=11.3, 6.8 Hz, 1H), 5.62 (ddd, J=51.8, 6.7, 4.8 Hz 1H), 4.70-4.62 (m, 1H), 4.13 (br s, 1H), 3.68 (d, J=13.1 Hz, 1H), 3.10 (dd J=13.1, 1.6 Hz, 1H), 1.17 (s, 9H).

Preparation of 4F

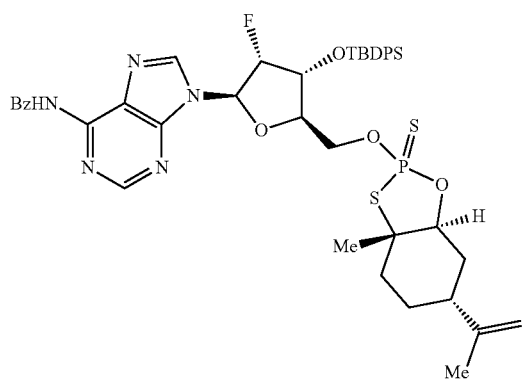

4F

Intermediate 4E (1.0 g, 1.64 mmol) and Reagent 3 in MeCN (15 mL) was cooled to an internal temperature of 0° C. DBU (0.4 mL, 2.5 mmol) was added in one portion, and the mixture was stirred at 0° C. for 30 min. To the reaction mixture was added acetic acid (280 μL, 4.9 mmol) at 0° C., and then silica gel was added and the mixture was concentrated. The crude product was purified by ISCO silica gel chromatography (80 g. 0-10% gradient MeOH/DCM). Fractions containing the desired product were concentrated to a white foam which was co-evaporated with heptane (3×50 mL) to afford 4F (1.2 g, 87% yield) as a white solid. LCMS, [M+H]⁺=858.8: ¹H NMR (499 MHz, CHLOROFORM-d) δ 8.95 (s, 1H), 8.69 (s, 1H), 8.07 (s, 1H), 7.99-8.04 (m, 2H), 7.69-7.74 (m, 4H), 7.61-7.66 (m, 1H), 7.38-7.57 (m, 9H), 7.28 (s, 2H), 6.32 (d, J=2.03 Hz, 1H), 6.28-6.38 (m, 1H), 4.95 (dd, J=2.09, 4.23 Hz, 1H), 4.85 (dd, J=2.15, 4.29 Hz, 1H), 4.81-4.98 (m, 1H), 4.62-4.71 (m, 2H), 4.58-4.61 (m, 1H), 4.43 (br s, 1H), 4.25-4.37 (m, 2H), 4.15 (ddd, J=4.23, 9.33, 11.59 Hz, 1H), 2.51 (br s, 1H), 2.20-2.26 (m, 1H), 1.99-2.06 (m, 5H), 1.81-1.91 (m, 3H), 1.65-1.75 (m, 5H), 1.23-1.32 (m, 1H), 1.16 (s, 9H).

Preparation of 4G

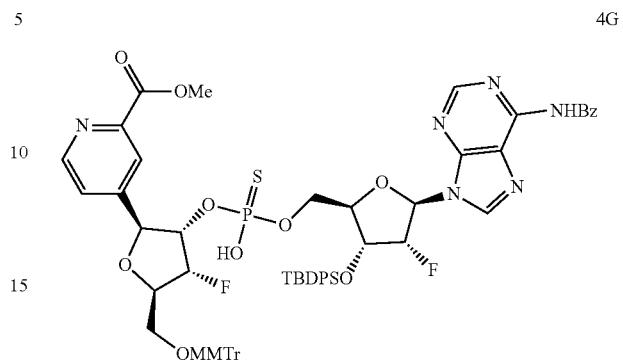

4G

To a solution of 4C (210 mg, 0.39 mmol) and 4F (570 mg, 0.67 mmol) in acetonitrile (8 mL) was added DBU (180 μl, 1.20 mmol) dropwise to give a pale yellow solution. After 10 min, the reaction mixture was diluted with DCM (4 mL) and treated with acetic acid (110 μL, 2.0 mmol). The resulting mixture was co-evaporated with silica gel, and then purified by flash chromatography over 40 g of silica gel, eluting with 0-15% MeOH/DCM to afford 4G (320 mg, 66% yield) as white solid. LCMS, [M+H]+=1233.0.

Preparation of 4H

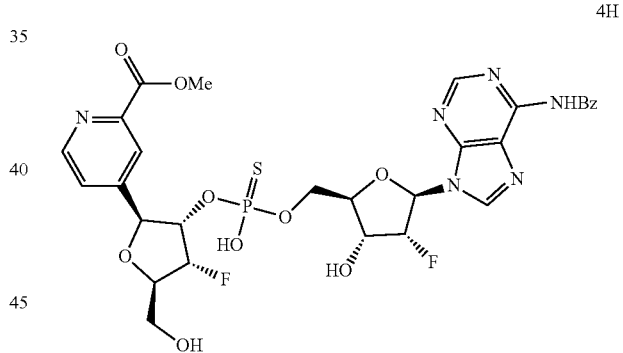

4H

To 4G (230 mg, 0.19 mmol) was added triethylamine trihydrofluoride (2 mL, 12.3 mmol). The reaction mixture was stirred at 37° C. for 2 h, diluted with acetonitrile (3.4 mL) and then treated with Et₃N (2.56 mL, 18.4 mmol) and isopropoxytrimethylsilane (4880 mg, 36.9 mmol). The mixture was stirred at room temperature for 10 min, and then concentrated in vacuo. The crude intermediate was dissolved in DCM (6 mL). Triethylsilane (0.24 mL, 1.49 mmol) and then 2,2-dichloroacetic acid (96 mg, 0.75 mmol) were added. The mixture was stirred for 2 hours and then concentrated to dryness. The crude product was dissolved in a small amount of MeOH, adsorbed onto a plug of Celite and purified on a reverse phase ISCO Gold 50 g C18 column (Mobile Phase A: 5:95 acetonitrile:water with 0.01M ammonium acetate; Mobile Phase B: 95:5 acetonitrile:water with 0.01M ammonium acetate; Gradient: 0% B hold for 5 min, 0-35% B gradient for 20 min and 100% hold for 5 min, run at 30 mL/min) to afford 4H (168 mg, 91% yield) as a white solid after lyophilization. LCMS, [M+H]⁺=723.08.

Preparation of 4I

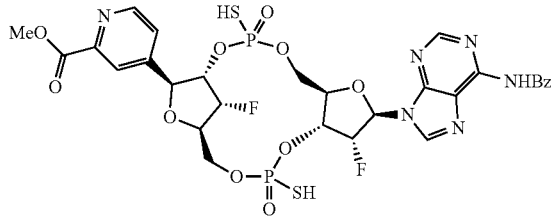

To a room temperature solution of 4H (138 mg, 0.191 mmol) in pyridine (19 mL) was added a solution of diphenyl phosphonate (74 µL, 0.38 mmol) in DCM (1 mL) dropwise over 20 minutes. To this reaction mixture was added (E)-N,N-dimethyl-N'-(3-thioxo-3H-1,2,4-dithiazol-5-yl)formimidamide (120 mg, 0.57 mmol) and the mixture was stirred at room temperature for 20 hours. The reaction mixture was then concentrated to dryness. The residue was then dissolved in methanol and filtered. The filtrate was concentrated and the resulting residue was purified on a reverse phase ISCO Gold 50 g C18 column (Mobile Phase A: 5:95 acetonitrile:water with 0.01M ammonium acetate; Mobile Phase B: 95:5 acetonitrile:water with 0.01M ammonium acetate: Gradient: 0-30% B gradient over 15 min) to afford 4I (93 mg, 61% yield) as a mixture of two diastereomers. LCMS, [M+H]$^+$=801.6.

Preparation of Examples 4-1 and 4-2

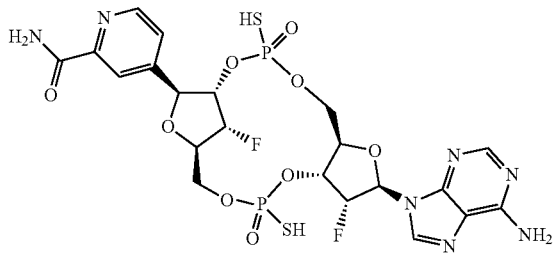 [SMILES: NC(=O)c1cc([C@@H]2O[C@@H]3COP(=O)(S)O[C@H]4[C@@H](F)[C@H](n5cnc6c(N)ncnc65)O[C@@H]4COP(=O)(S)O[C@@H]2[C@@H]3F)ccn1]

Intermediate 4I (93 mg, 0.116 mmol) was treated with 7N ammonia in MeOH (5 mL, 35.0 mmol) and the reaction mixture was stirred for 5 h at 5° C. The reaction mixture was then concentrated and the crude product was purified by Preparative HPLC (Chromatographic Conditions: Instrument: Waters Autopure; Column: Xselect RP Prep C18 OBD Column, 5 µm, 19×150 mm; Flow rate: 20.0 mL/min; Mobile Phase: A: 100 mM NH$_4$OAc (pH:6.5); B: ACN (% A=100-% B)) gradient 0-20% B over 12 min, 20-95% B over 0.5 min, 95% B hold for 0.5 min and 95-0% B for 0.5 min) to afford Examples 4-1 and 4-2, respectively.

Examples 4-1 (10.8 mg, 12% yield); Retention time: 6.53 min, Analytical HPLC Chromatographic Conditions 1: Observed Mass: m/z 682.5. $^1$H NMR (499 MHz, METHANOL-d$_4$) δ 8.24 (s, 1H), 8.08-8.18 (m, 3H), 7.91 (s, 1H), 6.24 (d, J=15.62 Hz, 1H), 5.90-5.98 (m, 1H), 5.80-5.88 (m, 1H), 4.89-4.94 (m 1H), 4.77-4.84 (m, 1H), 4.37-4.56 (m 2H), 4.27-4.36 (m, 2H), 4.15 (m 1H), 3.34-3.38 (m, 1H), 3.24-3.32 (m 1H). $^{31}$P NMR (202 MHz, METHANOL-d$_4$) δ 57.15 (s, 1P), 54.05 (s, 1P).

Examples 4-2 (28.7 mg, 32% yield)); Retention time: 7.50 min, Analytical HPLC Chromatographic Conditions 1; Observed Mass: m/z 682.5; $^1$H NMR (499 MHz, METHANOL-d$_4$) 8.42 (d, J=5.0 Hz, 1H), 8.21 (s, 2H), 8.05 (s, 1H), 7.83 (d, J=4.2 Hz, 1H), 6.32-6.24 (m, 1H), 5.78-5.59 (m, 2H), 5.03-4.92 (m, 1H), 4.91-4.89 (m, 1H), 4.84-4.76 (m, 1H), 4.57-4.47 (m, 2H), 4.47-4.40 (m, 1H), 4.38-4.25 (m, 2H), 4.17-4.07 (m, 1H). $^{31}$P NMR (202 MHz, METHANOL-d$_4$) δ 56.1 (s, 1P), 54.4 (s, 1P), 54.3 (s, 1P).

Analytical HPLC Chromatographic Conditions 1:
Instrument: Agilent 1290; Column: Xselect CSH C18 Column, 3.5 µm, 2.1×150 mm; Flow rate: 0.35 mL/min; Mobile Phase: A: 20 mM NH$_4$OAc (pH 6.5): B: 20 mM NH$_4$OAc in ACN; gradient 0-35% B over 15 min, 35-100% B over 1 min.

Examples 5-1 and 5-2

4-[(1R,6R,8R,9R,10R,15R,17S,18R)-9-fluoro-18-hydroxy-8-{3H-imidazo[2,1-f]purin-3-yl}-3,12-dioxo-3,12-disulfanyl-2,4,7,11,13,16-hexaoxa-3λ$^5$,12λ$^5$-diphosphatricyclo[13.2.1.0$^{6,10}$]octadecan-17-yl]pyridine-2-carboxamide

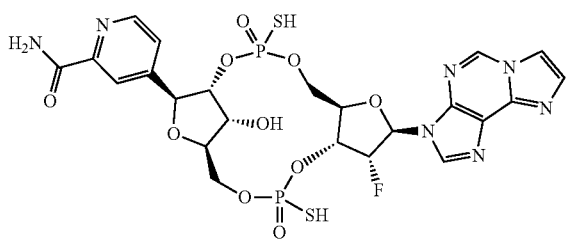

5-1 (Diastereomer 1)
5-2 (Diastereomer 2)

The diastereomeric mixture of Examples 1-3 and 1-4 (5.6 mg, 0.66 mmol) and 2-chloroacetaldehyde (20 mg, 0.13 mmol) in a pH 4.5 AcOH/NaOAc buffer (0.5 mL) was stirred at room temperature for 10 hours. The crude material was purified via preparative HPLC with the following conditions: Column: Agilent Bonus RP 21.2×100 mm, 5-µm particles; Mobile Phase A: water with 20-mM ammonium acetate: Mobile Phase B: acetonitrile; Gradient: 0% B hold 0-6 minute. 0%-25% B over 16 minutes, then a 4-minute hold at 100% B; Flow: 20 mL/min. Fractions containing the desired products were combined and dried via centrifugal evaporation to provide Example 5-1 (0.8 mg) and Example 5-2 (0.5 mg).

Example 5-1: HPLC retention time: 2.26 min. (Column: Agilent Bonus RP. 2.1 mm×50 mm, 1.8 um; Mobile Phase A: water with 20 mM ammonium acetate; Mobile Phase B: acetonitrile. Temperature: 50° C.: Gradient: 0% B hold 1 min, then 0% B to 100% B over 4 min, then a 0.75 min hold at 100% B; Flow: 1 mL/min; Detection: MS and UV (220 nm)); Observed Mass: m/z 704.1; $^1$H NMR (500 MHz, DMSO-d$_6$) δ 9.13 (s, 1H), 8.51 (br d, J=4.63 Hz, 1H), 8.40 (s, 1H), 8.09 (m, 2H), 7.71 (br d, J=3.62 Hz. 1H), 7.43 (br s, 1H), 6.35 (br d, J=14.39 Hz, 1H), 4.91-5.04 (m, 1H), 4.78 (br d, J=8.41 Hz, 1H), 4.36-4.58 (m, 2H), 4.19-4.36 (m, 2H), 4.13 (br s, 1H), 3.87-4.08 (m, 2H), 3.74 (br d, J=9.68 Hz, 1H), 3.45 (m, 1H).

Example 5-2: HPLC retention time: 2.09 min. (Column: Agilent Bonus RP. 2.1 mm×50 mm, 1.8 um; Mobile Phase A: water with 20 mM ammonium acetate; Mobile Phase B: acetonitrile. Temperature: 50° C.: Gradient: 0% B hold 1 min, then 0% B to 100% B over 4 min, then a 0.75 min hold at 100% B; Flow: 1 mL/min; Detection: MS and UV (220 nm)); Observed Mass: m/z 703.85: $^1$H NMR (500 MHz, DMSO-$d_6$) δ 9.24 (s, 1H), 8.35 (s, 1H), 8.25 (d, J=4.88 Hz, 1H), 8.21 (br s, 1H), 8.10 s, 1H), 7.88-7.92 (m, 2H), 6.36 (br d, J=14.65 Hz, 1H), 4.86-5.06 (m, 1H), 4.73 (br d, J=9.16 Hz, 1H), 4.42-4.58 (m, 2H), 4.21-4.37 (m, 2H), 4.11 (br s, 1H), 3.98 (br d, J=6.10 Hz, 2H), 3.69-3.90 (m, 1H), 3.38 (m, 1H).

Evaluation of Biological Activity

STING THP1 Reporter Assay Protocol

THP1-Dual™ cells were derived from the human THP-1 monocyte cell line by stable integration of two inducible reporter constructs. To this end, THP1-Dual™ cells allow the simultaneous study of the NF-κB pathway, by monitoring the activity of SEAP, and the IRF pathway by assessing the activity of a secreted luciferase (Lucia). Both reporter proteins are readily measurable in the cell culture supernatant when using QUANTI-Blue™, a SEAP detection reagent, and QUANTI-Luc™, a luciferase detection reagent.

THP1-Dual™ cells induce the activation of NF-κB in response to STING agonists. They also trigger the IRF pathway upon stimulation with STING agonists, such as cGAMP. Here, the THP-1-Dual cells were used to assess STING binders for function on the cellular level.

Serial dilutions of compounds in DMSO were added to low volume 384 well plates at 100 nl/well using an ECHO acoustic dispenser (Labcyte, model 550) to achieve final starting concentration of 100 μM in cell suspension. THP-1 Dual™ STING reporter cells (Invivogen, Dual cells cat #THPD-nfis) were added to the plates with compounds at 15,000 cells in 10 μL per well in RPMI media (Gibco, cat #11875) containing 10% human plasma in a low volume 384-well black wall clear bottom tissue culture plate (Corning, cat #3542) for SEAP assay and low volume solid white plate (Corning, cat #3826) for luciferase assay. One column of the plate was reserved for treatment with cGAMP at 100 μM for 100% activation calculation and one column for no treatment (DMSO only) for baseline activation. Plates were then incubated in 37° C. incubator at 5% $CO_2$ for 20 hours.

In the SEAP assay, 5 μl of 2× QuantiBlue (Invivogen, cat #Rep-qb2) is added to 384 well black plates seeded with THP1 cells and incubated at 37° C. for 2 hours. Plates were read on the Envision (Perkin Elmer) at 620 nm wavelength (OD620). In the luciferase assay, 5 μl of Quantiluc (Invivogen, Rep-qlc2) is added to white 384 well plates seeded with THP1 cells and read at 5 minutes on the Envision (Perkin Elmer) using a luminescence protocol (RLU). For both cell lines, 100% activation was determined by value (RLU) of THP-1 Dual STING cells stimulated with 100 μM cGAMP (Invivogen, cat #TLRL-NACGA23-5).

Sting HTRF Binding Assays

A time resolved FRET-based competition binding assay was used to assess test article binding to STING WT and STING AQ. His-tagged STING cytoplasmic domain (WT or AQ) at a concentration of 20 nM was incubated with 2.5 nM Tb-labeled anti-His antibody, test compound, and fluorescein-labeled cGAMP analog probe (BioLog cat. no. C195) at a concentration of 200 nM (STING WT) or 40 nM (STING AQ) in PBS containing 0.005% Tween-20 and 0.1% BSA for one hour. Fluorescence at 495 nm and 520 nm was measured using an EnVision microplate reader to quantify FRET between Tb-labeled anti-His antibody and fluorescein-labeled probe. Background was defined as the signal obtained in the absence of STING protein, and background subtracted FRET ratios were normalized to the maximum signal obtained in the absence of test compound. These values were converted to a percent inhibition. Percent inhibition was determined for test compounds at 11 concentrations. The $IC_{50}$, defined as the concentration of competing test compound needed to reduce specific binding of the probe by 50%, was calculated using the 4 parameter logistic equation to fit the data

```
STING WT: His-TVMV-S-hSTING(155-341)-H232R
                                        (SEQ ID NO: 1)
MGSSHHHHHHSSGETVRFQGHMSVAHGLAWSYYIGYLRLILPELQARIRTY

NQHYNNLLRGAVSQRLYILLPLDCGVPDNLSMADPNIRFLDKLPQQTGDRA

GIKDRVYSNSIYELLENGQRAGTCVLEYATPLQTLFAMSQYSQAGFSREDR

LEQAKLFCRTLEDILADAPESQNNCRLIAYQEPADDSSFSLSQEVLRHLRQ

EEKEEV

STING AQ: His-TVMV-S-hSTING(155-341)-G230A-R293Q
                                        (SEQ ID NO: 2)
MGSSHHHHHHSSGETVRFQGHMSVAHGLAWSYYIGYLRLILPELQARIRTY

NQHYNNLLRGAVSQRLYILLPLDCGVPDNLSMADPNIRFLDKLPQQTADRA

GIKDRVYSNSIYELLENGQRAGTCVLEYATPLQTLFAMSQYSQAGFSREDR

LEQAKLFCQTLEDILADAPESQNNCRLIAYQEPADDSSFSLSQEVLRHLRQ

EEKEEV
```

| | THP1 Reporter Assays $EC_{50}$ (μM) | | HTRF Binding Assays $IC_{50}$ (μM) | |
|---|---|---|---|---|
| Example # | IRF3 | NFkB | WT | AQ |
| Example 1-1 | 4.94 | 8.05 | 0.09 | 0.01 |
| Example 2-1 | >100 | >100 | 10.29 | 0.60 |
| Example 2-4 | >100 | >100 | 92.35 | 4.85 |
| Example 3-1 | 9.23 | 22.57 | 0.78 | 0.04 |
| Example 3-2 | >100 | >100 | 40.94 | 1.64 |
| Example 3-3 | >100 | >100 | 14.41 | 1.03 |
| Example 3-4 | 7.40 | 19.31 | 1.21 | 0.09 |
| Example 4-1 | 19.01 | 57.14 | 0.66 | 0.05 |
| Example 4-2 | 0.37 | 1.32 | 0.09 | 0.03 |
| Example 5-2 | 0.14 | 0.38 | 93.44 | 13.98 |

We claim:

1. A compound of the formula

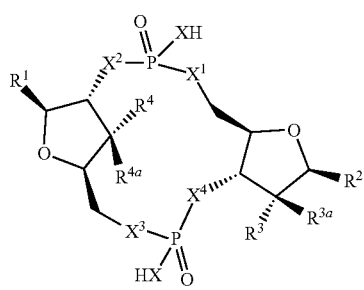

(I)

wherein

X is independently O or S;

X$^1$, X$^2$, X$^3$ and X$^4$ are each independently O or NH;

R$^1$ and R$^2$ are independently

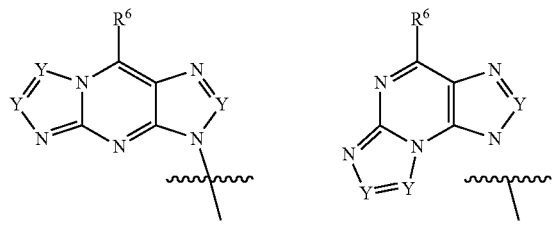

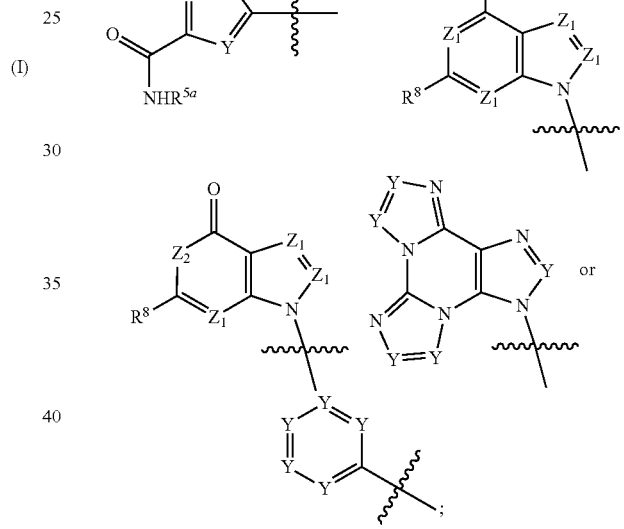

with the proviso that one of R$^1$ and R$^2$ must be each Z$^1$ is independently N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H, $C_{1-3}$ alkyl or $C_{3-6}$ cycloalkyl;

$R^3$ and $R^4$ are independently H, $CH_3$, halogen, —$NR^{a1}R^{a1}$ or $OR^{a1}$;

$R^{3a}$ and $R^{4a}$ are independently H, $CH_3$, halogen, —$NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

2. The compound according to claim 1 of the formula

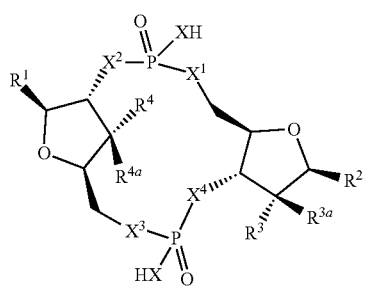

(I)

wherein

X is S;

$X^1$, $X^2$, $X^3$ and $X^4$ are each independently O or NH;

$R^1$ and $R^2$ are independently

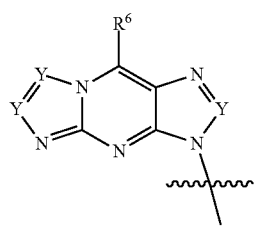

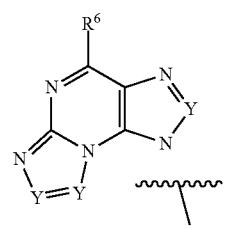

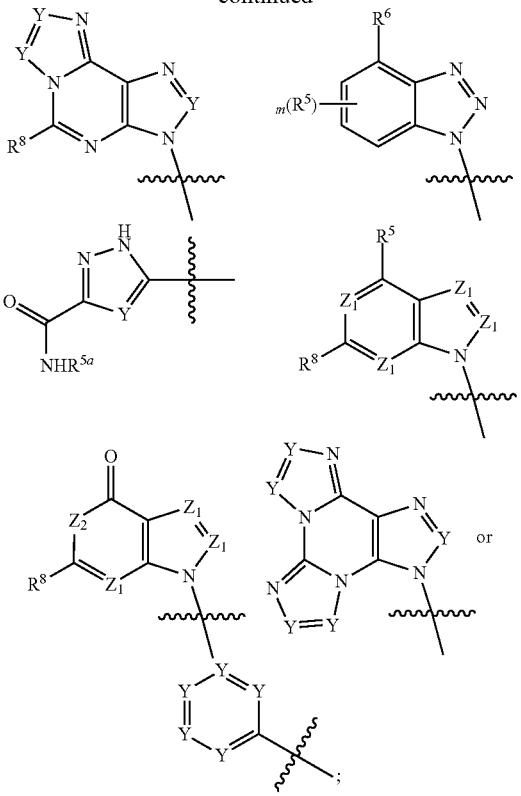

with the proviso that one of $R^1$ and $R^2$ must be

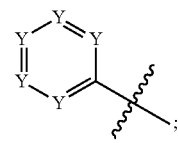

each $Z^1$ is independently N or $CR^a$;

$Z^2$ is NR;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^3$, $C_{3-6}$ cycloalkyl substituted with 0-6 $R^3$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, —$NR^{a1}R^{a1}$ or $OR^{a1}$;

$R^{3a}$ and $R^{4a}$ are independently H, $CH_3$, halogen, —$NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —OC (O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently CR$^a$ or N;

m is 0, 1, 2 or 3;

or a pharmaceutically acceptable salt, tautomer or stereoisomer thereof.

3. The compound according to claim 1 of the formula

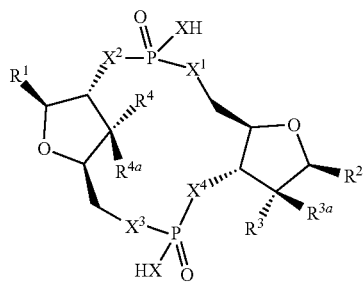

(I)

wherein

X is O;

X$^1$, X$^2$, X$^3$ and X$^4$ are each independently O or NH;

R$^1$ and R$^2$ are independently

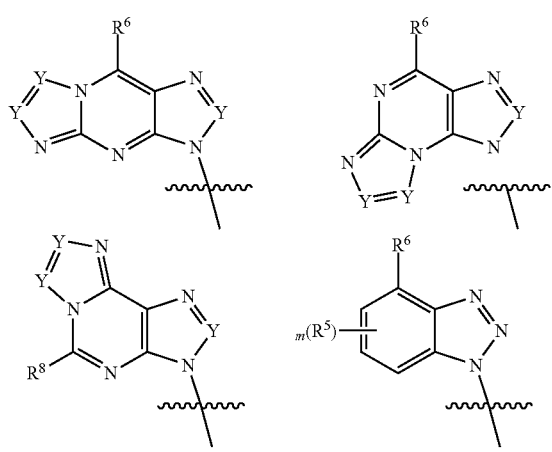

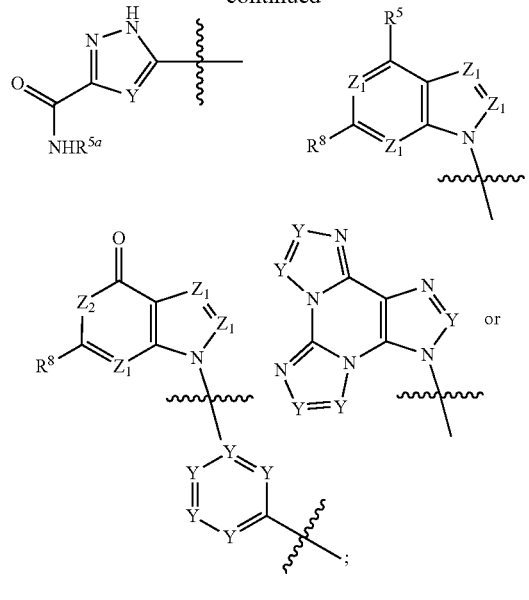

with the proviso that one of R$^1$ and R$^2$ must be each Z$^1$ is independently N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^3$ and R$^4$ are independently H, CH$_3$, halogen, —NR$^{a1}$R$^{a1}$ or OR$^{a1}$;

R$^{3a}$ and R$^{4a}$ are independently H, CH$_3$, halogen, —NR$^{a1}$R$^{a1}$ or OR$^{a1}$; or R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently CR$^a$ or N;

m is 0, 1, 2 or 3;

or a pharmaceutically acceptable salt, tautomer or stereoisomer thereof.

4. The compound according to claim 1 of the formula

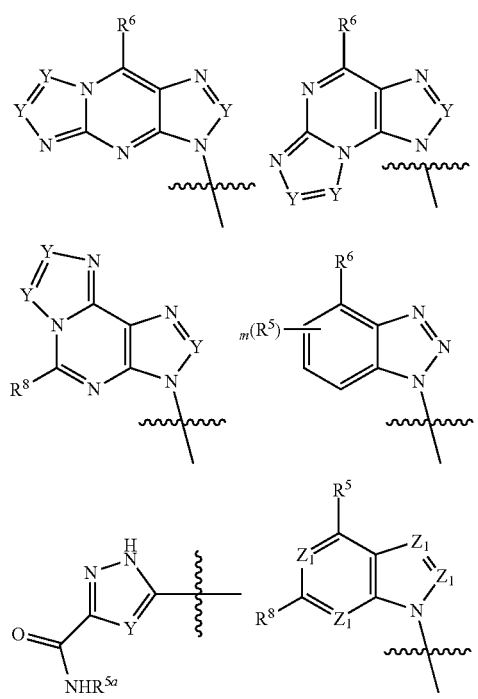

wherein

X$^1$, X$^2$, X$^3$ and X$^4$ are each independently O or NH;

R$^1$ and R$^2$ are independently

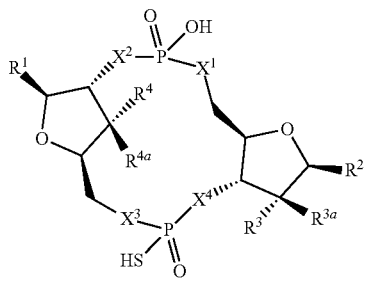

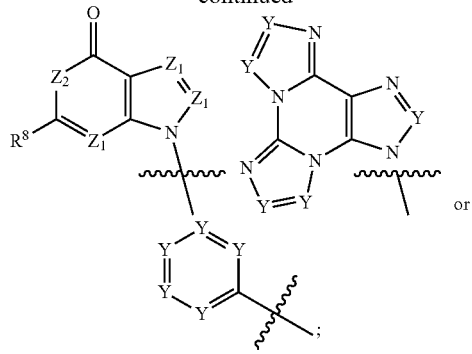

with the proviso that one of R$^1$ and R$^2$ must be

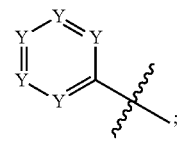

each Z$^1$ is independently N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^3$ and R$^4$ are independently H, CH$_3$, halogen, —NR$^{a1}$R$^{a1}$ or OR$^{a1}$;

R$^{3a}$ and R$^{4a}$ are independently H, CH$_3$, halogen, —NR$^{a1}$R$^{a1}$ or OR$^{a1}$; or R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)

$NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

5. The compound according to claim 1 of the formula

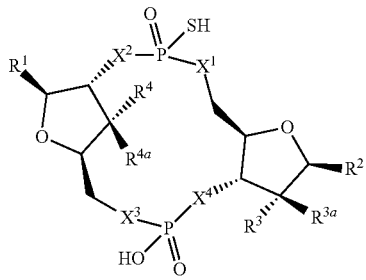

wherein $X^1$, $X^2$, $X^3$ and $X^4$ are each independently O or NH;

$R^1$ and $R^2$ are independently

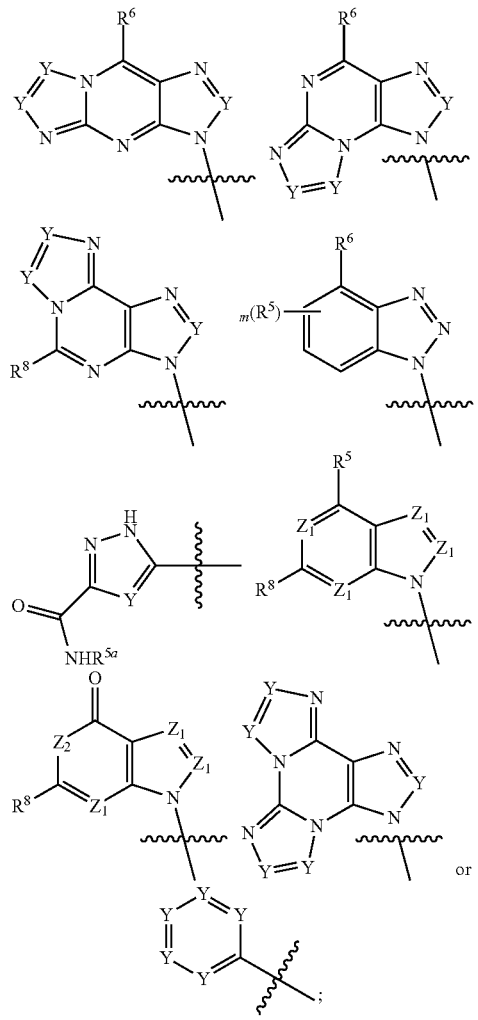

with the proviso that one of $R^1$ and $R^2$ must be

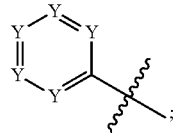

;

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}NR^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ and $R^4$ are independently H, $CH_3$, halogen, $-NR^{a1}R^{a1}$ or $OR^{a1}$;

$R^{3a}$ and $R^{4a}$ are independently H, $CH_3$, halogen, $-NR^{a1}R^{a1}$ or $OR^{a1}$; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-N1R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

6. The compound according to claim 1 of the formula

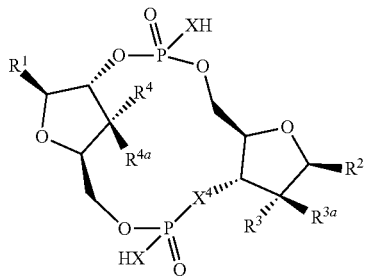

wherein

X is independently O or S;

R$^1$ and R$^2$ are independently

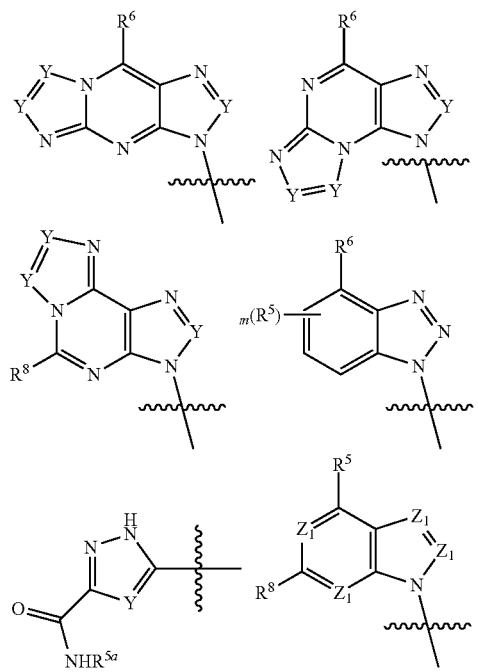

or

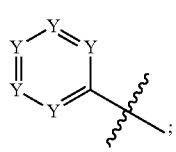

with the proviso that one of R$^1$ and R$^2$ must be

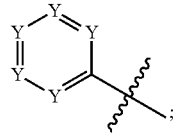

each Z$^1$ is independently N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^3$ and R$^4$ are independently H, CH$_3$, halogen, —NR$^{a1}$R$^{a1}$ or OR$^{a1}$;

R$^{3a}$ and R$^{4a}$ are independently H, CH$_3$, halogen, —NR$^{a1}$R$^{a1}$ or OR$^{a1}$; or R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C═CH$_2$ substituent;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —N1R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently CR$^a$ or N;

m is 0, 1, 2 or 3;

or a pharmaceutically acceptable salt, tautomer or stereoisomer thereof.

7. The compound according to claim 1 of the formula

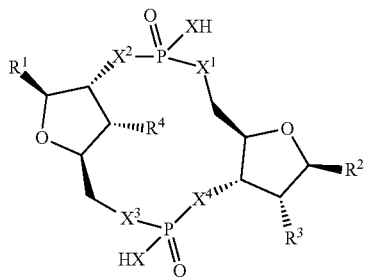

wherein

X is independently O or S;

X¹, X², X³ and X⁴ are each independently O or NH;

R¹ and R² are independently

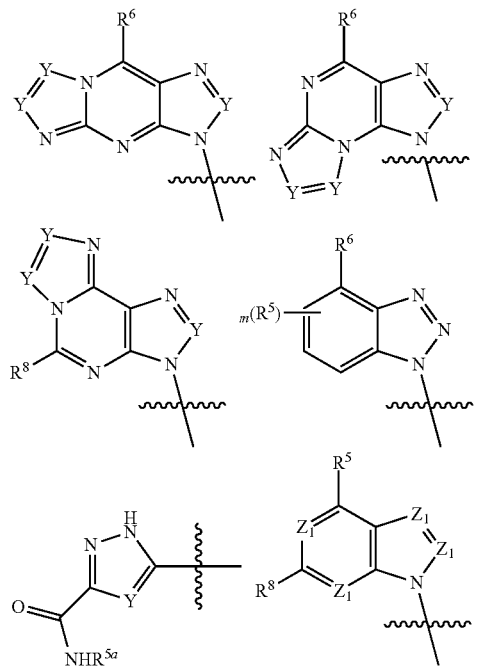

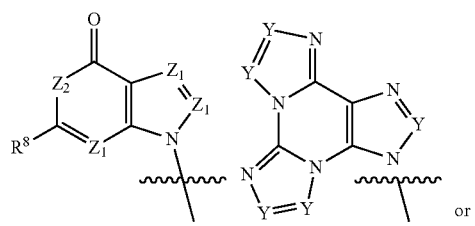

or

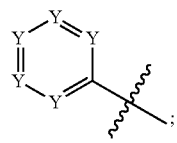

with the proviso that one of R¹ and R² must be

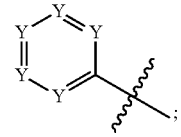

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, NO$_2$, OH, $OR^{a1}$, $SR^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H, $C_{1-3}$ alkyl or $C_{3-6}$ cycloalkyl;

$R^3$ and $R^4$ are independently H, CH$_3$, halogen, —NR$^{a1}$R$^{a1}$ or OR$^{a1}$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently $CR^a$ or N;

m is 0, 1, 2 or 3;

or a pharmaceutically acceptable salt, tautomer or stereoisomer thereof.

8. The compound according to claim 1 of the formula (I)

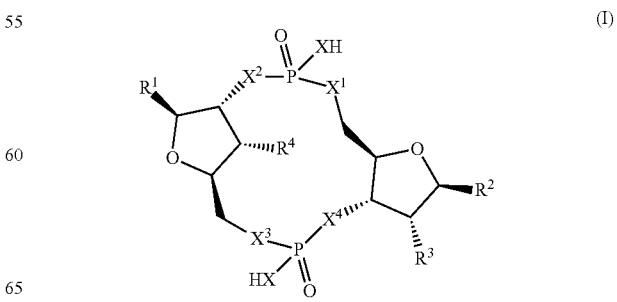

wherein
X is S;
$X^1$, $X^2$, $X^3$ and $X^4$ are each independently O or NH;
$R^1$ and $R^2$ are independently

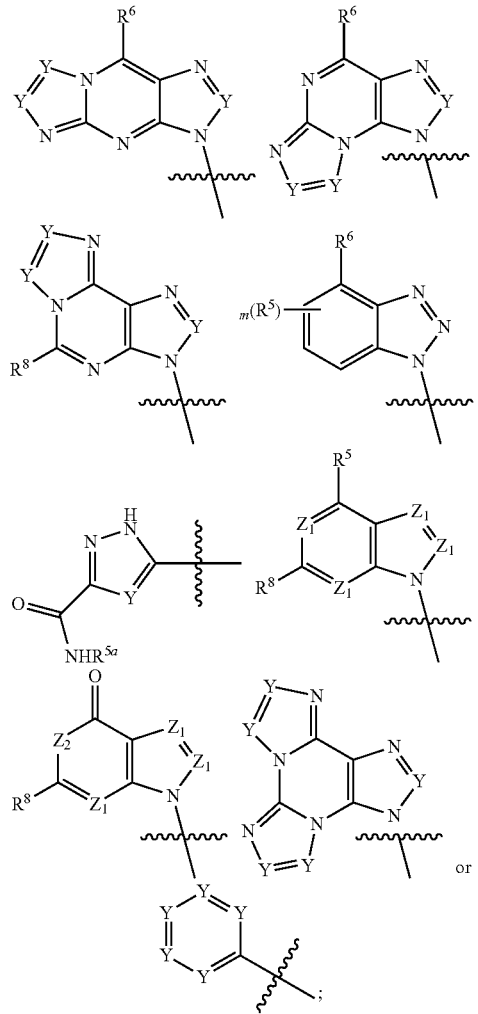

with the proviso that one of $R^1$ and $R^2$ must be

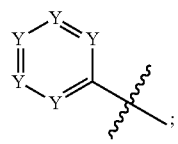

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ and $R^4$ are independently H, $CH_3$, halogen, —$NR^{a1}R^{a1}$ or $OR^{a1}$;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
each Y is independently $CR^a$ or N;
m is 0, 1, 2 or 3;
or a pharmaceutically acceptable salt, tautomer or stereoisomer thereof.

9. The compound according to claim 1 of the formula

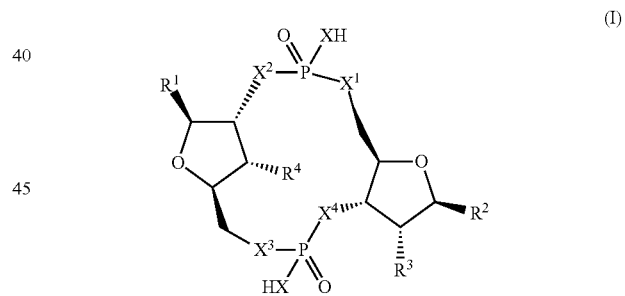

(I)

wherein
X is O;
$X^1$, $X^2$, $X^3$ and $X^4$ are each independently O or NH;
$R^1$ and $R^2$ are independently

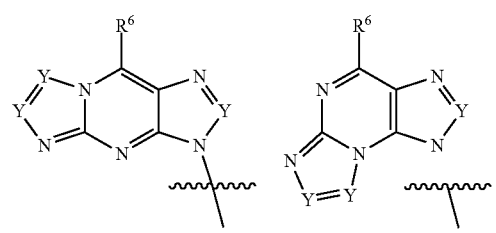

-continued

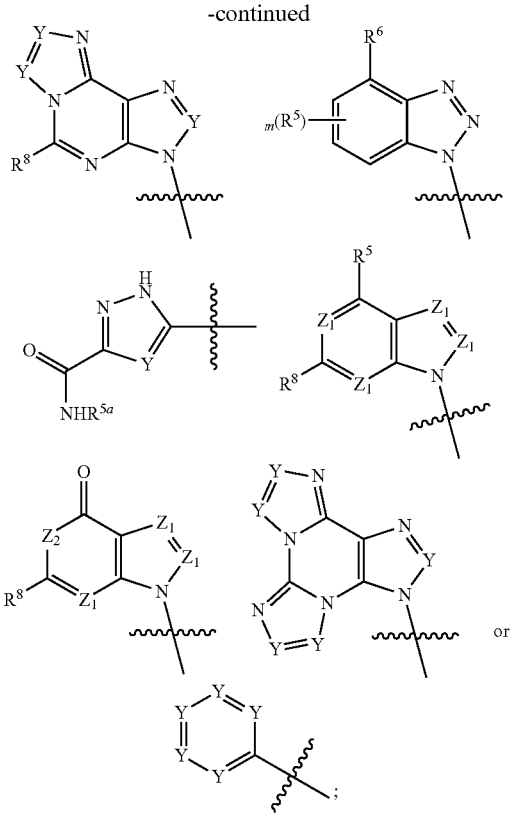

with the proviso that one of $R^1$ and $R^2$ must be

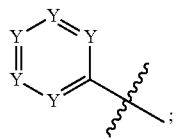

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ and $R^4$ are independently H, $CH_3$, halogen, —$NR^{a1}R^{a1}$ or $OR^{a1}$;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
each Y is independently $CR^a$ or N;
m is 0, 1, 2 or 3;
or a pharmaceutically acceptable salt, tautomer or stereoisomer thereof.

10. The compound according to claim 1 of the formula

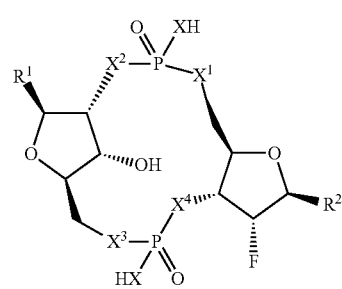

(I)

wherein
X is S;
$X^1$, $X^2$, $X^3$ and $X^4$ are each independently O or NH;
$R^1$ and $R^2$ are independently

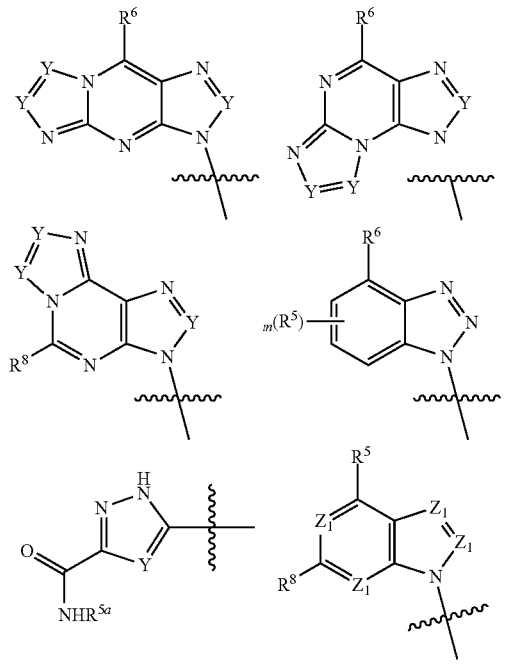

113

-continued

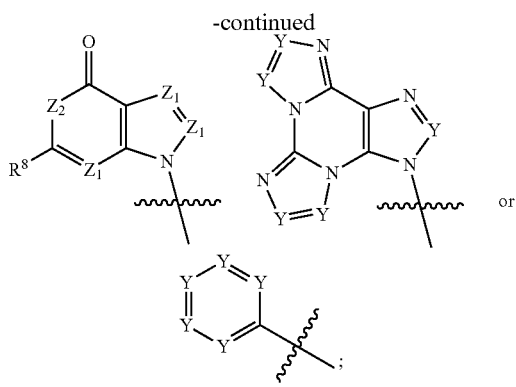

with the proviso that one of $R^1$ and $R^2$ must be

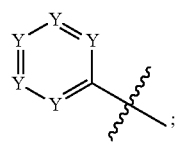

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)NR^{a1}R^{a1}$;
$R^{a1}$ is H, $C_{1-3}$ alkyl or $C_{3-6}$ cycloalkyl;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
each Y is independently $CR^a$ or N;
m is 0, 1, 2 or 3;

114 or a pharmaceutically acceptable salt, tautomer or stereoisomer thereof.

11. The compound according to claim 1 of the formula

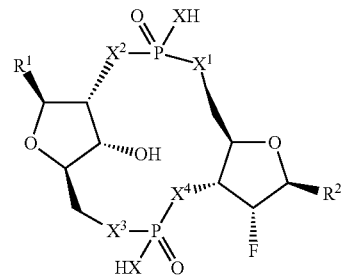

wherein
X is O;
$X^1$, $X^2$, $X^3$ and $X^4$ are each independently O or NH;
$R^1$ and $R^2$ are independently

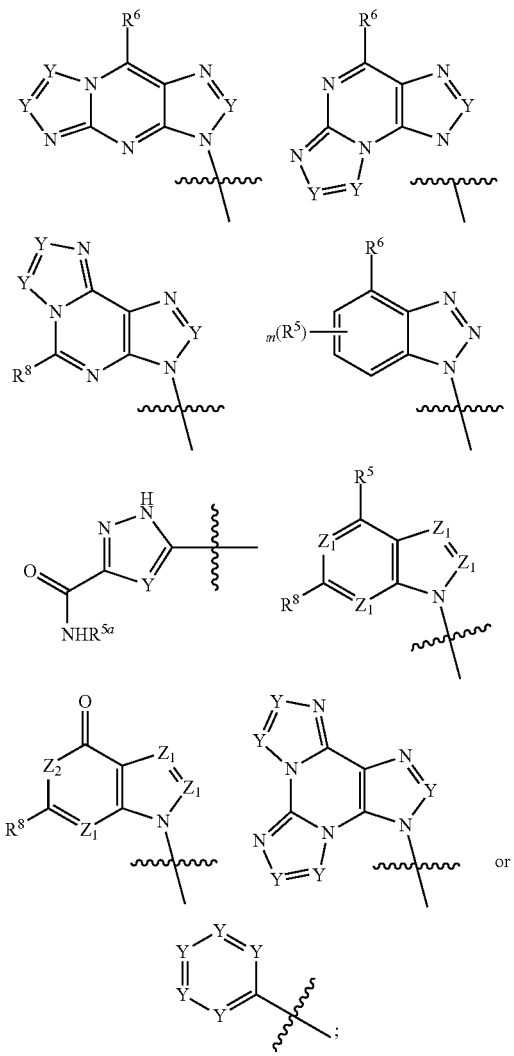

with the proviso that one of $R^1$ and $R^2$ must be

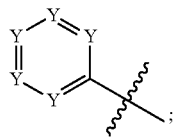

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
each Y is independently $CR^a$ or N;
m is 0, 1, 2 or 3;
or a pharmaceutically acceptable salt, tautomer or stereoisomer thereof.

12. The compound according to claim 1 of the formula

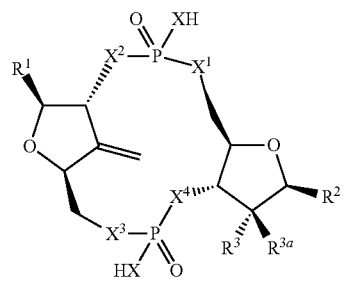

(I)

wherein
X is independently O or S;
$R^1$ and $R^2$ are independently

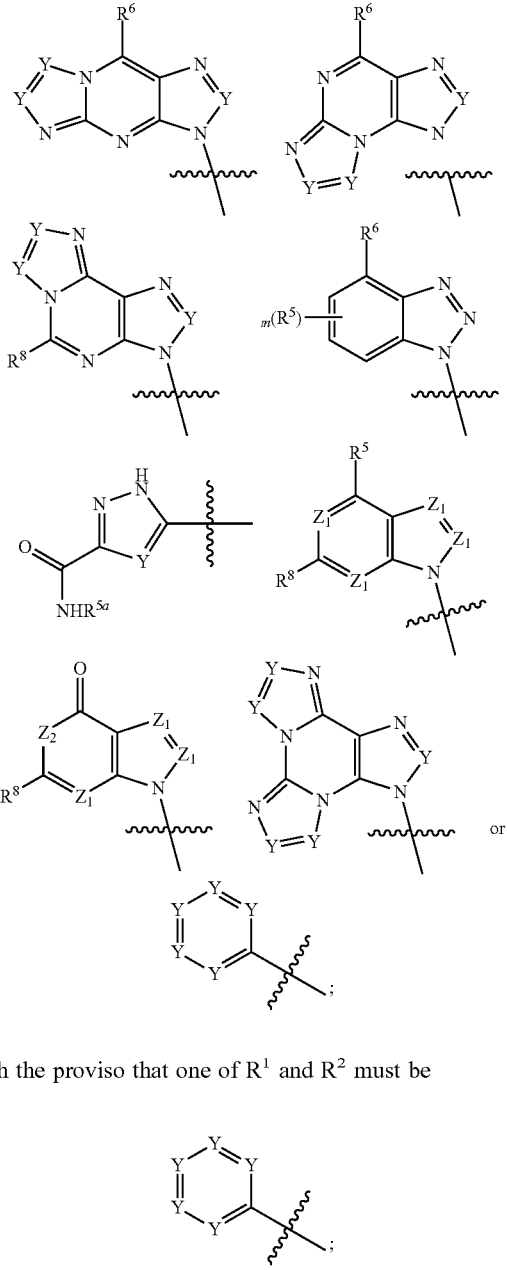

with the proviso that one of $R^1$ and $R^2$ must be

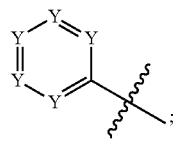

each $Z^1$ is independently N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$R^{a1}$, —$NR^{a1}C(O)R^{a1}$, —$NR^{a1}COOR^{a1}$, —$NR^{a1}C(O)NR^{a1}R^{a1}$, —$NaS(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

each Y is independently $CR^a$ or N;

m is 0, 1, 2 or 3;

or a pharmaceutically acceptable salt, tautomer or stereoisomer thereof.

13. The compound according to claim 1 of the formula

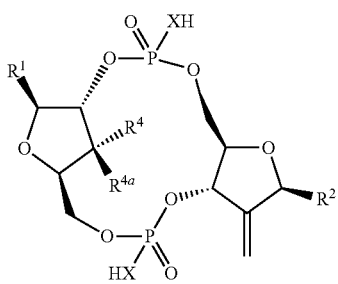

wherein

X is independently O or S;

$R^1$ and $R^2$ are independently

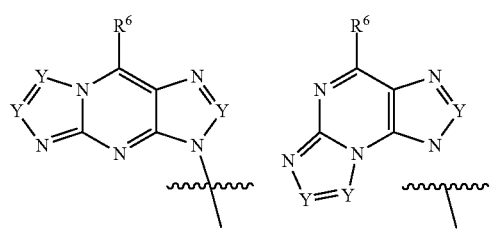

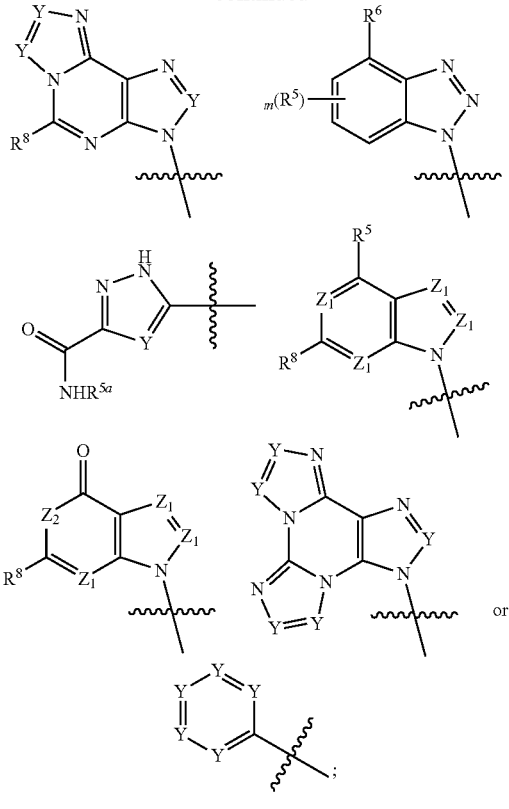

with the proviso that one of $R^1$ and $R^2$ must be

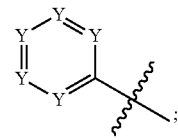

each $Z^1$ is independently N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

each Y is independently CR$^a$ or N;

m is 0, 1, 2 or 3;

or a pharmaceutically acceptable salt, tautomer or stereoisomer thereof.

14. The compound according to claim 1 or a pharmaceutically acceptable salt, tautomer or stereoisomer thereof, which is

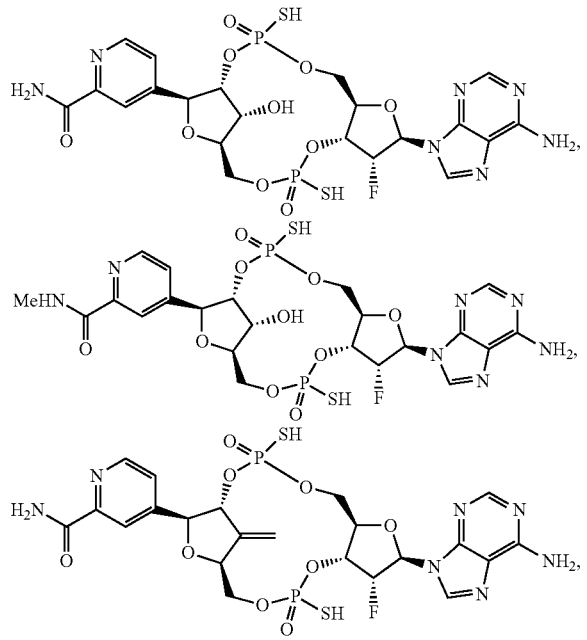

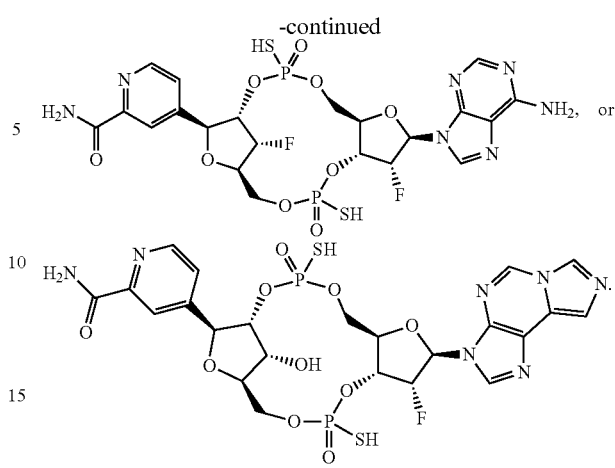

15. A compound according to claim 1 which is

4-[(1R,6R,8R,9R,10R,15R,17S,18R)-8-(6-amino-9H-purin-9-yl)-9-fluoro-18-hydroxy-3,12-dioxo-3,12-disulfanyl-2,4,7,11,13,16-hexaoxa-3λ5,12λ5-diphosphatricyclo[13.2.1.0$^{6,10}$]octadecan-17-yl]pyridine-2-carboxamide, 4-[(1R,6R,8R,9R,10R,15R,17S,18R)-8-(6-amino-9H-purin-9-yl)-9-fluoro-18-hydroxy-3,12-dioxo-3,12-disulfanyl-2,4,7,11,13,16-hexaoxa-3λ$^5$,12λ$^5$-diphospha tricyclo[13.2.1.0$^{6,10}$]octadecan-17-yl]-N-methylpyridine-2-carboxamide, or 4-[(1R,6R,8R,9R,10R,15S,17S)-8-(6-amino-9H-purin-9-yl)-9-fluoro-18-methylidene-3,12-dioxo-3,12-disulfanyl-2,4,7,11,13,16-hexaoxa-3λ5,12λ5-diphosphatricyclo[13.2.1.0$^{6,10}$]octadecan-17-yl]pyridine-2-carboxamide, 4-[(1S,6R,8R,9R,10R,15R,17S,18R)-8-(6-amino-9H-purin-9-yl)-9,18-difluoro-3,12-dioxo-3,12-disulfanyl-2,4,7,11,13,16-hexaoxa-3λ$^5$,12λ$^5$-diphosphatricyclo[13.2.1.0$^{6,10}$]octadecan-17-yl]pyridine-2-carboxamide, 4-[(1R,6R,8R,9R,10R,15R,17S,18R)-9-fluoro-18-hydroxy-8-{3H-imidazo[2,1-f]purin-3-yl}-3,12-dioxo-3,12-disulfanyl-2,4,7,11,13,16-hexaoxa-3λ$^5$,12λ$^5$-diphosphatricyclo[13.2.1.0$^6$,1$^\circ$   ]octadecan-17-yl]pyridine-2-carboxamide or a pharmaceutically acceptable salt thereof.

16. A pharmaceutical composition comprising a compound according to claim 1 or a pharmaceutically acceptable salt thereof and one or more pharmaceutically acceptable carriers, diluents or excipients.

\* \* \* \* \*